US010434188B1

(12) United States Patent
Trippel et al.

(10) Patent No.: US 10,434,188 B1
(45) Date of Patent: Oct. 8, 2019

(54) HYALURONIC ACID BINDING DOMAIN-GROWTH FACTOR FUSION PROTEIN CDNAS AND FUSION PROTEINS FOR CARTILAGE MATRIX PRESERVATION AND REPAIR

(71) Applicants: The Trustees of Indiana University, Indianapolis, IN (US); United States Government as Represented by the Department of Veterans Affairs, Washington, DC (US)

(72) Inventors: Stephen B. Trippel, Indianapolis, IN (US); Shuiliang Shi, Carmel, IN (US)

(73) Assignees: THE TRUSTEES OF INDIANA UNIVERSITY, Indianapolis, IN (US); UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 316 days.

(21) Appl. No.: 14/294,305

(22) Filed: Jun. 3, 2014

Related U.S. Application Data

(60) Provisional application No. 61/830,925, filed on Jun. 4, 2013.

(51) Int. Cl.
| | | |
|---|---|---|
| C07K 14/475 | (2006.01) | |
| C07K 19/00 | (2006.01) | |
| A61K 38/18 | (2006.01) | |
| A61K 48/00 | (2006.01) | |
| C07K 14/65 | (2006.01) | |

(52) U.S. Cl.
CPC .......... *A61K 48/0058* (2013.01); *C07K 14/65* (2013.01)

(58) Field of Classification Search
CPC .. G01N 33/502; G01N 33/5008; G01N 33/68; C07K 14/705; C07K 2319/33; A61K 47/48361; A61K 31/737; A61K 2300/00; A61K 38/1709; A61K 38/177; A61K 38/2013; A61K 38/2053; A61K 38/208; A61K 38/21; A61K 38/19; A61K 47/67; A61K 51/08; B82Y 5/00
See application file for complete search history.

(56) References Cited

U.S. PATENT DOCUMENTS

| | | | | |
|---|---|---|---|---|
| 2006/0239965 | A1* | 10/2006 | Szoka, Jr. ............... | A61K 38/19 424/85.1 |
| 2012/0207753 | A1* | 8/2012 | Yu .................... | C07K 14/70585 424/134.1 |

FOREIGN PATENT DOCUMENTS

WO WO-2013025936 A1 * 2/2013 ........... C12N 15/113

OTHER PUBLICATIONS

USPTO-STIC sequence search (May 6, 2016 pp. 1-6.*
USPTO-STIC sequence search (Apr. 3, 2017) pp. 1-4.*
Zheng et al., Aggrecan Synthesis and Secretion. The Journal of Biological Chemistry vol. 273, No. 21, Issue of May 22, pp. 12999-13006, 1998 (Year: 1998).*
Westling et al., ADAMTS4 Cleaves at the Aggrecanase Site (Glu373-Ala374) and Secondarily at the Matrix Metalloproteinase Site (Asn341-Phe342) in the Aggrecan Interglobular Domain. The Journal of Biological Chemistry vol. 277, No. 18, Issue of May 3, pp. 16059-16066, 2002 (Year: 2002).*
Fortier, "Insulin-like growth factor-I enhances cell-based repair of articular cartilage," The Journal of Bone & Joint Surgery (Br) (2002), vol. 84-B (2), pp. 276-288.
Madry, "Enhanced repair of articular cartilage defects in vivo by transplanted chondrocytes overexpressing insulin-like growth factor I (IGF-I)," Gene Therapy (2005), vol. 12(15), pp. 1171-1179.
Nixon, "Enhanced Repair of Extensive Articular Defects by Insulin-like Growth Factor-I-laden Fibrin Composites," Journal of Orthopaedic Research (1999), vol. 17 (4), pp. 473-487.
Shi, "Effect of Transfection Strategy on Growth Factor Overexpression by Articular Chondrocytes," Journal of Orthopaedic Research (2010), vol. 28(1), pp. 103-109.
Shi, "Regulation of Articular Chondrocyte Aggrecan and Collagen Gene Expression by Multiple Growth Factor Gene Transfer," Journal of Orthopaedic Research (2012), vol. 30(7), pp. 1026-1031, epub Dec. 16, 2011.
Banerji, Suneale et al "Characterization of a Functional Hyaluronan-Binding Domain from the Human CD44 Molecule Expressed in *Escherichia coli*", Protein Expression and Purification, vol. 14, Article No. PT980971, (1998), © 1998 by Academic Press, pp. 371-381.
Day, Anthony J. et al., "Hyaluronan-binding Proteins: Tying Up the Giant", The Journal of Biological Chemistry, vol. 277, No. 7, Issue of Feb. 15, 2002, © 2002 by The American Society for Biochemistry and Molecular Biology, Inc., pp. 4585-4588.

(Continued)

*Primary Examiner* — Kevin K Hill
*Assistant Examiner* — Arthur S Leonard
(74) *Attorney, Agent, or Firm* — Faegre Baker Daniels LLP

(57) ABSTRACT

The present invention provides fusion proteins including a hyaluronic acid-binding domain of a cartilage matrix protein and a conserved region of a growth factor protein. Certain embodiments provide nucleic nucleic acid sequences encoding a fusion protein and compositions thereof. Methods for using fusion polypeptides and nucleic acid molecules discloses herein are also provided. In certain embodiments, the fusion proteins and/or nucleic acid molecules can be used to treat a cartilage matrix protein-related condition in a subject.

36 Claims, 4 Drawing Sheets
(4 of 4 Drawing Sheet(s) Filed in Color)
Specification includes a Sequence Listing.

(56) References Cited

OTHER PUBLICATIONS

Ogino, Shinji et al., "Two-State Conformations in the Hyaluronan-Binding Domain Regulate CD44 Adhesiveness under Flow Condition", Structure, vol. 18, May 12, 2010, © 2010 Elsevier Ltd., pp. 649-656.
Peach, Robert J. et al., "Identification of Hyaluronic Acid Binding Sites in the Extracellular Domain of CD44", The Journal of Cell Biology, vol. 122, No. 1, Jul. 1993, © by The Rockefeller University Press, pp. 257-264.
Vuorio, Joni et al., "Atomistic Fingerprint of Hyaluronon-CD44 Binding", PLOS Computational Biology, Jul. 17, 2017, available on the Internet at https://doi.org/10.1371/journnal.pcbi.1005663; 24 pages.
Ponta, Helmut et al., "CD44: From Adhesion Molecules to Signalling Regulators", Nature Reviews, Molecular Cell Biology, vol. 4, Jan. 2003, © 2003 Nature Publishing Group; pp. 33-45.
Mummert, Mark E. et al., "Development of a Peptide Inhibitor of Hyaluronan-mediated Leukocyte Trafficking", J. Exp. Vied, © 2000 The Rockefeller University Press, vol. 192, No. 6, Sep. 18, 2000; pp. 769-779.

\* cited by examiner

CD44-IGF-I fusion protein

Linker 1: GGSG
Linker 2: GGSGGGSG
Linker 3: GGSGGGSGGGSG
Linker 4: GGGGS
Linker 5: GGGGSGGGGS
Linker 6: GGGGSGGGGSGGGGS
Linker 7: GGSGGS
Linker 8: VIGHPIDSE Cleavage site for EK protease: DDDDK▼
Cleavage site for Furin protease: RVRR▼
Cleavage site for Factor Xa protease: IEGR▼
Cleavage site for MMP protease: DIPEN▼FFG.
Cleavage site for Aggrecanase: NITEGE▼ARGSVI

HYALURONIC ACID BINDING DOMAIN-GROWTH FACTOR FUSION PROTEIN CDNAS AND FUSION PROTEINS FOR CARTILAGE MATRIX PRESERVATION AND REPAIR

CROSS-REFERENCE TO RELATED APPLICATIONS

This application claims priority to U.S. Provisional Application No. 61/830,925, filed on Jun. 4, 2013, the entire disclosure of which is expressly incorporated herein by reference for all purposes.

STATEMENT REGARDING FEDERALLY SPONSORED RESEARCH

This invention was made with government support under AR047702 awarded by the National Institutes of Health. The government has certain rights in this invention.

SEQUENCE LISTING

The Sequence Listing, filed electronically in ASCII text format and identified as 3619_54880_SEQ_LIST_IURTC-11114.txt, was created on May 29, 2014, is 140,103 bytes in size and is hereby incorporated by reference.

BACKGROUND OF THE INVENTION

Articular cartilage damage is a major cause of disability in the form of arthritis and joint trauma. Because articular cartilage lacks the ability to effectively repair itself, articular cartilage repair is an unsolved clinical problem.

Growth factors, such as insulin-like growth factor-I (IGF-1), promote articular chondrocyte reparative activity. When delivered to articular cartilage as potential therapeutic agents, these factors are limited by rapid elimination from the joint, slower uptake by the articular cartilage containing the target cells, and, when present in the cartilage or repair tissue, are subject to diffusion out of the tissue where it is needed.

Biologic agents are needed that can promote cartilage biosynthesis in vitro and in vivo. A promising candidate for improving articular chondrocyte function is IGF-1. This polypeptide growth factor has been shown to stimulate the synthesis of type-2 collagen and aggrecan, two principle constituents of cartilage matrix, to stimulate the division of articular chondrocytes and to decrease the endogenous catabolic activity of these cells. Therapeutic application of IGF-1 to cartilage repair has been reported in animal models when delivered as a protein, or by gene transfer. However, an unpublished clinical trial of IGF-1 delivery to human knee joints was evidently unsuccessful. A major limitation of current approaches to IGF-1 therapy include: 1) The rapid removal of IGF-1 from the joint through the synovium, 2) the relatively slow diffusion of IGF-1 into the articular cartilage where it can act on the cells, and 3) limited responsiveness of arthritic chondrocytes to the IGF-1. A means of simultaneously providing cells, IGF-1, and of gradual IGF-1 release over time is needed.

The foregoing example of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

The present invention provides isolated nucleic acid molecules comprising a nucleic acid sequence that encodes a fusion protein comprising: a.) a hyaluronic acid-binding domain of a cartilage matrix protein (HAB) operably linked to b.) a conserved region of a growth factor protein (GF), wherein said fusion protein is capable of up-regulating glycosaminoglycan (GAG) expression in chondrocytes.

Also provided are such isolated nucleic acid molecules herein, wherein the nucleic acid molecule further comprises a nucleic acid sequence that encodes at least one signal peptide (SP).

Also provided are such isolated nucleic acid molecules herein, wherein the nucleic acid molecule encodes a fusion protein which further comprises at least one linker sequence.

Also provided are such isolated nucleic acid molecules herein, wherein the nucleic acid molecule encodes a fusion protein which further comprises at least one protease cleavage sequence.

Also provided are such isolated nucleic acid molecules herein, wherein the nucleic acid molecule encodes a fusion protein which further comprises at least one additional functional peptide.

Also provided are such isolated nucleic acid molecules herein, wherein the order of operably-linked elements, 5' to 3' is: SP-HAB-GF.

Also provided are such isolated nucleic acid molecules herein, wherein the order of operably-linked elements, 5' to 3' is: SP-HAB-GF-additional peptide sequence.

Also provided are such isolated nucleic acid molecules herein, wherein the order of operably-linked elements, 5' to 3' is: SP-HAB-linker-GF-additional peptide sequence.

Also provided are such isolated nucleic acid molecules herein, wherein the order of operably-linked elements, 5' to 3' is: SP-HAB-linker-protease cleavage sequence-GF-additional peptide sequence.

Also provided are such isolated nucleic acid molecules herein, wherein the SP is selected from the group consisting of: aggrecan signal peptide; CD44 signal peptide; link protein signal peptide; TSG-6 signal peptide; versican signal peptide; and other HA-binding protein signal peptide.

Also provided are such isolated nucleic acid molecules herein, wherein the HAB element comprises a polynucleotide fragment of a nucleotide sequence encoding a protein selected from the group consisting of: aggrecan; CD44; link protein; TSG-6; versican; and other HA-binding proteins.

Also provided are such isolated nucleic acid molecules herein, wherein the linker is selected from the group consisting of: Linker 1: GGSG (SEQ ID NO: 1); Linker 2: GGSGGGSG (SEQ ID NO: 2); Linker 3: GGSGGGSGGGSG (SEQ ID NO: 3); Linker 4: GGGGS (SEQ ID NO: 4); Linker 5: GGGGSGGGGS (SEQ ID NO: 5); Linker 6: GGGGSGGGGSGGGGS (SEQ ID NO: 6); Linker 7: GGSGGS (SEQ ID NO: 7); and Linker 8: VIGHPIDSE (SEQ ID NO: 8).

Also provided are such isolated amino acid molecules herein, further comprising a cleavage site for a protease selected from the group consisting of: enterokinase (EK); Furin; Factor Xa; Matrix metalloproteinase (MMP); and Aggrecanase.

Also provided are such isolated nucleic acid molecules herein, wherein the GF is selected from the group consisting of: IGF-1; BMP2; BMP4; BMP7; FGF2; FGF18; GDF5; TGF-β1; TGF-β3; and other growth factors that influence the target cells.

Also provided are such isolated nucleic acid molecules herein, wherein the additional peptide sequence is selected from the group consisting of: IGF-I signal peptide; and IGF-I E peptide.

Also provided are such polypeptides, wherein the CD44 HAB element is selected from the group consisting of: amino acids 1-132 of SEQ ID NO: 64; amino acids 1-156 of SEQ ID NO: 68; 1-178 of SEQ ID NO: 72; and 1-222 of SEQ ID NO: 76.

Also provided are such isolated nucleic acid molecules herein, wherein the nucleic acid molecule encodes a fusion protein comprising HAB and IGF-1 linked by a number of amino acids selected from the group consisting of: at least about 60 amino acids, at least about 50 amino acids, at least about 40 amino acids, at least about 30 amino acids, at least about 20 amino acids, fewer than 20 amino acids; fewer than 15 amino acids; fewer than 10 amino acids; fewer than 5 amino acids; no amino acids.

Also provided are such isolated nucleic acid molecules herein, wherein the nucleic acid molecule is selected from the group consisting of DNA and RNA.

Also provided are such isolated nucleic acid molecules herein, wherein the nucleic acid molecule comprises:
a.) one or more signal peptide (SP);
b.) one or more hyaluronic acid-binding domain nucleic acid construct (HAB);
c.) one or more linker sequence (linker sequence);
d.) one or more protease cleavage sequence (protease cleavage sequence);
e.) one or more conserved region of a growth factor protein sequence (GF conserved region sequence);
f.) one or more additional peptide sequence (additional peptide); wherein the nucleic acids are operably linked so as to express a functional fusion protein.

Also provided are plasmids comprising a nucleic acid molecule herein.

Also provided are expression vectors comprising a nucleic acid molecule herein.

Also provided are expression vectors herein, which further comprises at least one regulatory element.

Also provided are expression vectors herein, wherein the regulatory element is selected from the group consisting of: promoter; repressor; enhancer; activator; and transcription factor.

Also provided are expression vectors herein, which is a viral vector.

Also provided are expression vectors herein, which is an adeno-associated virus plasmid (pAAV).

Also provided are cells transformed, transfected or transduced by a vector herein.

Also provided are cells herein, which is a chondrocyte.

Also provided are animal models comprising an expression vector herein.

Also provided are fusion proteins, comprising: a.) at least one hyaluronic acid-binding domain of a cartilage matrix protein (HAB) linked to b.) at least one conserved region of a growth factor protein (GF), wherein said fusion protein is capable of upregulating glycosaminoglycan (GAG) expression in chondrocytes.

Also provided are fusion proteins herein, wherein the fusion protein upregulates GAG expression in chondrocytes by 20-50%, 30-70%, 50-100%, 75-200%, 100-300%, or 200-500%.

Also provided are fusion proteins herein, which further comprise at least one signal peptide (SP).

Also provided are fusion proteins herein, which further comprise at least one linker peptide.

Also provided are fusion proteins herein, which further comprise at least one protease cleavage sequence.

Also provided are fusion proteins herein, which further comprise at least one additional functional peptide.

Also provided are fusion proteins herein, wherein the order of elements, N-terminus to C-terminus is: SP-HAB-GF.

Also provided are fusion proteins herein, wherein the order of elements, N-terminus to C-terminus is: SP-HAB-GF-additional peptide sequence.

Also provided are fusion proteins herein, wherein the order of elements, N-terminus to C-terminus is: SP-HAB-linker-GF-additional peptide sequence.

Also provided are fusion proteins herein, wherein the order of elements, N-terminus to C-terminus is: SP-HAB-linker-protease cleavage sequence-GF-additional peptide sequence.

Also provided are fusion proteins herein, wherein the SP is selected from the group consisting of: aggrecan signal peptide, CD44 signal peptide; link protein signal peptide; TSG-6 signal peptide, versican signal peptide; and other HA-binding protein signal peptide.

Also provided are fusion proteins herein, wherein the HAB is selected from the group consisting of: aggrecan; CD44; link protein; TSG-6; versican; and other HA-binding proteins.

Also provided are fusion proteins herein, wherein the linker is selected from the group consisting of: Linker 1: GGSG (SEQ ID NO: 1); Linker 2: GGSGGGSG (SEQ ID NO: 2); Linker 3: GGSGGGSGGGSG (SEQ ID NO: 3); Linker 4: GGGGS (SEQ ID NO: 4); Linker 5: GGGGSGGGGS (SEQ ID NO: 5); Linker 6: GGGGSGGGGSGGGGS (SEQ ID NO: 6); Linker 7: GGSGGS (SEQ ID NO: 7); and Linker 8: VIGHPIDSE (SEQ ID NO: 8).

Also provided are fusion proteins herein, comprising a protease cleavage site selected from the group consisting of: SEQ ID NO: 9; SEQ ID NO: 10; SEQ ID NO: 11; SEQ ID NO: 12; and SEQ ID NO: 13.

Also provided are fusion proteins herein, wherein the GF is selected from the group consisting of: IGF-1; BMP2; BMP4; BMP7; FGF2; FGF18; GDF5; TGF-β1 and TGF-β3 and other growth factors that influence the target cells.

Also provided are fusion proteins herein, wherein the additional peptide sequence is selected from the group consisting of: IGF-I signal peptide; and IGF-I E peptide.

Also provided are fusion proteins herein, wherein the CD44 HAB element is selected from the group consisting of: CD44(132); CD44(156); CD44(178); and CD44(222).

Also provided are fusion proteins herein, which comprise a number of flanking amino acids to the HAB, wherein the number of flanking amino acids is selected from the group consisting of: 5 amino acids; 10 amino acids; 15 amino acids; 20 amino acids; 25 amino acids; 30 amino acids; 35 amino acids; 40 amino acids; 45 amino acids; 50 amino acids; 55 amino acids; and 60 amino acids.

Also provided are fusion proteins herein, which comprise a number of flanking amino acids to the HAB, wherein the flanking amino acids are at the N terminus of HAB, and wherein the number of flanking amino acids is selected from the group consisting of: 5 amino acids; 10 amino acids; 15 amino acids; 20 amino acids; 25 amino acids; 30 amino acids; 35 amino acids; 40 amino acids; 45 amino acids; 50 amino acids; 55 amino acids; and 60 amino acids.

Also provided are fusion proteins herein, which comprise a number of flanking amino acids to the HAB, wherein the flanking amino acids are at the C terminus of HAB, and wherein the number of flanking amino acids is selected from the group consisting of: 5 amino acids; 10 amino acids; 15 amino acids; 20 amino acids; 25 amino acids; 30 amino acids; 35 amino acids; 40 amino acids; 45 amino acids; 50 amino acids; 55 amino acids; and 60 amino acids.

Also provided are compositions comprising a nucleic acid molecule herein and a pharmaceutically-acceptable carrier.

Also provided are compositions comprising a fusion protein herein and a pharmaceutically-acceptable carrier.

Also provided are methods of producing a fusion protein comprising expressing a nucleic acid molecule herein in at least one cell.

Also provided are methods herein, wherein the cell is selected from the group consisting of prokaryotic cell and eukaryotic cell.

Also provided are methods herein, wherein the cell is a chondrocyte.

Also provided are methods to upregulate glycosaminoglycan expression in at least one chondrocyte, comprising expressing a nucleic acid molecule herein in at least one chondrocyte.

Also provided are methods to increase GF diffusion rates to the articular cartilage of a subject, comprising expressing a nucleic acid molecule herein in at least one chondrocyte in at least one joint of a subject and increasing GF diffusion rates to the articular cartilage of the subject.

Also provided are methods to increase responsiveness rates of arthritic chondrocytes to GF in a subject, comprising expressing a nucleic acid molecule herein in at least one chondrocyte in at least one arthritic joint of a subject and increasing responsiveness rates of arthritic chondrocytes to GF in the subject.

Also provided are methods to treat cartilage matrix protein-related pathology in a subject, comprising expressing a nucleic acid molecule herein in at least one chondrocyte in the cartilage matrix of a subject with cartilage matrix protein-related pathology and treating cartilage matrix protein-related pathology in the subject.

Also provided are methods herein, wherein the cartilage matrix protein-related pathology is selected from the group consisting of: joint stiffness; degenerative disease; facet disease; osteoarthritis; and rheumatoid arthritis.

Also provided are methods to ameliorating joint pain or intervertebral disc pain in a subject, comprising expressing a nucleic acid molecule herein in at least one painful joint or painful intervertebral disc of a subject and ameliorating joint pain or intervertebral disc pain in the subject.

Also provided are methods to ameliorate the symptoms of joint injury or intervertebral disc injury in a subject, comprising expressing a nucleic acid molecule herein in at least one injured joint or injured intervertebral disc of a subject and ameliorating the symptoms of joint injury or intervertebral disc injury in the subject.

Also provided are methods herein, wherein the cartilage matrix, joint, and/or intervetebral disc injury is selected from the group consisting of: traumatic injury; surgical injury; degenerative disease; developmental defect; and work injury.

Also provided are methods to increase sports performance in an athlete, comprising expressing a nucleic acid molecule herein in at least one joint or intervertebral disc of an athlete and increasing sports performance in the athlete.

Also provided are methods herein, wherein the sports performance is selected from the group consisting of: increased speed; increased endurance; increased weight-lifting ability; increased flexibility; increased strength; increased resistance to impact; increased concentration; and increased career length.

Also provided are methods herein, wherein the subject or athlete is a mammal selected from the group consisting of: laboratory animal; companion animal; draft animal; meat animal; and human.

Also provided are methods herein, wherein the subject or athlete is a mammal selected from the group consisting of: cat; dog; horse; bovine; and human.

Also provided are methods herein, wherein the cartilage matrix is selected from the group consisting of: toe; ankle; knee; hip; spine; shoulder; neck; elbow; wrist; fingers; and thumb.

Also provided are methods herein, wherein the cartilage matrix is selected from the group consisting of: cartilage of the nose; and cartilage of the ear.

Also provided are methods herein, wherein the cartilage matrix is at least one intervertebral disc.

Also provided are methods to upregulate glycosaminoglycan expression in at least one chondrocyte, comprising introducing a fusion protein herein to at least one chondrocyte.

Also provided are methods to decrease GF removal rates from the joint synovium or intervertebral disc synovium of a subject, comprising introducing a fusion protein herein in at least one joint or inteverteberal disc of a subject and decreasing GF removal rate from the joint synovium or intervertebral disc of the subject.

Also provided are methods to increase responsiveness rates of chondrocytes to GF in a subject, comprising introducing a fusion protein herein in at least one chondrocyte of a subject and increasing responsiveness rates of chondrocytes to GF in the subject.

Also provided are methods to ameliorate cartilage matrix protein-related pathology in a subject, comprising introducing a fusion protein herein in the cartilage matrix of a subject with cartilage matrix protein-related pathology and ameliorating cartilage matrix protein-related pathology in the subject.

Also provided are method herein, wherein the cartilage matrix protein-related pathology is selected from the group consisting of: joint stiffness; degenerative joint disease; facet disease; osteoarthritis; and rheumatoid arthritis.

Also provided are methods to ameliorate joint pain or intervertebral disc pain in a subject, comprising introducing a fusion protein herein in at least one painful joint or painful intervertebral disc of a subject and ameliorating joint pain or intervetebral disc pain in the subject.

Also provided are methods to ameliorate the symptoms of joint or intervertebral disc injury in a subject, comprising introducing a fusion protein herein in at least one injured joint or intervertebral disc of a subject and ameliorating the symptoms of joint or intervertebral disc injury in the subject.

Also provided are methods herein, wherein the joint or intervertebral disc injury is selected from the group consisting of: traumatic injury; surgical injury; degenerative disease; developmental defect; and work injury.

Also provided are methods to increase sports performance in an athlete, comprising introducing a fusion protein herein in at least one joint or intervertebral disc of an athlete and increasing sports performance in the athlete.

Also provided are methods herein, wherein the sports performance is selected from the group consisting of: increased speed; increased endurance; increased weight-lifting ability; increased flexibility; increased strength; increased resistance to impact; increased concentration; and increased career length.

Also provided are methods herein, wherein the subject or athlete is a mammal selected from the group consisting of: laboratory animal; companion animal; draft animal; meat animal; and human.

Also provided are methods herein, wherein the subject or athlete is a mammal selected from the group consisting of: cat; dog; horse; bovine; and human.

Also provided are methods herein, wherein the cartilage matrix is selected from the group consisting of: toe; ankle; knee; hip; spine; shoulder; neck; elbow; wrist; fingers; and thumb.

Also provided are methods herein, wherein the cartilage matrix is selected from the group consisting of: cartilage of the nose; and cartilage of the ear.

Also provided are methods herein, wherein the cartilage matrix is at least one intervertebral disc.

Also provided is the invention as shown and described herein.

The term "joint cavity," "joint space," and "joint capsule" refer to a hollow or fluid-filled place or depression in the place of union or junction between two or more bones of the skeleton, including the space of a synovial joint, enclosed by the synovial membrane and articular cartilages.

The terms "treat", "treatment," and "treating" and/or "ameliorating" include pathology reduction, reduction in symptoms, preventative (e.g., prophylactic) and palliative care.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A: Human aggrecan and versican precursors each contains a signal peptide (SP) and G1 domain thereafter, which is responsible for aggrecan and versican binding to HA. Link protein consists of a signal peptide and a mature link protein peptide, which is homologous to the G1 domains of aggrecan and versican and also functions to bind to HA. Human IGF-I precursor consists of a signal peptide (aa 1-48), mature IGF-I peptide (aa 49-118) and E peptide (aa 119-153).

FIG. 1B: HAB-IGF-I fusion proteins (AG1-IGF-I, LP-IGF-I and VG1-IGF-I) were made up of human HA binding protein (aggrecan, link protein and versican) and human IGF-I, each box representing a native domain or region of human aggrecan, link protein and versican. HAB-IGF-I fusion protein AG1-IGF-I was created by fusion of aggrecan (aa 1-357) to IGF-I (aa 49-153), HAB-IGF-I fusion protein LP-IGF-I was created by fusion of link protein (aa 1-354) to IGF-I (aa 49-153) and HAB-IGF-I fusion protein VG1-IGF-I was created by fusion of versican (aa 1-363) to IGF-I (aa 49-153).

FIG. 2A: Human CD44 precursor consists of a 20 aa signal peptide (SP), an extracellular region from AA21 to AA268, a 20 aa transmembrane region (TM) and a 73 aa of the intracellular region at c-terminal. The extracellular region from AA21 to AA268 contains the HA-binding domain, which is responsible for the binding of CD44 to HA. The human IGF-I precursor consists of a signal peptide (aa 1-48), mature IGF-I peptide (aa 49-118) and E peptide (aa 119-153).

FIG. 2B: CD44-IGF-I fusion proteins were made up of human CD44 and human IGF-I, each box representing a native domain or region of human CD44 and human IGF-I. CD44(132)-IGF-I was created by fusion of CD44(aa 1-132) to IGF-I(aa 49-153), CD44(156)-IGF-I was created by fusion of CD44 (aa 1-156) to IGF-I(aa 49-153), CD44(178)-IGF-I was created by fusion of CD44(aa 1-178) to IGF-I(aa 49-153), CD44(222)-IGF-I was created by fusion of CD44 (aa 1-222) to IGF-I(aa 49-153).

FIG. 3A: Human CD44 precursor consists of a 20 aa signal peptide (SP), an extracellular region from AA21 to AA268, a 20 aa transmembrane region (TM) and a 73 aa of the intracellular region at c-terminal. The extracellular region from AA21 to AA268 contains the HA-binding domain, which is responsible for the binding of CD44 to HA. The human IGF-I precursor consists of a signal peptide (aa 1-48), mature IGF-I peptide (aa 49-118) and E peptide (aa 119-153).

FIG. 3B: CD44(178)-IGF-I fusion protein was created by fusion of CD44 (aa 1-178) to IGF-I(aa 49-153).

FIG. 3C: CD44(178)-IGF-I fusion protein with linker was created by inserting a linker sequence after the sequence of CD44(178) and before the sequence of IGF-I in CD44(178)-IGF-I. FIG. 3C discloses SEQ ID NOS 1-8, respectively, in order of appearance.

FIG. 4A) Human versican precursor contains G1 domain (VG1). It is responsible for versican binding to HA. The human IGF-I precursor consists of a signal peptide (aa 1-48), mature IGF-I peptide (aa 49-118) and E peptide (aa 119-153).

FIG. 4B) VG1-IGF-I was created by fusion of versican (aa 1-363) to IGF-I (aa 49-153).

FIG. 4C) VG1-IGF-I fusion protein with protease cleavage site was created by inserting the designated protease cleavage site sequences after the sequence of VG1 and before the sequence of IGF-I in VG1-IGF-I. The triangle (▼) indicates the point of cleavage within the cleavage site sequence. FIG. 4C discloses SEQ ID NOS 9-13, respectively, in order of appearance.

Figure 1A:
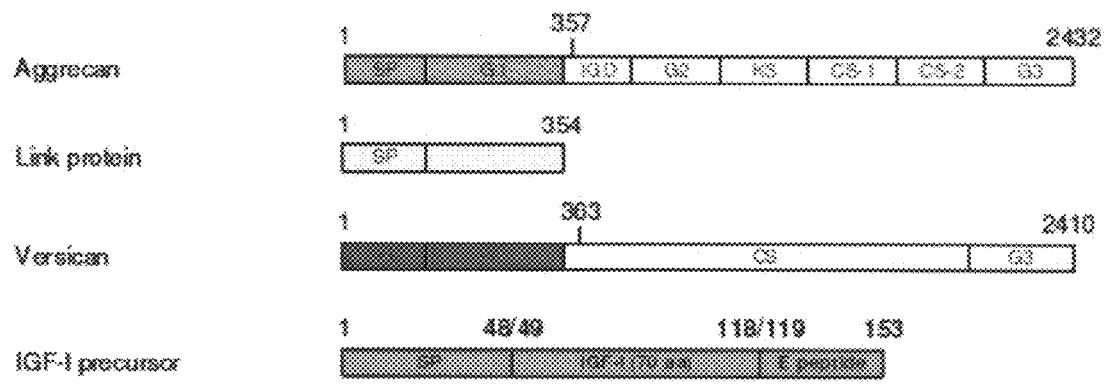
FIGS. 1A-1B. Schematic illustration of three HA binding proteins (aggrecan, link protein and versican) and human IGF-I (FIG. 1A), and HAB-IGF-I fusion proteins (FIG. 1B).

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION OF THE INVENTION

Described are a set of related but distinct nucleic acid molecules that encode fusion proteins comprised by a hyaluronic acid-binding domain and insulin-like growth factor-I. Cells to which such nucleic acid molecules are transferred manufacture the fusion protein. Using a gene therapy approach, the fusion protein is made by the chondrocytes themselves. The nucleic acid molecules are designed to enable their protein products to 1) remain within the articular cartilage and/or repair tissue by matrix hyaluronic acid (HA) binding to the fusion protein's hyaluronic acid-binding domain and 2) stimulate chondrocyte reparative activity by insulin-like growth factor-I (IGF-1) binding to its cell surface receptors.

In addition, by putting a protease cleavage site between the HA tags and IGF-1, the binding of the HA to the cartilage matrix may be regulated. Further, a sustained release formulation is contemplated herein. The present invention may also be used to release growth factor (GF) in other organs, such as by creating an HA scaffolding in an area of the body so that the GF can be concentrated in one place and released as needed.

An important aspect of embodiments of the present invention is the retention of the molecule within a tissue when delivered as a protein. Further, those tissues that are deficient in matrix elements, for example—if it had already lost constituents, are particularly influenced by such fusion proteins. Without being bound by any particular theory, the fusion proteins facilitate the ability of the growth factor to enter the tissue.

In addition, the fusion protein, when purified from the conditioned medium of producer cells carrying the fusion protein nucleic acid molecule(s), may be used as a therapeutic agent using any of a variety of available protein delivery methods.

In one embodiment, there are provided DNA constructs encoding fusion proteins. The constructs contain the coding region for the mature form of insulin-like 1 (IGF-1). The constructs contain the coding region of at least one cartilage matrix protein hyaluronic acid-binding domain (HAB). The constructs may optionally contain signal peptide and carboxy-terminal extension peptide (E peptide). Vectors containing these cDNA constructs are designed to be transferred into target cells, enabling the cells to produce the encoded fusion proteins and provide local delivery of IGF-1 for tissue repair.

In another embodiment, vectors containing the DNA constructs are designed to be transferred into cultured cells and the fusion protein is recovered from the conditioned media. Examples of cell lines useful for this embodiment include Chinese Hamster Ovary (CHO) cells and HEK-293 cells Human Embryonic Kidney 293 (HEK-293) cells. The fusion protein is then purified, combined with a pharmaceutically acceptable excipient, and formulated into a therapeutically effective dose.

EXAMPLES

Example 1. Materials and Methods

Fusion Proteins

The nucleic acid sequences encoding the described proteins and chimeric nucleic acid sequences encoding fusion proteins may be constructed. The chimeric nucleic acid molecules may be prepared with sections encoding a linking peptide connecting the protein portions of the encoded fusion protein. Optionally, the peptide linker may be selected to include residues imparting stearic flexibility in order to enhance the function of the fusion protein.

Fusion Protein Linkers

The components of the fusion proteins may be operatively linked directly one to the other. The two protein components of the fusion protein may be directly linked via an amino terminus to carboxy terminus peptide bond.

Alternatively, one or more linker molecules connect the two portions of the fusion protein. The linker molecule allows the two portions of the fusion protein increased stearic freedom. In one embodiment, the linkers are peptide linkers. Peptides for linking protein chains are known to the art (Huston et al., 1993, Immunotechnology, ed. by J. Gosling et al., 47-60; Huston et al., Molecular Design and Modeling: Concepts and Applications, Part B, ed. J. J. Langone, Methods in Enzymology 203:46-88; Chaudhary et al, 1989, Nature 339:394-397). For example, a DNA construct may be prepared by recombinant methods or by polymerase chain reaction.

Figure 3A:
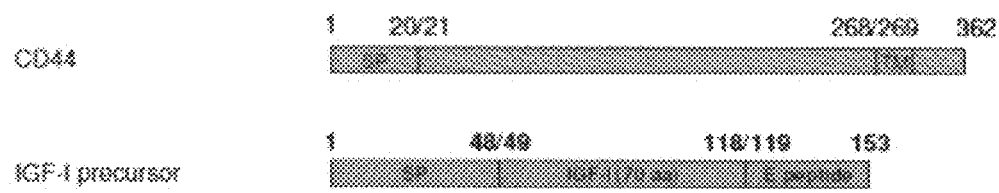
FIGS. 3A-3C. Schematic illustration of human HA receptor CD44 and human IGF-I (FIG. 3A), CD44(178)-IGF-I fusion protein (FIG. 3B) and CD44(178)-IGF-I fusion protein with linker (FIG. 3C).
Figure 3B:
Figure 3C:

Examples of linkers include, for example, the linkers of FIG. 3C. Linker 1: GGSG; Linker 2: GGSGGGSG; Linker 3: GGSGGGSGGGSG; Linker 4: GGGGS; Linker 5: GGGGSGGGGS; Linker 6: GGGGSGGGGSGGGGS; Linker 7: GGSGGS; and Linker 8: VIGHPIDSE (SEQ ID NOS 1-8, respectively, in order of appearance).

The DNA construct sequentially, 5' to 3', encodes a first part of a fusion protein, then a peptide linker region, followed by a second part of a fusion protein as a single open reading frame, flanked by regulatory elements suitable for expressing the encoded fusion protein in a host cell. The peptide linker according to the invention may optionally include serine, glycine or other residues that will act as "molecular hinges" to allow greater stearic freedom.

The peptide linker may be encoded by the chimeric nucleic acid molecule, protein parts may be prepared separately and the fusion protein assembled by peptide chemical methods.

In another alternative, the linker molecule may be comprised of peptide and non-peptide polymers or may be exclusively non-peptide in composition. A wide variety of organic linkers are known in the art. For example, polyalkane polymers (e.g., —$(CH_2)_n$—) may be readily linked by well known methods to thiol groups on sulfhydral containing amino acids.

Vectors and Promoters

The present invention further relates to vectors expressing the fusion proteins according to the invention. The vectors may be selected from any suitable vectors for inserting nucleic acid molecules into human host cells. The vectors may be deoxyribonucleic acid) ("DNA") vectors such as plasmids, adenovirus or even naked DNA inserted directly into cells to be treated by art known methods. The vectors may also be ribonucleic acid ("RNA") vectors, such as safe strains of the retroviruses.

Methods for the insertion of nucleic acid molecular fragments into a vector, as described, for example, in Maniatis, T., Fritsch, E. F., and Sambrook, J. (1989): Molecular Cloning (A Laboratory Manual), Cold Spring Harbor Laboratory, Cold Spring Harbor, N.Y.; and Ausubel, F. M., Brent, R., Kingston, R. E., Moore, D. D., Seidman, J. G., Smith, J. A., and Struhl, K. (1992): Current Protocols in Molecular Biology, John Wiley & Sons, New York, may be used to construct fusion protein-encoding expression vectors consisting of appropriate transcriptional/translational control signals. These methods may include in vitro DNA recombinant and synthetic techniques and in vivo genetic recombination. Expression of a nucleic acid sequence encoding the fusion proteins may be regulated by a second nucleic acid sequence so that the fusion protein is expressed in a host infected or transfected with the recombinant chimeric nucleic acid molecule. For example, expression of the fusion proteins may be controlled by a selected promoter/enhancer element. The promoter activation may be tissue specific or inducible by a metabolic product or administered substance.

Promoters/enhancers which may be used to control the fusion protein gene expression include, but are not limited to, the native IGF-1 or EGF promoter, the cytomegalovirus (CMV) promoter/enhancer (Karasuyama, H., et al., 1989, J. Exp. Med., 169:13), the human β-actin promoter (Gunning, et al., 1987, Proc. Natl. Acad. Sci. USA, 84:4831-4835), the glucocorticoid-inducible promoter present in the mouse mammary tumor virus long terminal repeat (MMTV LTR) (Klessig, D. F., et al., 1984, Mol. Cell Biol., 4:1354-1362), the long terminal repeat sequences of Moloney murine leukemia virus (MuLV LTR) (Weiss, R., et al., 1985, RNA Tumor Viruses, Cold Spring Harbor Laboratory, Cold Spring Harbor, N.Y.), the SV40 early region promoter (Bernoist and Chambon, 1981, Nature 290:304-310), the promoter contained in the 3' long terminal repeat of Rous sarcoma virus (RSV) (Yamamoto et al., 1980, Cell 22:787-797), the herpes simplex virus (HSV) thymidine kinase promoter/enhancer (Wagner et al., 1981, Proc. Natl. Acad. Sci. U.S.A. 78:1441-1445), the regulatory sequences of the metallothionein gene (Brinster et al., 1982, Nature 296:39-42), the adenovirus promoter (Yamada et al., 1985, Proc. Natl. Acad. Sci. U.S.A. 82(11):3567-71), and the herpes simplex virus LAT promoter (Wolfe, J. H., et al., 1992, Nature Genetics, 1:379-384).

Expression vectors compatible with mammalian host cells for use in genetic therapy of cells, include, but are not limited to: plasmids, retroviral vectors, adenovirus vectors, herpes viral vectors, poxvirus vectors and non-replicative avipox viruses, as disclosed, for example, by U.S. Pat. No. 5,174,993. The viral vectors may be suitably modified for safety and modified to be non-replicative in human host cells.

Assays for Chondrocyte-Stimulating Activity

The effectiveness of the fusion proteins herein may be ascertained according to the present examples.

Treatment Methods

The present invention is also directed to methods of ameliorating joint and chondrocyte-associated maladies in any mammal, including laboratory animals, companion animals, draft animals, meat animals, and humans. For instance, the present invention may be used to treat joint disease, injury (surgical or accident), pain, structural defects, or to increase sports performance. In particular, dogs, cats, horses, and humans would be treatable with the compositions and methods of the present invention. Methods of treatment include the direct introduction of the chimeric nucleic acid into the cells of the subject to be treated. Proteins may be introduced to the subject directly.

Alternatively, the methods of treatment include the ex vivo treatment of cells, e.g., chondrocytes that have been removed from a subject's body, followed by the reintroduction of the treated cells into the subject. The ex vivo treatment can be conducted with the fusion protein according to the invention, in order to affect the IGF-1 functionality in the treated tissue. In addition, the ex vivo treatment can be conducted with the chimeric nucleic acid molecules according to the invention, in order that the reintroduced cells will continue to affect IGF-1 functionality after reintroduction.

In another embodiment, vectors according to the invention can be applied to the skin and internal organs by suspension in appropriate physiological carriers.

For example, a physiologically appropriate solution containing an effective concentration of active vectors can be administered topically, interarticularly, intraocularly, parenterally, orally, intranasally, intravenously, intramuscularly, subcutaneously or by any other effective means. In particular, the vector may be directly injected into a target tissue by a needle in amounts effective to treat the cells of the target tissue. Alternatively, a body cavity or tissue can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the afflicted tissue. Any effective imaging device such as X-ray, sonogram, or fiberoptic visualization system may be used to locate the target area and guide the needle or other administration device.

In another alternative, a physiologically appropriate solution containing an effective concentration of active vectors can be administered systemically into the blood circulation to treat cells or tissues which cannot be directly reached or anatomically isolated.

In yet another alternative, target cells can be treated by introducing a fusion protein according to the invention into the cells. For example, liposomes are artificial membrane vesicles that are available to deliver drugs, proteins, and plasmid vectors both in vitro or in vivo (Mannino, R. J. et al., 1988, Biotechniques, 6:682-690) into target cells (Newton and Huestis, Biochemistry, 1988, 27: 4655-4659; Tanswell, A. K. et al., 1990, Biochemica et Biophysica Acta, 1044:269-274; and Ceccoll, J. et al. Journal of Investigative Dermatology, 1989, 93:190-194). Thus, fusion protein can be encapsulated at high efficiency with liposome vesicles and delivered into mammalian cells in vitro or in vivo.

Liposome-encapsulated fusion protein may be administered topically, intraocularly, parenterally, intranasally, intratracheally, intrabronchially, intramuscularly, subcutaneously or by any other effective means at a dose efficacious to treat the injured tissue or abnormal cells of the target. The liposomes may be administered in any physiologically appropriate composition containing an effective concentration of encapsulated fusion protein.

An effective concentration of vector or fusion protein may be determined by the ordinary artisan, for example, by screening chimeric nucleic acid vectors encoding fusion protein, or a fusion protein, in a chondrocyte assay system as described herein.

cDNA constructs encoding the present fusion proteins are described in the examples. The human IGF-1 cDNA sequence, including the coding sequence for the mature peptide, with and without the E-peptide were linked to the cDNA sequence encoding the hyaluronic acid-binding domain of cartilage matrix protein (HAB) with and without additional upstream cDNA sequences. When these gene sequences are placed into a vector and transferred into articular chondrocytes, the fusion protein is produced by the cells. The fusion protein is designed to bind to the hyaluronic acid-like molecules present in the tissue matrix that surrounds articular chondrocytes in vivo and during culture in vitro. Because this binding is reversible, the IGF-1 will be released over time. The significance of this approach is that it achieves local IGF-1 delivery over time in the presence of a responsive cell population.

The gene sequences, when expressed by chondrocytes, produce fusion proteins with superior IGF-1 attributes. When the fusion protein is secreted from the chondrocytes, the secreted fusion protein acts upon the cells that produced it and neighboring cells to stimulate cell division, the production of new matrix, and to inhibit cartilage degradation. The compositions are preferably administered locally, preferably by an instrument of injecting liquids into a joint cavity according to conventional methods. In one embodiment of the present method, the solution is directly injected via a syringe needle into the joint space (including connective tissue and synovial) of the patient. The size of the syringe needle is determined by the health professional administering the solution and the amount of solution to be injected into joint space of the patient. Preferably, the syringe is capable of containing at least 0.1 cc of liquid and administering the liquid percutaneously into the joint space of the patient via a syringe needle.

The typical volumes of solution injected into joint space of the patient ranges from 0.1 cc to 10 cc of solution per administration, depending on the size of the joint being treated. Preferably, the solution volume is ranges between 0.5 cc to 5 cc of solution and most preferably, the volume is 1 cc to 5 cc of solution.

The treatment may optionally include administration of an anesthetic/anti-inflammatory component of the solution dosage typically comprises at least one anesthetic that preferably has a volume that is between 20% to 60% of the total solution volume of each solution dosage. The anti-inflammatory component of the solution dosage may optionally comprise corticosteroids, including, optionally, two corticosteroids, each corticosteroid preferably having a volume that is between 10% to 50% of the total solution volume of each solution dosage.

The anesthetic component of the solution of the present method is selected based on the desired duration of pain relief provided to the painful (arthritic) or connective tissue target of the patient. Exemplary anesthetic compounds include procaine hydrochloride ("Procaine").

The corticosteroids components are selected from the group consisting of Betamethasone, Methylprednisolone acetate ("Depomedrol"), Cortisone acetate, Dexamethasone, Hydrocortisone, Methylprednisolone, Prednisolone, Prednisolone sodium phosphate, and Prednisone. In one embodiment of the present method corticosteroids component includes a mixture of Dexamethasone and Depomedrol. In one embodiment of the method the anesthetic is buffered.

The needle of the syringe needle of the present method is selected based on the size of the joint space of the patient. In one embodiment of the present method the needle is a hypodermic needle, preferably an arthroscopic needle, but may be other types of needles depending on the application including non-arthroscopic needles. Preferably, the present method provides for needle gauges in the range of between 22 and 25 gauge and from ¾ inch to 1½ inches in length.

Further, the treatment solution is injected into the joint. Preferably, this is done by inserting the syringe needle through the treated topical skin area and then slowly guiding the needle of the syringe needle into the synovia capsule of the target joint. Depending upon the joint or target space capacity, preferably 10 ml or less of the present treatment composition is introduced slowly into the joint capsule.

Further, the treatment may be repeated periodically. Repeat injections may be administered in 1, 5, 7, 10, 20, 30 day or yearly intervals after the first injection. The solution can be mixed in a separate container prior to be loaded into a syringe or they can be mixed in the syringe directly prior to administration.

Example 2. Creation of Hyaluronic Acid Binding—Insulin-Like Growth Factor I Fusion Protein cDNA Constructs Three cDNAs were created, encoding three hyaluronic acid-binding domain (HAB)—insulin-like growth factor I (IGF-I) fusion proteins (HAB-IGF-I) by coupling the sequence encoding IGF-I with those encoding a hyaluronic acid binding region derived from three cartilage matrix proteins. These regions include 1) the aggrecan G1 domain (AG1), 2) the versican G1 domain (VG1) and 3) link protein (LP). The resulting fusion proteins are designated AG1-IGF-I, VG1-IGF-I, and LP-IGF-I respectively (FIG. 1B). Further, the encoded fusion proteins were created by transferring the cDNAs into producer cells and the selected therapeutic target cells, articular chondrocytes.

To facilitate the HAB-IGF-I constructs to be used for human therapeutic purposes, the DNA constructs encoding all the HAB-IGF-I fusion proteins were generated from native human matrix protein gene sequences and the native human IGF-I gene sequence (Accession number: X57025) and were designed to include signal peptides.

All the constructs described and illustrated in FIG. 1B were created using specifically designed primers by polymerase chain reaction (Table 4).

Figure 1B:
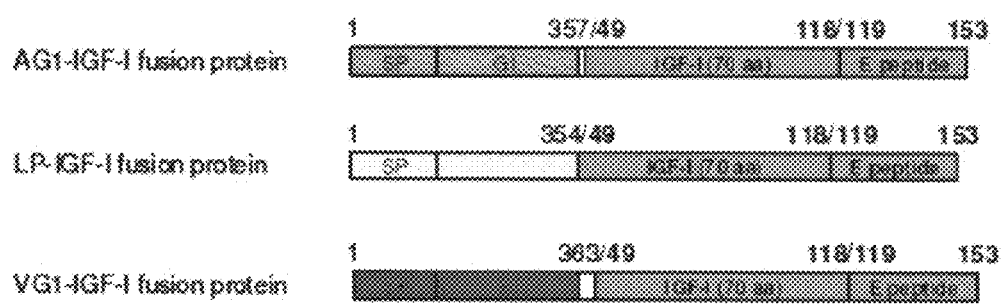
Figure 2A:
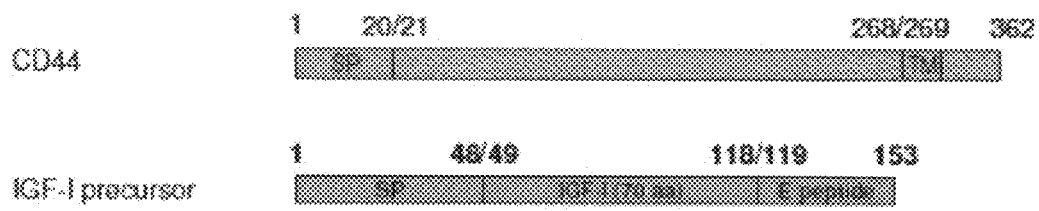
FIGS. 2A-2B. Schematic illustration of human HA receptor CD44 and human IGF-I (FIG. 2A), and CD44-IGF-I fusion proteins (FIG. 2B).
Figure 2B:
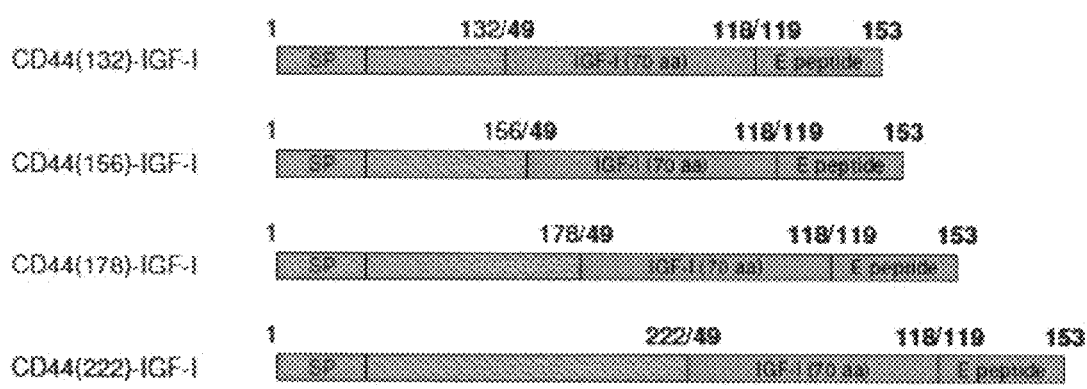

As shown in FIG. 1A, Aggrecan has two globular structural domains (G1 and G2) near the N-terminal end and one globular domain (G3) at the C-terminal end, separated by a large extended domain modified with glycosaminoglycans. The two main modifier moieties are arranged into distinct regions, a chondroitin sulfate (CS) and a keratan sulfate (KS) region.

Example 3. Production of Fusion Proteins and Demonstration of Fusion Protein Integrity To promote articular cartilage preservation or repair using these fusion proteins as therapeutic agents, it is necessary to have a production source for the proteins. A method of production employs the fusion protein-encoding cDNAs described above and a non-viral (plasmid) vector that the inventors developed previously, Shi et al., *Effect of Transfection Strategy on Growth Factor Overexpression by Articular Chondrocytes*, J. of Orthopaedic Research, January 2010, hereby incorporated by reference. The cDNAs were inserted into the vector and used to transfect HEK 293 cells (Stratagene). The HEK 293 cells then use these inserted transgenes to synthesize the HAB-IGF-I fusion proteins. On day 3 after transfection conditioned medium was collected for measurement of HAB-IGF-I fusion proteins produced as transgene products by the HEK 293 cells. The production and integrity of these proteins was confirmed by IGF-I ELISA (R&D Systems) and a HA-binding functional ELISA.

It was found that pAAV-VG-IGF-I transfected cells produced a high level of IGF-I (1939 ng/ml), pAAV-AG1-IGF-I transfected cells produced 865 ng/ml of IGF-I, and pAAV-LP-IGF-I transfected cells only produced 5 ng/ml of IGF-I. HA-binding functional ELISA data demonstrated that the VG-IGF-I and the AG1-IGF-I fusion proteins successfully attached to hyaluronic acid, and AG1 or VG1 and IGF-I are linked together.

Example 4. Demonstration of Bioactivity of Transferred HAB-IGF-I Genes in Articular Chondrocytes To promote articular cartilage preservation or repair using the fusion protein cDNAs as agents for gene therapy, the transgenes must stimulate reparative activity by their host cells. To test this capability, primary bovine articular chondrocytes were transfected and cultured for 5 days. On day 5, the chondrocytes were collected and used to measure biosynthesis of cell-associated matrix molecules. An index of articular chondrocyte reparative activity is the production of glycosaminoglycan (GAG). GAG is an essential component of articular cartilage. It is produced by articular chondrocytes incorporated into their surrounding matrix.

Chondrocytes transfected with pAAV-VG1-IGF-I produced a high level of GAG (71.4±3.3 ug/well), pAAV-AG1-IGF-I transfected cells produced 65.5±0.3 ug/well of GAG, and pAAV-LP-IGF-I transfected cells produced 42.4±0.6 ug/well of GAG.

Example 5. CD44-IGF-I Constructs

Four different constructs of CD44-IGF-I were generated: 1) CD44(132)-IGF-I (SEQ ID NO: 64), 2) CD44(156)-IGF-I (SEQ ID NO: 68), 3) CD44(178)-IGF-I (SEQ ID NO: 72), and 4) CD44(222)-IGF-I (SEQ ID NO: 76). Each construct was separately delivered to bovine chondrocytes using a pAAV-based vector. The empty vector, pAAV-MCS, was used as a control. The conditioned medium was harvested on day 2 after transfection. The conditioned medium was analyzed by both IGF-I ELISA and HA-binding functional ELISA. Different constructs generated dramatically different production of CD44-IGF-I fusion protein in chondrocytes. Construct CD44(156)-IGF-I generated the least amount of fusion protein (13.50 ng/ml) while construct CD44(178)-IGF-I produced the highest amount of fusion protein (289.51 ng/ml), 21.4 fold higher than that of the construct CD44 (156)-IGF-I. HA-binding functional ELISA showed that the fusion protein from construct CD44(178)-IGF-I in chondrocytes binds to HA, and CD44(178) and IGF-I are linked together. HA-binding activity was not detectable in the conditioned medium from the chondrocytes transfected by construct CD44(132)-IGF-I, CD44(156)-IGF-I or CD44 (222)-IGF-I. Low production of CD44-IGF-I fusion protein in chondoocytes transfected by CD44(132)-IGF-I or CD44 (156)-IGF-I interfered with HA-binding activity detection in the condition medium (Table 1).

TABLE 1

Production and HA-binding activity of CD44-IGF-I fusion protein

|  | IGF-I (ng/ml) (IGF-I ELISA) | Arbitrary unit (HA-binding functional ELISA) |
| --- | --- | --- |
| Control | 0.00 | 0.00 |
| CD44(132)-IGF-I | 19.95 | 0.00 |
| CD44(156)-IGF-I | 13.50 | 0.00 |

TABLE 1-continued

Production and HA-binding activity of CD44-IGF-I fusion protein

|  | IGF-I (ng/ml) (IGF-I ELISA) | Arbitrary unit (HA-binding functional ELISA) |
| --- | --- | --- |
| CD44(178)-IGF-I | 289.51 | 1.70 |
| CD44(222)-IGF-I | 172.91 | 0.00 |

To improve the HA-binding activity of CD44(178)-IGF-I, nine different constructs were generated, each containing a different linker between CD44(178) and IGF-I, using pAAV-CD44(178)-IGF-I as a template and QuickChange Lighting Site-Directed Mutagenesis Kit (Stratagene). Each construct was separately delivered to bovine chondrocytes using a pAAV vector. The original construct, CD44(178)-IGF-I, in the pAAV vector was included for comparison. The conditioned medium was harvested on day 2 after transfection. The conditioned medium was analyzed by both IGF-I ELISA and HA-binding functional ELISA. Different linkers have varied effects on the fusion protein production and HA-binding activity. Compared to the original construct, CD44(178)-IGF-I, the insertion of Linker 8 increases the fusion protein production and HA-binding activity by 1.7 fold and 2.9 fold respectively (Table 2).

TABLE 2

Production and HA-binding activity of CD44-IGF-I fusion protein with or without a linker

|  | IGF-I (ng/ml) (IGF-I ELISA) | Arbitrary unit (HA-binding functional ELISA) |
| --- | --- | --- |
| CD44(178)-IGF-I | 278.77 | 1.56 |
| CD44(178)-Linker 1-IGF-I | 278.20 | 0.77 |
| CD44(178)-Linker 2-IGF-I | 236.56 | 0.99 |
| CD44(178)-Linker 3-IGF-I | 144.40 | 0.33 |
| CD44(178)-Linker 4-IGF-I | 271.98 | 1.11 |
| CD44(178)-Linker 5-IGF-I | 267.40 | 0.21 |
| CD44(178)-Linker 6-IGF-I | 240.64 | 0.40 |
| CD44(178)-Linker 7-IGF-I | 343.39 | 0.30 |
| CD44(178)-Linker 8-IGF-I | 463.64 | 4.47 |

Example 6. Protease Cleavage Site Constructs

Constructs were generated, each containing a different specific protease cleavage site between VG1 and IGF-I, using pAAV-VG1-IGF-I as a template and QuickChange Lighting Site-Directed Mutagenesis Kit (Stratagene). The resulting constructs and the original construct were delivered to bovine chondrocytes using a pAAV-based vector. The conditioned medium was harvested on day 2 after transfection. The conditioned medium was analyzed by IGF-I ELISA and HA-binding functional ELISA respectively. The constructs with a protease cleavage site generated similar amounts of fusion protein and the resulting fusion proteins had similar HA-binding activity (Table 3), compared with the original construct VG1-IGF-I (Table 1). These VG1 fusion proteins with protease cleavage site are assessed to examine specific proteases cleavage efficiency and to measure the activity of the released growth factor. This method can be applied to aggrecan, CD44, and other HA-binding domains, and other growth factors.

TABLE 3

Production and HA-binding activity of CD44-IGF-I fusion protein

| | IGF-I (ng/ml) (IGF-I ELISA) | Arbitrary unit (HA binding functional ELISA) |
|---|---|---|
| Control | 0.00 | 0.00 |
| VG1-I1 | 299.03 | 199.26 |
| VG1-EK-IGF-I | 358.97 | 249.86 |
| VG1-Furin-IGF-I | 221.79 | 228.85 |
| VG1-Xa-IGF-I | 312.21 | 256.90 |

Figure 4A:
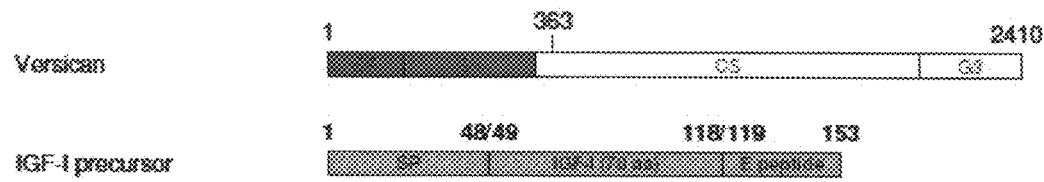
FIGS. 4A-4C. Schematic illustration of human versican and human IGF-I (FIG. 4A), VG1-IGF-I fusion protein (FIG. 4B) and VG1-IGF-I fusion proteins with a cleavage site (FIG. 4C).
Figure 4B:
Figure 4C:
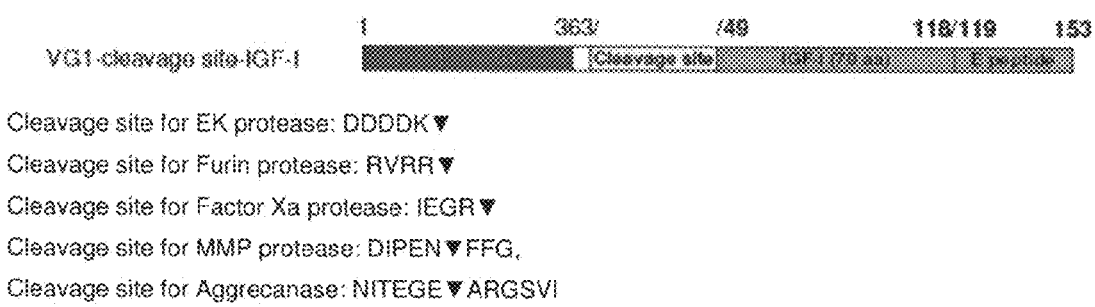

A depiction of a fusion protein with a cleavage site is shown in FIG. 4C. Examples of cleavage sites include: cleavage site for EK protease: DDDDK ▼ (SEQ ID NO: 9); cleavage site for Furin protease: RVRR ▼ (SEQ ID NO: 10); cleavage site for Factor Xa protease: IEGR ▼ (SEQ ID NO: 11); cleavage site for MMP protease: DIPEN ▼ FFG (SEQ ID NO: 12); and cleavage site for Aggrecanase: NITEGE ▼ ARGSVI (SEQ ID NO: 13).

Example 7. Sequences

Specific nucleotide and amino acid sequences may be utilized in embodiments of the invention.

Examples of primers useful for building HAB-IGF-I fusion protein constructs are provided in Table 4.

TABLE 4

Primers for building HAB-IGF-I fusion protein constructs

| Primer | Sequence | SEQ ID No. |
|---|---|---|
| AG1 F | 5'-GAATTCACCATGGCCACTTTACTCTGGGTTT TCGTGACTC-3' | 14 |
| AG1 R | 5'-GGGCCCGATGTCCACAAAGTCTTCACCTGTG TAG-3' | 15 |
| LP F | 5'-GAATTCACCATGGAGAGTCTACTTCTTCTGG TGCTGATTTC-3' | 16 |
| LP R | 5'-GGGCCCGTTGTATGCTCTGAAGCAGTAGACA CC-3' | 17 |
| VG1 F | 5'-GAATTCACCATGGTCATAAATATAAAGAGCA TCTTATGGA-3' | 18 |
| VG1 R | 5'-GTCGACCAATTGGATGACCAATTACACTCAA ATCACTC-3' | 19 |
| IGF-I F1 | 5'-GTCGACGGGCCCGAGACGCTCTGCGGGCTG AGCTGGTG-3' | 20 |
| IGF-I F2 | 5'-CAATTGATTCAGAAGGACCGGAGACGCTCTG CGGGGCTGAG-3' | 21 |
| IGF-I R | 5'-CTCGAGCTACATCCTGTAGTTCTTGTTTCCT G-3' | 22 |
| IGF-I F3 | 5'-GAATTCACAATGGGAAAAATCAGCAGTCTTC C-3' | 23 |

The underlined 6-bp sequence represents EcoR I (GAATTC), Xho I (CTCGAG), Mfe I(CAATTG), BamH I (GGATCC) or Apa I (GGGCCC) sites. Sal I (GTCGAC) site in primer VG1R and IGF-I F1I is included for cloning.

Human aggrecan gene nucleotide sequence is provided (SEQ ID No. 24) and the human aggrecan gene nucleotide sequence segment encoding the N-terminal 357 aa of human aggrecan (SEQ ID No. 25), which includes aggrecan G1 domain and a partial IGD domain (FIG. 1A). The aggrecan G1 domain (AG1) is responsible for the binding of aggrecan to hyaluronic acid.

Human aggrecan protein amino acid sequence is provided (SEQ ID No. 26) and the N-terminal 357 aa of human aggrecan (SEQ ID No. 27), which includes aggrecan G1 domain and a partial IGD domain (FIG. 1A). The aggrecan G1 domain (AG1) is responsible for the binding of aggrecan to hyaluronic acid.

Human link protein gene nucleotide sequence is provided (SEQ ID No. 28). Link protein (LP) binds to hyaluronic acid and aggrecan G1 domain (AG1) in stabilizing the interaction between aggrecan and hyaluronan to form aggrecan aggregates in articular cartilage.

Human link protein amino acid sequence is provided (SEQ ID No. 29).

Human versican gene nucleotide sequence is provided (SEQ ID No. 30) and the N-terminal 363 aa of human versican (SEQ ID No. 31), which includes versican G1 domain (FIG. 1A). The versican G1 domain (VG1) is responsible for the binding of versican to hyaluronic acid.

Human versican protein amino acid sequence is provided (SEQ ID No. 32) and the N-terminal 363 aa of human versican (SEQ ID No. 33), which includes versican G1 domain (FIG. 1A). The versican G1 domain (VG1) is responsible for the binding of versican to hyaluronic acid.

Human IGF-I (signal peptide and mature peptide and E peptide) gene nucleotide sequence is provided (SEQ ID No. 34). The 70aa gene nucleotide sequence encoding the IGF-I mature peptide (SEQ ID No. 35) is provided. The 48aa gene nucleotide sequence encoding the IGF-I signal peptide (SEQ ID No. 36) is provided. The 35aa gene nucleotide sequence encoding the IGF-I E peptide (SEQ ID No. 37) is also provided (FIG. 1A).

Human IGF-I (signal peptide and mature peptide and E peptide) protein amino acid sequence is provided (SEQ ID No. 38). The amino acid sequence (70aa) encoding the IGF-I mature peptide (SEQ ID No. 39) is provided. The amino acid sequence (48aa) encoding the IGF-I signal peptide (SEQ ID No. 40) is provided. The amino acid sequence (35aa) encoding the IGF-I E peptide (SEQ ID No. 41) is also provided (FIG. 1A).

HAB-IGF-I Fusion Protein

AG1-IGF-I fusion protein (FIG. 1B) nucleotide sequence is provided (SEQ ID No. 42). A segment of the AG1-IGF-I fusion protein nucleotide sequence encodes IGF-I mature peptide and E peptide (SEQ ID No. 43). This is fused to a c-terminal truncated aggrecan from AA 1 to AA 357, which includes aggrecan G1 domain (AG1) and a partial IGD domain. The aggrecan G1 domain (AG1) is responsible for the binding of aggrecan to hyaluronic acid.

AG1-IGF-I fusion protein (FIG. 1B) amino acid sequence is provided (SEQ ID No. 44). A segment of the AG1-IGF-I fusion protein amino acid sequence is IGF-I mature peptide and E peptide (SEQ ID No. 45). This is fused to a c-terminal truncated aggrecan from AA 1 to AA 357, which includes aggrecan G1 domain (AG1) and a partial IGD domain. The aggrecan G1 domain (AG1) is responsible for the binding of aggrecan to hyaluronic acid.

LP-IGF-I fusion protein (FIG. 1B) nucleotide sequence is provided (SEQ ID No. 46). A segment of the LP-IGF-I fusion protein nucleotide sequence encodes IGF-I mature peptide and E peptide (SEQ ID No. 47). This is fused to human link protein at c-terminal. Link protein (LP) binds to hyaluronic acid and aggrecan G1 domain (AG1) in stabilizing the interaction between aggrecan and hyaluronan to form aggrecan aggregates in articular cartilage.

LP-I1 (FIG. 1B) amino acid sequence is provided (SEQ ID No. 48). A segment of the LP-I1 amino acid sequence is IGF-I mature peptide and E peptide (SEQ ID No. 49). This is fused to human link protein at c-terminal. Link protein (LP) binds to hyaluronic acid and aggrecan G1 domain (AG1) in stabilizing the interaction between aggrecan and hyaluronan to form aggrecan aggregates in articular cartilage.

VG1-I1 (FIG. 1B) nucleotide sequence is provided (SEQ ID No. 50). A segment of the VG1-I1 nucleotide sequence encodes IGF-I mature peptide and E peptide (SEQ ID No. 51). This is fused to a c-terminal truncated versican from AA 1 to AA 363, which includes versican G1 domain (VG1). The versican G1 domain (VG1) is responsible for the binding of versican to hyaluronic acid.

VG1-I1 (FIG. 1B) amino acid sequence is provided (SEQ ID No. 52). A segment of the VG1-I1 sequence is IGF-I mature peptide and E peptide (SEQ ID No. 53). This is fused to a c-terminal truncated versican from AA 1 to AA 363, which includes versican G1 domain (VG1). The versican G1 domain (VG1) is responsible for the binding of versican to hyaluronic acid.

Human CD44 gene nucleotide sequence is provided (SEQ ID No. 54). The protein encoded by this gene sequence is a cell-surface glycoprotein. It is a receptor for hyaluronic acid (HA). This sequence (NM_0010013931) is one of CD44 mRNA splicing variants. The 5'-804 nt sequence (SEQ ID No. 55) encodes the N-terminal 268 aa of CD44: a signal peptide (SP) from AA1 to AA20 and an extracellular region from AA21 to AA268. The extracellular region from AA21 to AA268 contains the HA binding domain, which is responsible for the binding of CD44 to HA. The 60 nt sequence after the 804 nt sequence encodes the 20 aa of human CD44 transmembrane region (TM) (SEQ ID No. 56). The 3'-222 nt sequence encodes the 73 aa of the C-terminal intracellular region of CD44 (SEQ ID No. 57).

Human CD44 protein amino acid sequence is provided (SEQ ID No. 58). The N-terminal 268 aa sequence (SEQ ID No. 59) consists of a signal peptide (SP) from AA1 to AA20 and an extracellular region from AA21 to AA268. The CD44 extracellular region from AA21 to AA268 contains the HA-binding domain responsible for the binding of CD44 to HA. The C-terminal 73 aa sequence (SEQ ID No. 61) is the intracellular region of CD44. The 20 aa sequence between them is CD44 transmembrane region (TM) (SEQ ID No. 60) (FIG. 4A).

CD44-IGF-I Fusion Protein

CD44(132)-IGF-I nucleotide sequence is provided (SEQ ID No. 62). A segment of the CD44(132)-IGF-I nucleotide sequence (SEQ ID No. 63) encodes IGF-I mature peptide and E peptide. This is fused to a c-terminal truncated CD44 from AA 1 to AA 132 (FIG. 4B).

CD44(132)-IGF-I amino acid sequence is provided (SEQ ID No. 64). A segment of the CD44(132)-IGF-I amino acid sequence is IGF-I mature peptide and E peptide (SEQ ID No. 65). This is fused to a c-terminal truncated CD44 from AA 1 to AA 132 (FIG. 4B).

CD44(156)-IGF-I nucleotide sequence is provided (SEQ ID No. 66). A segment of the CD44(156)-IGF-I nucleotide sequence encodes IGF-I mature peptide and E peptide (SEQ ID No. 67). This is fused to a c-terminal truncated CD44 from AA 1 to AA 156 (FIG. 4B).

CD44(156)-IGF-I amino acid sequence is provided (SEQ ID No. 68). A segment of the CD44(156)-IGF-I amino acid sequence (SEQ ID No. 69) is IGF-I mature peptide and E peptide. This is fused to a c-terminal truncated CD44 from AA 1 to AA 156 (FIG. 4B).

CD44(178)-IGF-I nucleotide sequence is provided (SEQ ID No. 70). A segment of the CD44(178)-IGF-I nucleotide sequence encodes IGF-I mature peptide and E peptide (SEQ ID No. 71). This is fused to a c-terminal truncated CD44 from AA 1 to AA 178 (FIG. 4B).

CD44(178)-IGF-I amino acid sequence is provided (SEQ ID No. 72). A segment of the CD44(178)-IGF-I amino acid sequence encodes IGF-I mature peptide and E peptide (SEQ ID No. 73). This is fused to a c-terminal truncated CD44 from AA 1 to AA 178 (FIG. 4B).

CD44(222)-IGF-I nucleotide sequence is provided (SEQ ID No. 74). A segment of the CD44(222)-IGF-I nucleotide sequence encodes IGF-I mature peptide and E peptide (SEQ ID No. 75). This is fused to a c-terminal truncated CD44 from AA 1 to AA 222 (FIG. 4B).

CD44(222)-IGF-I amino acid sequence is provided (SEQ ID No. 76). A segment of the CD44(222)-IGF-I amino acid sequence is IGF-I mature peptide and E peptide (SEQ ID No. 77). This is fused to a c-terminal truncated CD44 from AA 1 to AA 222 (FIG. 4B).

Sequence Listing Table

| SEQ ID NO | Abbreviation (as applicable) | Name |
| --- | --- | --- |
| 1 | Linker | Linker 1 |
| 2 | Linker | Linker 2 |
| 3 | Linker | Linker 3 |
| 4 | Linker | Linker 4 |
| 5 | Linker | Linker 5 |
| 6 | Linker | Linker 6 |
| 7 | Linker | Linker 7 |
| 8 | Linker | Linker 8 |
| 9 | Cleavage site | cleavage site for EK protease |
| 10 | Cleavage site | cleavage site for Furin protease |
| 11 | Cleavage site | cleavage site for Factor Xa protease |
| 12 | Cleavage site | cleavage site for MMP protease |
| 13 | Cleavage site | cleavage site for Aggrecanase |
| 14 | AG1 F | Primer: Aggrecan G1 domain (forward) |
| 15 | AG1 R | Primer: Aggrecan G1 domain (reverse) |
| 16 | LP F | Primer: Link Protein (forward) |
| 17 | LP R | Primer: Link Protein (reverse) |
| 18 | VG1 F | Primer: Versican G1 domain (forward) |
| 19 | VG1 R | Primer: Versican G1 domain (reverse) |
| 20 | IGF-I F1 | Primer: insulin-like growth factor (forward) |
| 21 | IGF-I F2 | Primer: insulin-like growth factor (forward) |
| 22 | IGF-I R | Primer: insulin-like growth factor (reverse) |
| 23 | IGF-I F3 | Primer: insulin-like growth factor (forward) |
| 24 | Aggrecan | Human aggrecan gene nucleotide sequence |
| 25 | | nucleotide sequence N terminal 357 aa of human aggrecan - includes aggrecan G1 domain (AG1) and a partial IGD domain |
| 26 | Aggrecan | Human aggrecan protein amino acid sequence |
| 27 | | amino acid sequence N-terminal 357 aa of human aggrecan |
| 28 | LP | Human link protein gene nucleotide sequence |
| 29 | LP | Human link protein amino acid sequence |
| 30 | Versican | Human versican gene nucleotide sequence |
| 31 | | nucleotide sequence N- |

Sequence Listing Table

| SEQ ID NO | Abbreviation (as applicable) | Name |
|---|---|---|
| 32 | Versican | terminal 363 aa of human versican - includes versican G1 domain (VG1) Human versican protein amino acid sequence |
| 33 | | amino acid sequence N-terminal 363 aa of human versican - includes versican G1 domain (VG1) |
| 34 | | Human IGF-I (signal peptide and mature peptide and E peptide) gene nucleotide sequence |
| 35 | IGF-I (70aa) | IGF-I mature peptide nucleotide sequence |
| 36 | SP | IGF-I signal peptide nucleotide sequence |
| 37 | E peptide | IGF-I E nucleotide sequence |
| 38 | | Human IGF-I (signal peptide, mature peptide, and E peptide) amino acid sequence |
| 39 | IGF-I (70aa) | IGF-I mature peptide amino acid sequence |
| 40 | SP | IGF-I signal peptide amino acid sequence |
| 41 | E peptide | IGF-I E peptide amino acid sequence |
| 42 | | AG1-IGF-I fusion protein nucleotide sequence |
| 43 | | segment of the AG1-IGF-I fusion protein nucleotide sequence encoding IGF-I mature peptide and E peptide |
| 44 | | AG1-IGF-I fusion protein amino acid sequence |
| 45 | | segment of the AG1-IGF-I fusion protein amino acid sequence: IGF-I mature peptide and E peptide |
| 46 | | LP-IGF-I fusion protein nucleotide sequence |
| 47 | | segment of the LP-IGF-I fusion protein nucleotide sequence encoding IGF-I mature peptide and E peptide |
| 48 | | LP-I1 amino acid sequence |
| 49 | | segment of the LP-I1 amino acid sequence: IGF-I mature peptide and E peptide |
| 50 | | VG1-IGF-1 nucleotide sequence |
| 51 | | segment of the VG1-IGF-1 nucleotide sequence encoding IGF-I mature peptide and E peptide |
| 52 | | VG1-IGF-1 amino acid sequence |
| 53 | | segment of the VG1-IGF-1 nucleotide sequence: IGF-I mature peptide and E peptide |
| 54 | CD44 | Human CD44 gene nucleotide sequence |
| 55 | | N-terminal 268 aa of CD44 (including SP & HAB) |
| 56 | TM | human CD44 transmembrane region |
| 57 | | C-terminal intracellular region of CD44 |
| 58 | | Human CD44 protein amino acid sequence |
| 59 | | CD44 N-terminal 268 aa sequence consists of a signal peptide (SP) from AA1 to AA20 and an extracellular region from AA21 to AA268 |
| 60 | | CD44 transmembrane region |
| 61 | | C-terminal intracellular region of CD44 |
| 62 | | CD44(132)-IGF-I nucleotide sequence |
| 63 | | segment of the CD44(132)-IGF-I nucleotide sequence encoding IGF-I mature peptide and E peptide |
| 64 | | CD44(132)-IGF-I amino acid sequence |
| 65 | | segment of the CD44(132)-IGF-I amino acid sequence is IGF-I mature peptide and E peptide |
| 66 | | CD44(156)-IGF-I nucleotide sequence |
| 67 | | segment of the CD44(156)-IGF-I nucleotide sequence encodes IGF-I mature peptide and E peptide |
| 68 | | CD44(156)-IGF-I amino acid sequence |
| 69 | | segment of the CD44(156)-IGF-I amino acid sequence: IGF-I mature peptide and E peptide |
| 70 | | CD44(178)-IGF-I nucleotide sequence |
| 71 | | segment of the CD44(178)-IGF-I nucleotide sequence encoding IGF-I mature peptide and E peptide |
| 72 | | CD44(178)-IGF-I amino acid sequence |
| 73 | | segment of the CD44(178)-IGF-I amino acid sequence: IGF-I mature peptide and E peptide |
| 74 | | CD44(222)-IGF-I nucleotide sequence |
| 75 | | segment of the CD44(222)-IGF-I nucleotide sequence encoding IGF-I mature peptide and E peptide |
| 76 | | CD44(222)-IGF-I amino acid sequence |
| 77 | | segment of the CD44(222)-IGF-I amino acid sequence: IGF-I mature peptide and E peptide |

The terms and expressions which have been employed are used as terms of description and not of limitation, and there is no intention in the use of such terms and expressions of excluding any equivalents of the features shown and described or portions thereof. Thus, it should be understood that although the present invention has been specifically disclosed by particular embodiments and optional features, modification and variation of the concepts herein disclosed may be used by those skilled in the art, and that such modifications and variations are considered to be within the scope of this invention as defined by the appended claims.

Whenever a range is given in the specification, all intermediate ranges and subranges, as well as all individual values included in the ranges given are intended to be included in the disclosure. When a Markush group or other grouping is used herein, all individual members of the group and all combinations and sub-combinations possible of the group are intended to be individually included in the disclosure.

While the present invention has been described in terms of those particular embodiments and examples, it will be appreciated that the spirit and scope of the invention is not limited to those embodiments, but extends to the various modifications and equivalents as defined in the appended claims.

We claim:

1. A fusion protein, comprising:
a hyaluronic acid-binding (HAB) polypeptide, wherein the HAB polypeptide is a polypeptide having the sequence of amino acids 1-178 of SEQ ID NO: 72; and
a conserved region of a growth factor (GF) protein,
wherein said fusion protein upregulates glycosaminoglycan (GAG) expression in chondrocytes.

2. The fusion protein of claim 1, further comprising at least one additional element selected from the group consisting of: a signal peptide (SP); a linker peptide (linker); a protease cleavage site; and an E peptide.

3. The fusion protein of claim 1, wherein the HAB polypeptide is linked to the amino (N)-terminus of the conserved region of the GF protein.

4. The fusion protein of claim 2, further comprising at least one of a linker peptide (linker) positioned between the HAB polypeptide and the conserved region of the GF protein and a protease cleavage site positioned between the HAB and the conserved region of the GF protein.

5. The fusion protein of claim 2, wherein the SP is selected from the group consisting of: aggrecan signal peptide; CD44 signal peptide; link protein signal peptide; TSG-6 signal peptide; and versican signal peptide.

6. The fusion protein of claim 2, wherein the linker is selected from the group consisting of: Linker 1: GGSG (SEQ ID NO: 1); Linker 2: GGSGGGSG (SEQ ID NO: 2); Linker 3: GGSGGGSGGGSG (SEQ ID NO: 3); Linker 4: GGGGS (SEQ ID NO: 4); Linker 5: GGGGSGGGGS (SEQ ID NO: 5); Linker 6: GGGGSGGGGSGGGGS (SEQ ID NO: 6); Linker 7: GGSGGS (SEQ ID NO: 7); and Linker 8: VIGHPIDSE (SEQ ID NO: 8).

7. The fusion protein of claim 2, wherein the protease cleavage site is selected from the group consisting of: SEQ ID NO: 9; SEQ ID NO: 10; SEQ ID NO: 11; SEQ ID NO: 12; and SEQ ID NO: 13.

8. The fusion protein of claim 1, wherein the GF protein is selected from the group consisting of: IGF-1; BMP2; BMP4; BMP7; FGF2; FGF18; GDF5; TGF-β1; and TGF-β3.

9. The fusion protein of claim 1, further comprising: flanking amino acids to the HAB polypeptide, wherein the number of flanking amino acids is selected from the group consisting of: 5 amino acids; 10 amino acids; 15 amino acids; 20 amino acids; 25 amino acids; 30 amino acids; 35 amino acids; 40 amino acids; 45 amino acids; 50 amino acids; 55 amino acids; and 60 amino acids.

10. The fusion protein of claim 9, wherein the flanking amino acids are at the N terminus of HAB polypeptide.

11. The fusion protein of claim 9, wherein the flanking amino acids are at the C terminus of HAB polypeptide.

12. A nucleic acid molecule comprising a nucleic acid sequence that encodes the fusion protein of claim 1.

13. The nucleic acid molecule of claim 12, wherein the nucleic acid molecule further comprises at least one additional nucleic acid sequence, wherein the additional nucleic acid sequence is selected from the group consisting of: a nucleic acid sequence that encodes at least one signal peptide (SP); a nucleic acid sequence that encodes at least one linker sequence (linker); a nucleic acid sequence that encodes at least one protease cleavage site; a nucleic acid sequence that encodes at least one E peptide; and a nucleic acid sequence that encodes at least one additional functional peptide; wherein the nucleic acids are operably linked so as to express a functional fusion protein.

14. The nucleic acid molecule of claim 13, wherein the SP is selected from the group consisting of: aggrecan signal peptide; CD44 signal peptide; link protein signal peptide; TSG-6 signal peptide; and versican signal peptide.

15. The nucleic acid molecule of claim 13, wherein the linker is selected from the group consisting of: Linker 1: GGSG (SEQ ID NO: 1); Linker 2: GGSGGGSG (SEQ ID NO: 2); Linker 3: GGSGGGSGGGSG (SEQ ID NO: 3); Linker 4: GGGGS (SEQ ID NO: 4); Linker 5: GGGGSGGGGS (SEQ ID NO: 5); Linker 6: GGGGSGGGGSGGGGS (SEQ ID NO: 6); Linker 7: GGSGGS (SEQ ID NO: 7); and Linker 8: VIGHPIDSE (SEQ ID NO: 8).

16. The nucleic acid molecule of claim 13, comprising a nucleic acid sequence that encodes a cleavage site for a protease selected from the group consisting of: enterokinase (EK); Furin; Factor Xa; Matrix metalloproteinase (MMP); and Aggrecanase.

17. The nucleic acid molecule of claim 12, wherein the GF is selected from the group consisting of: IGF-1; BMP2; BMP4; BMP7; FGF2; FGF18; GDF5; TGF-β1; and TGF-β3.

18. The nucleic acid molecule of claim 12, wherein the fusion protein further comprises flanking amino acids to the HAB polypeptide, wherein the number of flanking amino acids is selected from the group consisting of: at least 60 amino acids, at least 50 amino acids, at least 40 amino acids, at least 30 amino acids, at least 20 amino acids, fewer than 20 amino acids; fewer than 15 amino acids; fewer than 10 amino acids; and fewer than 5 amino acids.

19. A composition comprising the nucleic acid molecule of claim 12 and a pharmaceutically-acceptable carrier.

20. A composition comprising the fusion protein of claim 1 and a pharmaceutically-acceptable carrier.

21. An expression vector encoding the fusion protein of claim 1, wherein the expression vector is a plasmid or a virus.

22. The expression vector of claim 21, wherein the expression vector is an adeno-associated virus plasmid (pAAV).

23. An isolated cell transformed, transfected, or transduced by a vector of claim 21.

24. The cell of claim 23, wherein the cell is a chondrocyte.

25. A non-human animal comprising the cell of claim 23.

26. A method of producing a fusion protein comprising, expressing a nucleic acid molecule in the cell of claim 23.

27. A method to upregulate glycosaminoglycan expression in at least one chondrocyte, comprising: expressing the nucleic acid molecule of claim 12 in at least one chondrocyte.

28. A method for treating a cartilage matrix protein-related condition in a subject, the method comprising administering to the subject a composition of claim 20.

29. The method of claim 28, wherein the GF protein is IGF-I.

30. The method of claim 28, wherein the fusion protein is introduced to at least one chondrocyte in vivo.

31. The method of claim 28, wherein the fusion protein is administered to the subject intra-articularly.

32. The method of claim 28, wherein the cartilage matrix protein-related condition is selected from the group consisting of: joint stiffness; joint pain; intervertebral disc pain; degenerative disease; facet disease; traumatic cartilage injury; surgical cartilage injury; osteoarthritis; and rheumatoid arthritis.

33. The fusion protein of claim 1, wherein the GF protein is IGF-1.

34. The fusion protein of claim 1, wherein the fusion protein comprises an amino acid sequence that is at least 90 percent identical to SEQ ID NO: 72.

35. A fusion protein comprising IGF-1 and a polypeptide having an amino acid sequence at least 90 percent identical to amino acids 1-357 of SEQ ID NO: 44.

36. A fusion protein, comprising:
a hyaluronic acid-binding (HAB) polypeptide, wherein the HAB polypeptide is a polypeptide having at least 90 percent identity to a polypeptide of amino acids 1-178 of SEQ ID NO: 72;
a conserved region of a growth factor (GF) protein; and
at least one additional element selected from the group consisting of: aggrecan signal peptide; Linker 8: VIGHPIDSE (SEQ ID NO: 8); and the protease cleavage site of SEQ ID NO: 13,
wherein the fusion protein upregulates glycosaminoglycan (GAG) expression in chondrocytes.

* * * * *

SEQUENCE LISTING

```
<160> NUMBER OF SEQ ID NOS: 77

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Ser Gly
1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ser Gly Gly Gly Ser Gly
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Gly Gly Gly Ser Gly Gly Gly Ser Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser
```

-continued

```
1               5                    10
```

```
<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Ser Gly Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ile Gly His Pro Ile Asp Ser Glu
1               5

<210> SEQ ID NO 9
<211> LENGTH: 5
<212> TYPE: PRT
<213> ORGANISM: Unknown
<220> FEATURE:
<223> OTHER INFORMATION: Description of Unknown: EK protease cleavage
      site peptide

<400> SEQUENCE: 9

Asp Asp Asp Asp Lys
1               5

<210> SEQ ID NO 10
<211> LENGTH: 4
<212> TYPE: PRT
<213> ORGANISM: Unknown
<220> FEATURE:
<223> OTHER INFORMATION: Description of Unknown: Furin protease cleavage
      site peptide

<400> SEQUENCE: 10

Arg Val Arg Arg
1

<210> SEQ ID NO 11
<211> LENGTH: 4
<212> TYPE: PRT
<213> ORGANISM: Unknown
<220> FEATURE:
<223> OTHER INFORMATION: Description of Unknown: factor Xa protease
``` cleavage site peptide

<400> SEQUENCE: 11

Ile Glu Gly Arg
1

<210> SEQ ID NO 12
<211> LENGTH: 8
<212> TYPE: PRT
<213> ORGANISM: Unknown
<220> FEATURE:
<223> OTHER INFORMATION: Description of Unknown: MMP protease cleavage
      site peptide

<400> SEQUENCE: 12

Asp Ile Pro Glu Asn Phe Phe Gly
1               5

<210> SEQ ID NO 13
<211> LENGTH: 12
<212> TYPE: PRT
<213> ORGANISM: Unknown
<220> FEATURE:
<223> OTHER INFORMATION: Description of Unknown: Aggrecanase protease
      cleavage site peptide

<400> SEQUENCE: 13

Asn Ile Thr Glu Gly Glu Ala Arg Gly Ser Val Ile
1               5                   10

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaattcacca tggccacttt actctgggtt ttcgtgactc                              40

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggcccgatg tccacaaagt cttcacctgt gtag                                    34

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaattcacca tggagagtct acttcttctg gtgctgattt c                            41

<210> SEQ ID NO 17
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 17
gggcccgttg tatgctctga agcagtagac acc                                  33

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattcacca tggtcataaa tataaagagc atcttatgga                           40

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtcgaccaat tggatgacca attacactca aatcactc                             38

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtcgacgggc ccgagacgct ctgcggggct gagctggtg                            39

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caattgattc agaaggaccg gagacgctct gcggggctga g                         41

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctcgagctac atcctgtagt tcttgtttcc tg                                   32

<210> SEQ ID NO 23
<211> LENGTH: 32
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 23
gaattcacaa tgggaaaaat cagcagtctt cc                                    32

<210> SEQ ID NO 24
<211> LENGTH: 7296
<212> TYPE: DNA
<213> ORGANISM: Homo sapiens

<400> SEQUENCE: 24

```
atgaccactt tactctgggt tttcgtgact ctgagggtca tcactgcagc tgtcactgta      60
gaaacttcag accatgacaa ctcgctgagt gtcagcatcc ccaaccgtc  cccgctgagg     120
gtcctcctgg ggacctccct caccatcccc tgctatttca tcgacccat  gcaccctgtg    180
accaccgccc cttctaccgc cccactggcc caagaatca agtggagccg  tgtgtccaag    240
gagaaggagt agtgctgct ggtggccact gaagggcgcg tgcgggtcaa cagtgcctat     300
caggacaagg tctcactgcc caactacccg gccatcccca gtgacgccac cttggaagtc    360
cagagcctgc gctccaatga ctctggggtc taccgctgcg aggtgatgca tggcatcgag    420
gacagcgagg ccaccctgga agtcgtggtg aaaggcatcg tgttccatta cagagccatc    480
tctacacgct acaccctcga ctttgacagg gcgcagcggg cctgcctgca gaacagtgcc    540
atcattgcca cgcctgagca gctgcaggcc gcctacgaag acggcttcca ccagtgtgac    600
gccggctggc tggctgacca gactgtcaga taccccatcc acactccccg ggaaggctgc    660
tatggagaca aggatgagtt tcctggtgtg aggacgtatg gcatccgaga caccaacgag    720
acctatgatg tgtactgctt cgccgaggag atggagggtg aggtctttta tgcaacatct    780
ccagagaagt tcaccttcca ggaagcagcc aatgagtgcc ggcggctggg tgcccggctg    840
gccaccacgg gccagctcta cctggcctgg caggctggca tggacatgtg cagcgccggc    900
tggctggccg accgcagcgt gcgctacccc atctccaagg cccggcccaa ctgcggtggc    960
aacctcctgg gcgtgaggac cgtctacgtg catgccaacc agacgggcta ccccgacccc   1020
tcatcccgct acgacgccat ctgctacaca ggtgaagact tgtggacat  cccagaaaac   1080
ttctttggag tgggggtga ggaggacatc accgtccaga cagtgacctg gcctgacatg   1140
gagctgccac tgcctcgaaa catcactgag ggtgaagccc gaggcagcgt gatccttacc   1200
gtaaagccca tcttcgaggt ctcccccagt ccctggaac  ccgaggagcc cttcacgttt   1260
gcccctgaaa taggggccac tgccttcgct gaggttgaga tgagactgg  agaggccacc   1320
aggccctggg gctttcccac acctggcctg ggccctgcca cggcattcac cagtgaggac   1380
ctcgtcgtgc aggtgaccgc tgtccctggg cagccgcatt tgccaggggg ggtcgtcttc   1440
cactaccgcc cggacccac  ccgctactcg ctgacctttg aggaggcaca gcaggcctgc   1500
ctgcgcacgg gggcggtcat tgcctcgccg agcagctcc  aggccgccta cgaagcaggc   1560
tatgagcagt gtgacgccgg ctggctgcgg gaccagaccg tcagatacc  cattgtgagc   1620
ccccggaccc catgcgtggg tgacaaggac agcagcccag gggtcaggac ctatggcgtg   1680
cgcccatcaa cagagaccta cgatgtctac tgctttgtag acagcttga  ggggaggtg   1740
ttcttcgcca cacgccttga gcagttcacc ttccaggaag cactggagtt ctgtgaatct   1800
cacaatgcta cgctggccac cacgggccag ctctacgccg cctggagccg cggcctggac   1860
aagtgctatg ccggctggct ggccgacggc agcctccgct accccatcgt caccccaagg   1920
```

```
cctgcctgcg gtggggacaa gccaggcgtg agaacggtct acctctaccc taaccagacg    1980
ggcctcccag acccactgtc ccggcaccat gccttctgct tccgaggcat ttcagcggtt    2040
ccttctccag gagaagaaga gggtggcaca cccacatcac cctctggtgt ggaggagtgg    2100
atcgtgaccc aagtggttcc tggtgtggct gctgtccccg tagaagagga gacaactgct    2160
gtaccctcag gggagactac tgccatccta gagttcacca ccgagccaga aaaccagaca    2220
gaatgggaac cagcctatac cccagtgggc acatccccgc tgccagggat ccttcctact    2280
tggcctccca ctggcgcagc aacagaggaa agtacagaag gcccttctgc aactgaagtg    2340
ccctctgcct cagaggaacc atcccctca gaggtgccat tccctcaga ggagccatcc    2400 ccctcagagg aaccattccc ctcagtgagg ccattcccct cagtggagct gttcccctca    2460
gaggagccat tccctccaa ggagccatcc ccctcagagg aaccatcagc ctcggaagag    2520
ccgtatacac cttacccccc cgtgcccagc tggactgagc tgcccagctc tggggaggaa    2580 tctgggccc ctgatgtcag tggtgacttc acaggcagtg gagatgtttc aggacacctt    2640
gacttcagtg ggcagctgtc aggggacagg gcaagtggac tgccctctgg agacctggac    2700
tccagtggtc ttacttccac agtgggctca ggcctgcctg tggaaagtgg actaccctca    2760
ggggatgaag agagaattga gtggcccagc actcctacgg ttggtgaact gccctctgga    2820
gctgagatcc tagagggctc tgcctctgga gttgggatc tcagtggact tccttctgga    2880
gaagttctag agacctctgc ctctggagta ggagacctca gtgggcttcc ttctggagaa    2940
gttctagaga ccactgcccc tggagtagag gacatcagcg gcttccttc tggagaagtt    3000 ctagagacca ctgcccctgg agtagaggac atcagcgggc ttccttctgg agaagttcta    3060
gagaccactg cccctggagt agaggacatc agcgggcttc cttctggaga agttctagag    3120
accactgccc ctggagtaga ggacatcagc gggcttcctt ctggagaagt tctagagacc    3180
actgcccctg gagtagagga catcagcggg cttccttctg gagaagttct agagaccact    3240
gcccctggag tagaggacat cagcgggctt ccttctggag aagttctaga ccgctgcc    3300 cctggagtag aggacatcag cgggcttcct tctggagaag ttctagagac cgctgcccct    3360
ggagtagagg acatcagcgg gcttccttct ggagaagttc tagagaccgc tgcccctgga    3420
gtagaggaca tcagcgggct tccttctgga gaagttctag agaccgctgc ccctggagta    3480
gaggacatca gcgggcttcc ttctggagaa gttctagaga ccgctgcccc tggagtagag    3540
gacatcagcg ggcttccttc tggagaagtt ctagagaccg ctgcccctgg agtagaggac    3600
atcagcgggc ttccttctgg agaagttcta gagaccgctg cccctggagt agaggacatc    3660
agcgggcttc cttctggaga agttctagag actgctgccc ctggagtaga ggacatcagc    3720
gggcttcctt ctggagaagt tctagagact gctgccctg gagtagagga catcagcggg    3780
cttccttctg gagaagttct agagactgct gcccctggag tagaggacat cagcgggctt    3840
ccttctggag aagttctaga gactgctgcc cctggagtag aggacatcag cgggcttcct    3900
tctggagaag ttctagagac tgctgcccct ggagtagagg acatcagcgg gcttccttct    3960
ggagaagttc tagagactgc tgcccctgga gtagaggaca tcagcgggct tccttctgga    4020
gaagttctag agactgctgc ccctggagta ggacatca gcgggcttcc ttctggagaa    4080
gttctagaga ctgctgcccc tggagtagag gacatcagcg ggcttccttc tggagaagtt    4140
ctagagactg ctgcccctgg agtagaggac atcagcgggc ttccttctgg agaagttcta    4200
gagactactg cccctggagt agaggagatc agcgggcttc cttctggaga agttctagag    4260
actactgccc ctggagtaga tgagatcagt gggcttcctt ctggagaagt tctagagact    4320
```

```
actgccoctg gagtagagga gatcagcggg cttccttctg gagaagttct agagacttct    4380
acctctgcgg tagggacct  cagtggactt ccttctggag gagaagttct agagatttct    4440
gtctctggag tagaggacat cagtgggctt ccttctggag aggttgtaga gacttctgcc    4500
tctggaatag aggatgtcag tgaacttcct tcaggagaag gtctagagac ctctgcttct    4560
ggagtagagg acctcagcag gctcccttct ggagaagaag ttctagagat ttctgcctct    4620
ggatttgggg acctcagtgg acttccttct ggaggagaag gtctagagac ctctgcttct    4680
gaagtaggga ctgacctcag tgggcttcct tctggaaggg agggtctaga gacttcagct    4740
tctggagctg aggacctcag tgggttgcct tctggaaaag aagacttggt ggggtcagct    4800
tctggagact tggacttggg caaactgcct tctggaactc taggaagtgg gcaagctcca    4860
gaaacaagtg gtcttccctc tggatttagt ggtgagtatt ctggggtgga ccttggaagt    4920
ggcccaccct ctggcctgcc tgactttagt ggacttccat ctggattccc aactgtttcc    4980
ctagtggatt ctacattggt ggaagtggtc acagcctcca ctgcaagtga actggaaggg    5040
aggggaacca ttggcatcag tggtgcagga gaaatatctg gactgccctc cagtgagctg    5100
gacattagtg ggagagctag tggactccct tcaggaactg aactcagtgg ccaagcatct    5160
gggtctcctg atgtcagtgg ggaaatacct ggactctttg gtgtcagtgg acagccatca    5220
gggtttcctg acactagtgg ggaaacatct ggagtgactg agcttagcgg gctgtcctct    5280
ggacaaccag gtattagtgg agaagcatct ggagttcttt atggcactag tcaaccottt    5340 ggcataactg atctgagtgg agaaacatct ggggtccctg atctcagtgg gcagccttca    5400
gggttaccag ggttcagtgg ggcaacatca ggagtccctg acctggtttc tggtaccacg    5460
agtggcagcg gtgaatcttc tgggattaca tttgtggaca ccagtttggt tgaagtggcc    5520
cctactacat ttaaagaaga agaaggctta gggtctgtgg aactcagtgg cctcccttcc    5580
ggagaggcag atctgtcagg caaatctggg atggtggatg tcagtggaca gttttctgga    5640
acagtcgatt ccagtgggtt tacatcccag actccggaat tcagtggcct accaagtggc    5700
atagctgagg tcagtggaga atcctccaga gctgagattg ggagcagcct gccctcggga    5760
gcatattatg gcagtggaac tccatctagt ttccccactg tctctcttgt agacagaact    5820
ttggtggaat ctgtaaccca ggctccaaca gcccaagagg caggagaagg gccttctggc    5880
attttagaac tcagtggtgc tcattctgga gcaccagaca tgtctgggga gcattctgga    5940
tttctggacc taagtgggct gcagtccggg ctgatagagc ccagcggaga gccaccaggt    6000
actccatatt ttagtgggga ttttgccagc accaccaatg taagtggaga atcctctgta    6060
gccatgggca ccagtggaga ggcctcagga cttccagaag ttactttaat cacttctgag    6120
ttcgtggagg gtgttactga accaactatt tctcaggaac taggccaaag gccccctgtg    6180
acacacacac cccagctttt tgagtccagt ggaaaagtct ccacagctgg ggacattagt    6240
ggagctaccc cagtgctccc tgggtctgga gtagaagtat catcagtccc agaatctagc    6300
agtgagacgt ccgcctatcc tgaagctggg ttcggggcat ctgccgcccc tgaggccagc    6360
agagaagatt ctgggtcccc tgatctgagt gaaaccacct ctgcattcca cgaagctaac    6420
cttgagagat cctctggcct aggagtgagc ggcagcactt tgacatttca agaaggcgag    6480
gcgtccgctg ccccagaagt gagtggagaa tccaccacca ccagtgatgt ggggacagag    6540
gcaccaggct tgccttcagc cactcccacg gcttctggag acaggactga aatcagcgga    6600
gacctgtctg gtcacacctc gcagctgggc gttgtcatca gcaccagcat cccagagtct    6660
```

```
gagtggaccc agcagaccca gcgccctgca gagacgcatc tagaaattga gtcctcaagc    6720
ctcctgtact caggagaaga gactcacaca gtcgaaacag ccacctcccc aacagatgct    6780
tccatcccag cttctccgga atggaaacgt gaatcagaat caactgctgc agaccaggag    6840
gtatgtgagg agggctggaa caagtaccag ggccactgtt accgccactt cccggaccgc    6900
gagacctggg tggatgctga gcgccggtgt cgggagcagc agtcacacct gagcagcatc    6960 gtcaccccg aggagcagga gtttgtcaac aacaatgccc aagactacca gtggatcggc    7020
ctgaacgaca ggaccatcga aggggacttc cgctggtcag atggacaccc catgcaattt    7080
gagaactggc gccccaacca gcctgacaac ttttttgccg ctggagagga ctgtgtggtg    7140
atgatctggc acgagaaggg cgagtggaat gatgttccct gcaattacca cctccccttc    7200
acgtgtaaaa agggcacagc caccacctac aaacgcagac tacagaagcg gagctcacgg    7260
caccctcgga ggagccgccc cagcacagcc cactga                              7296

<210> SEQ ID NO 25
<211> LENGTH: 1071
<212> TYPE: DNA
<213> ORGANISM: Homo sapiens

<400> SEQUENCE: 25
atgaccactt tactctgggt tttcgtgact ctgagggtca tcactgcagc tgtcactgta      60
gaaacttcag accatgacaa ctcgctgagt gtcagcatcc cccaaccgtc cccgctgagg     120
gtcctcctgg ggacctccct caccatcccc tgctatttca tcgacccat gcaccctgtg     180 accaccgccc cttctaccgc cccactggcc caagaatca gtggagccg tgtgtccaag     240 gagaaggagg tagtgctgct ggtggccact gaagggcgcg tgcgggtcaa cagtgcctat     300
caggacaagg tctcactgcc caactaccg gccatcccca gtgacgccac cttggaagtc     360
cagagcctgc gctccaatga ctctggggtc taccgctgcg aggtgatgca tggcatcgag     420
gacagcgagg ccaccctgga agtcgtggtg aaaggcatcg tgttccatta cagagccatc     480
tctacacgct acaccctcga ctttgacagg gcgcagcggg cctgcctgca gaacagtgcc     540
atcattgcca cgcctgagca gctgcaggcc gcctacgaag acggcttcca ccagtgtgac     600
gccggctggc tggctgacca gactgtcaga taccccatcc acactccccg ggaaggctgc     660
tatggagaca aggatgagtt tcctggtgtg aggacgtatg gcatccgaga caccaacgag     720
acctatgatg tgtactgctt cgccgaggag atggagggtg aggtctttta tgcaacatct    780
ccagagaagt tcaccttcca ggaagcagcc aatgagtgcc ggcggctggg tgcccggctg    840
gccaccacgg gccagctcta cctggcctgg caggctggca tggacatgtg cagcgccggc    900
tggctggccg accgcagcgt gcgctacccc atctccaagg cccggccaa ctgcggtggc    960 aacctcctgg gcgtgaggac cgtctacgtg catgccaacc agacgggcta ccccgacccc   1020
tcatcccgct acgacgccat ctgctacaca ggtgaagact tgtggacat c              1071

<210> SEQ ID NO 26
<211> LENGTH: 2431
<212> TYPE: PRT
<213> ORGANISM: Homo sapiens

<400> SEQUENCE: 26

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
            20                  25                  30
```

```
Ile Pro Gln Pro Ser Pro Leu Arg Val Leu Gly Thr Ser Leu Thr
         35                  40                  45
Ile Pro Cys Tyr Phe Ile Asp Pro Met His Pro Val Thr Thr Ala Pro
 50                  55                  60
Ser Thr Ala Pro Leu Ala Pro Arg Ile Lys Trp Ser Arg Val Ser Lys
 65                  70                  75                  80
Glu Lys Glu Val Val Leu Leu Val Ala Thr Glu Gly Arg Val Arg Val
                 85                  90                  95
Asn Ser Ala Tyr Gln Asp Lys Val Ser Leu Pro Asn Tyr Pro Ala Ile
                100                 105                 110
Pro Ser Asp Ala Thr Leu Glu Val Gln Ser Leu Arg Ser Asn Asp Ser
            115                 120                 125
Gly Val Tyr Arg Cys Glu Val Met His Gly Ile Glu Asp Ser Glu Ala
            130                 135                 140
Thr Leu Glu Val Val Val Lys Gly Ile Val Phe His Tyr Arg Ala Ile
145                 150                 155                 160
Ser Thr Arg Tyr Thr Leu Asp Phe Asp Arg Ala Gln Arg Ala Cys Leu
                165                 170                 175
Gln Asn Ser Ala Ile Ile Ala Thr Pro Glu Gln Leu Gln Ala Ala Tyr
            180                 185                 190
Glu Asp Gly Phe His Gln Cys Asp Ala Gly Trp Leu Ala Asp Gln Thr
            195                 200                 205
Val Arg Tyr Pro Ile His Thr Pro Arg Glu Gly Cys Tyr Gly Asp Lys
            210                 215                 220
Asp Glu Phe Pro Gly Val Arg Thr Tyr Gly Ile Arg Asp Thr Asn Glu
225                 230                 235                 240
Thr Tyr Asp Val Tyr Cys Phe Ala Glu Glu Met Glu Gly Glu Val Phe
                245                 250                 255
Tyr Ala Thr Ser Pro Glu Lys Phe Thr Phe Gln Glu Ala Ala Asn Glu
            260                 265                 270
Cys Arg Arg Leu Gly Ala Arg Leu Ala Thr Thr Gly Gln Leu Tyr Leu
            275                 280                 285
Ala Trp Gln Ala Gly Met Asp Met Cys Ser Ala Gly Trp Leu Ala Asp
            290                 295                 300
Arg Ser Val Arg Tyr Pro Ile Ser Lys Ala Arg Pro Asn Cys Gly Gly
305                 310                 315                 320
Asn Leu Leu Gly Val Arg Thr Val Tyr Val His Ala Asn Gln Thr Gly
                325                 330                 335
Tyr Pro Asp Pro Ser Ser Arg Tyr Asp Ala Ile Cys Tyr Thr Gly Glu
            340                 345                 350
Asp Phe Val Asp Ile Pro Glu Asn Phe Phe Gly Val Gly Gly Glu Glu
            355                 360                 365
Asp Ile Thr Val Gln Thr Val Thr Trp Pro Asp Met Glu Leu Pro Leu
370                 375                 380
Pro Arg Asn Ile Thr Glu Gly Glu Ala Arg Gly Ser Val Ile Leu Thr
385                 390                 395                 400
Val Lys Pro Ile Phe Glu Val Ser Pro Ser Pro Leu Glu Pro Glu Glu
                405                 410                 415
Pro Phe Thr Phe Ala Pro Glu Ile Gly Ala Thr Ala Phe Ala Glu Val
            420                 425                 430
Glu Asn Glu Thr Gly Glu Ala Thr Arg Pro Trp Gly Phe Pro Thr Pro
            435                 440                 445
```

-continued

```
Gly Leu Gly Pro Ala Thr Ala Phe Thr Ser Glu Asp Leu Val Val Gln
        450                 455                 460
Val Thr Ala Val Pro Gly Gln Pro His Leu Pro Gly Val Val Phe
465                 470                 475                 480
His Tyr Arg Pro Gly Pro Thr Arg Tyr Ser Leu Thr Phe Glu Glu Ala
                485                 490                 495
Gln Gln Ala Cys Leu Arg Thr Gly Ala Val Ile Ala Ser Pro Glu Gln
                500                 505                 510
Leu Gln Ala Ala Tyr Glu Ala Gly Tyr Glu Gln Cys Asp Ala Gly Trp
                515                 520                 525
Leu Arg Asp Gln Thr Val Arg Tyr Pro Ile Val Ser Pro Arg Thr Pro
530                 535                 540
Cys Val Gly Asp Lys Asp Ser Ser Pro Gly Val Arg Thr Tyr Gly Val
545                 550                 555                 560
Arg Pro Ser Thr Glu Thr Tyr Asp Val Tyr Cys Phe Val Asp Arg Leu
                565                 570                 575
Glu Gly Glu Val Phe Phe Ala Thr Arg Leu Glu Gln Phe Thr Phe Gln
                580                 585                 590
Glu Ala Leu Glu Phe Cys Glu Ser His Asn Ala Thr Leu Ala Thr Thr
                595                 600                 605
Gly Gln Leu Tyr Ala Ala Trp Ser Arg Gly Leu Asp Lys Cys Tyr Ala
        610                 615                 620
Gly Trp Leu Ala Asp Gly Ser Leu Arg Tyr Pro Ile Val Thr Pro Arg
625                 630                 635                 640
Pro Ala Cys Gly Gly Asp Lys Pro Gly Val Arg Thr Val Tyr Leu Tyr
                645                 650                 655
Pro Asn Gln Thr Gly Leu Pro Asp Pro Leu Ser Arg His His Ala Phe
                660                 665                 670
Cys Phe Arg Gly Ile Ser Ala Val Pro Ser Pro Gly Glu Glu Glu Gly
        675                 680                 685
Gly Thr Pro Thr Ser Pro Ser Gly Val Glu Glu Trp Ile Val Thr Gln
        690                 695                 700
Val Val Pro Gly Val Ala Ala Val Pro Val Glu Glu Glu Thr Thr Ala
705                 710                 715                 720
Val Pro Ser Gly Glu Thr Thr Ala Ile Leu Glu Phe Thr Thr Glu Pro
                725                 730                 735
Glu Asn Gln Thr Glu Trp Glu Pro Ala Tyr Thr Pro Val Gly Thr Ser
                740                 745                 750
Pro Leu Pro Gly Ile Leu Pro Thr Trp Pro Pro Thr Gly Ala Ala Thr
                755                 760                 765
Glu Glu Ser Thr Glu Gly Pro Ser Ala Thr Glu Val Pro Ser Ala Ser
770                 775                 780
Glu Glu Pro Ser Pro Ser Glu Val Pro Phe Pro Ser Glu Glu Pro Ser
785                 790                 795                 800
Pro Ser Glu Glu Pro Phe Pro Ser Val Arg Pro Phe Pro Ser Val Glu
                805                 810                 815
Leu Phe Pro Ser Glu Glu Pro Phe Pro Ser Lys Glu Pro Ser Pro Ser
                820                 825                 830
Glu Glu Pro Ser Ala Ser Glu Glu Pro Tyr Thr Pro Ser Pro Pro Val
                835                 840                 845
Pro Ser Trp Thr Glu Leu Pro Ser Ser Gly Glu Glu Ser Gly Ala Pro
850                 855                 860
Asp Val Ser Gly Asp Phe Thr Gly Ser Gly Asp Val Ser Gly His Leu
```

```
                865                 870                 875                 880
Asp Phe Ser Gly Gln Leu Ser Gly Asp Arg Ala Ser Gly Leu Pro Ser
                    885                 890                 895
Gly Asp Leu Asp Ser Ser Gly Leu Thr Ser Thr Val Gly Ser Gly Leu
                900                 905                 910
Pro Val Glu Ser Gly Leu Pro Ser Gly Asp Glu Glu Arg Ile Glu Trp
                915                 920                 925
Pro Ser Thr Pro Thr Val Gly Glu Leu Pro Ser Gly Ala Glu Ile Leu
            930                 935                 940
Glu Gly Ser Ala Ser Gly Val Gly Asp Leu Ser Gly Leu Pro Ser Gly
945                 950                 955                 960
Glu Val Leu Glu Thr Ser Ala Ser Gly Val Gly Asp Leu Ser Gly Leu
                965                 970                 975
Pro Ser Gly Glu Val Leu Glu Thr Thr Ala Pro Gly Val Glu Asp Ile
            980                 985                 990
Ser Gly Leu Pro Ser Gly Glu Val Leu Glu Thr Thr Ala Pro Gly Val
                995                1000                1005
Glu Asp Ile Ser Gly Leu Pro Ser Gly Glu Val Leu Glu Thr Thr
        1010                1015                1020
Ala Pro Gly Val Glu Asp Ile Ser Gly Leu Pro Ser Gly Glu Val
    1025                1030                1035
Leu Glu Thr Thr Ala Pro Gly Val Glu Asp Ile Ser Gly Leu Pro
    1040                1045                1050
Ser Gly Glu Val Leu Glu Thr Thr Ala Pro Gly Val Glu Asp Ile
    1055                1060                1065
Ser Gly Leu Pro Ser Gly Glu Val Leu Glu Thr Thr Ala Pro Gly
    1070                1075                1080
Val Glu Asp Ile Ser Gly Leu Pro Ser Gly Glu Val Leu Glu Thr
    1085                1090                1095
Ala Ala Pro Gly Val Glu Asp Ile Ser Gly Leu Pro Ser Gly Glu
    1100                1105                1110
Val Leu Glu Thr Ala Ala Pro Gly Val Glu Asp Ile Ser Gly Leu
    1115                1120                1125
Pro Ser Gly Glu Val Leu Glu Thr Ala Ala Pro Gly Val Glu Asp
    1130                1135                1140
Ile Ser Gly Leu Pro Ser Gly Glu Val Leu Glu Thr Ala Ala Pro
    1145                1150                1155
Gly Val Glu Asp Ile Ser Gly Leu Pro Ser Gly Glu Val Leu Glu
    1160                1165                1170
Thr Ala Ala Pro Gly Val Glu Asp Ile Ser Gly Leu Pro Ser Gly
    1175                1180                1185
Glu Val Leu Glu Thr Ala Ala Pro Gly Val Glu Asp Ile Ser Gly
    1190                1195                1200
Leu Pro Ser Gly Glu Val Leu Glu Thr Ala Ala Pro Gly Val Glu
    1205                1210                1215
Asp Ile Ser Gly Leu Pro Ser Gly Glu Val Leu Glu Thr Ala Ala
    1220                1225                1230
Pro Gly Val Glu Asp Ile Ser Gly Leu Pro Ser Gly Glu Val Leu
    1235                1240                1245
Glu Thr Ala Ala Pro Gly Val Glu Asp Ile Ser Gly Leu Pro Ser
    1250                1255                1260
Gly Glu Val Leu Glu Thr Ala Ala Pro Gly Val Glu Asp Ile Ser
    1265                1270                1275
```

```
Gly Leu Pro Ser Gly Glu Val Leu Glu Thr Ala Ala Pro Gly Val
    1280            1285                1290
Glu Asp Ile Ser Gly Leu Pro Ser Gly Glu Val Leu Glu Thr Ala
    1295            1300                1305
Ala Pro Gly Val Glu Asp Ile Ser Gly Leu Pro Ser Gly Glu Val
    1310            1315                1320
Leu Glu Thr Ala Ala Pro Gly Val Glu Asp Ile Ser Gly Leu Pro
    1325            1330                1335
Ser Gly Glu Val Leu Glu Thr Ala Ala Pro Gly Val Glu Asp Ile
    1340            1345                1350
Ser Gly Leu Pro Ser Gly Val Leu Glu Thr Ala Ala Pro Gly
    1355            1360                1365
Val Glu Asp Ile Ser Gly Leu Pro Ser Gly Glu Val Leu Glu Thr
    1370            1375                1380
Ala Ala Pro Gly Val Glu Asp Ile Ser Gly Leu Pro Ser Gly Glu
    1385            1390                1395
Val Leu Glu Thr Thr Ala Pro Gly Val Glu Glu Ile Ser Gly Leu
    1400            1405                1410
Pro Ser Gly Glu Val Leu Glu Thr Thr Ala Pro Gly Val Asp Glu
    1415            1420                1425
Ile Ser Gly Leu Pro Ser Gly Glu Val Leu Glu Thr Thr Ala Pro
    1430            1435                1440
Gly Val Glu Glu Ile Ser Gly Leu Pro Ser Gly Glu Val Leu Glu
    1445            1450                1455
Thr Ser Thr Ser Ala Val Gly Asp Leu Ser Gly Leu Pro Ser Gly
    1460            1465                1470
Gly Glu Val Leu Glu Ile Ser Val Ser Gly Val Glu Asp Ile Ser
    1475            1480                1485
Gly Leu Pro Ser Gly Glu Val Val Glu Thr Ser Ala Ser Gly Ile
    1490            1495                1500
Glu Asp Val Ser Glu Leu Pro Ser Gly Glu Gly Leu Glu Thr Ser
    1505            1510                1515
Ala Ser Gly Val Glu Asp Leu Ser Arg Leu Pro Ser Gly Glu Glu
    1520            1525                1530
Val Leu Glu Ile Ser Ala Ser Gly Phe Gly Asp Leu Ser Gly Leu
    1535            1540                1545
Pro Ser Gly Gly Glu Gly Leu Glu Thr Ser Ala Ser Glu Val Gly
    1550            1555                1560
Thr Asp Leu Ser Gly Leu Pro Ser Gly Arg Glu Gly Leu Glu Thr
    1565            1570                1575
Ser Ala Ser Gly Ala Glu Asp Leu Ser Gly Leu Pro Ser Gly Lys
    1580            1585                1590
Glu Asp Leu Val Gly Ser Ala Ser Gly Asp Leu Asp Leu Gly Lys
    1595            1600                1605
Leu Pro Ser Gly Thr Leu Gly Ser Gly Gln Ala Pro Glu Thr Ser
    1610            1615                1620
Gly Leu Pro Ser Gly Phe Ser Gly Glu Tyr Ser Gly Val Asp Leu
    1625            1630                1635
Gly Ser Gly Pro Pro Ser Gly Leu Pro Asp Phe Ser Gly Leu Pro
    1640            1645                1650
Ser Gly Phe Pro Thr Val Ser Leu Val Asp Ser Thr Leu Val Glu
    1655            1660                1665
```

-continued

| | | | | | | | | | | | |
|---|---|---|---|---|---|---|---|---|---|---|---|
| Val | Val | Thr | Ala | Ser | Thr | Ala | Ser | Glu | Leu | Glu | Gly | Arg | Gly | Thr |
| | 1670 | | | | 1675 | | | | | 1680 | | | | |
| Ile | Gly | Ile | Ser | Gly | Ala | Gly | Glu | Ile | Ser | Gly | Leu | Pro | Ser | Ser |
| | 1685 | | | | 1690 | | | | | 1695 | | | | |
| Glu | Leu | Asp | Ile | Ser | Gly | Arg | Ala | Ser | Gly | Leu | Pro | Ser | Gly | Thr |
| | 1700 | | | | 1705 | | | | | 1710 | | | | |
| Glu | Leu | Ser | Gly | Gln | Ala | Ser | Gly | Ser | Pro | Asp | Val | Ser | Gly | Glu |
| | 1715 | | | | 1720 | | | | | 1725 | | | | |
| Ile | Pro | Gly | Leu | Phe | Gly | Val | Ser | Gly | Gln | Pro | Ser | Gly | Phe | Pro |
| | 1730 | | | | 1735 | | | | | 1740 | | | | |
| Asp | Thr | Ser | Gly | Glu | Thr | Ser | Gly | Val | Thr | Glu | Leu | Ser | Gly | Leu |
| | 1745 | | | | 1750 | | | | | 1755 | | | | |
| Ser | Ser | Gly | Gln | Pro | Gly | Ile | Ser | Gly | Glu | Ala | Ser | Gly | Val | Leu |
| | 1760 | | | | 1765 | | | | | 1770 | | | | |
| Tyr | Gly | Thr | Ser | Gln | Pro | Phe | Gly | Ile | Thr | Asp | Leu | Ser | Gly | Glu |
| | 1775 | | | | 1780 | | | | | 1785 | | | | |
| Thr | Ser | Gly | Val | Pro | Asp | Leu | Ser | Gly | Gln | Pro | Ser | Gly | Leu | Pro |
| | 1790 | | | | 1795 | | | | | 1800 | | | | |
| Gly | Phe | Ser | Gly | Ala | Thr | Ser | Gly | Val | Pro | Asp | Leu | Val | Ser | Gly |
| | 1805 | | | | 1810 | | | | | 1815 | | | | |
| Thr | Thr | Ser | Gly | Ser | Gly | Glu | Ser | Ser | Gly | Ile | Thr | Phe | Val | Asp |
| | 1820 | | | | 1825 | | | | | 1830 | | | | |
| Thr | Ser | Leu | Val | Glu | Val | Ala | Pro | Thr | Thr | Phe | Lys | Glu | Glu | Glu |
| | 1835 | | | | 1840 | | | | | 1845 | | | | |
| Gly | Leu | Gly | Ser | Val | Glu | Leu | Ser | Gly | Leu | Pro | Ser | Gly | Glu | Ala |
| | 1850 | | | | 1855 | | | | | 1860 | | | | |
| Asp | Leu | Ser | Gly | Lys | Ser | Gly | Met | Val | Asp | Val | Ser | Gly | Gln | Phe |
| | 1865 | | | | 1870 | | | | | 1875 | | | | |
| Ser | Gly | Thr | Val | Asp | Ser | Ser | Gly | Phe | Thr | Ser | Gln | Thr | Pro | Glu |
| | 1880 | | | | 1885 | | | | | 1890 | | | | |
| Phe | Ser | Gly | Leu | Pro | Ser | Gly | Ile | Ala | Glu | Val | Ser | Gly | Glu | Ser |
| | 1895 | | | | 1900 | | | | | 1905 | | | | |
| Ser | Arg | Ala | Glu | Ile | Gly | Ser | Ser | Leu | Pro | Ser | Gly | Ala | Tyr | Tyr |
| | 1910 | | | | 1915 | | | | | 1920 | | | | |
| Gly | Ser | Gly | Thr | Pro | Ser | Ser | Phe | Pro | Thr | Val | Ser | Leu | Val | Asp |
| | 1925 | | | | 1930 | | | | | 1935 | | | | |
| Arg | Thr | Leu | Val | Glu | Ser | Val | Thr | Gln | Ala | Pro | Thr | Ala | Gln | Glu |
| | 1940 | | | | 1945 | | | | | 1950 | | | | |
| Ala | Gly | Glu | Gly | Pro | Ser | Gly | Ile | Leu | Glu | Leu | Ser | Gly | Ala | His |
| | 1955 | | | | 1960 | | | | | 1965 | | | | |
| Ser | Gly | Ala | Pro | Asp | Met | Ser | Gly | Glu | His | Ser | Gly | Phe | Leu | Asp |
| | 1970 | | | | 1975 | | | | | 1980 | | | | |
| Leu | Ser | Gly | Leu | Gln | Ser | Gly | Leu | Ile | Glu | Pro | Ser | Gly | Glu | Pro |
| | 1985 | | | | 1990 | | | | | 1995 | | | | |
| Pro | Gly | Thr | Pro | Tyr | Phe | Ser | Gly | Asp | Phe | Ala | Ser | Thr | Thr | Asn |
| | 2000 | | | | 2005 | | | | | 2010 | | | | |
| Val | Ser | Gly | Glu | Ser | Ser | Val | Ala | Met | Gly | Thr | Ser | Gly | Glu | Ala |
| | 2015 | | | | 2020 | | | | | 2025 | | | | |
| Ser | Gly | Leu | Pro | Glu | Val | Thr | Leu | Ile | Thr | Ser | Glu | Phe | Val | Glu |
| | 2030 | | | | 2035 | | | | | 2040 | | | | |
| Gly | Val | Thr | Glu | Pro | Thr | Ile | Ser | Gln | Glu | Leu | Gly | Gln | Arg | Pro |
| | 2045 | | | | 2050 | | | | | 2055 | | | | |
| Pro | Val | Thr | His | Thr | Pro | Gln | Leu | Phe | Glu | Ser | Ser | Gly | Lys | Val |

2060                2065                2070

Ser Thr Ala Gly Asp Ile Ser Gly Ala Thr Pro Val Leu Pro Gly
    2075                2080                2085

Ser Gly Val Glu Val Ser Ser Val Pro Glu Ser Ser Ser Glu Thr
    2090                2095                2100

Ser Ala Tyr Pro Glu Ala Gly Phe Gly Ala Ser Ala Ala Pro Glu
    2105                2110                2115

Ala Ser Arg Glu Asp Ser Gly Ser Pro Asp Leu Ser Glu Thr Thr
    2120                2125                2130

Ser Ala Phe His Glu Ala Asn Leu Glu Arg Ser Ser Gly Leu Gly
    2135                2140                2145

Val Ser Gly Ser Thr Leu Thr Phe Gln Glu Gly Glu Ala Ser Ala
    2150                2155                2160

Ala Pro Glu Val Ser Gly Glu Ser Thr Thr Thr Ser Asp Val Gly
    2165                2170                2175

Thr Glu Ala Pro Gly Leu Pro Ser Ala Thr Pro Thr Ala Ser Gly
    2180                2185                2190

Asp Arg Thr Glu Ile Ser Gly Asp Leu Ser Gly His Thr Ser Gln
    2195                2200                2205

Leu Gly Val Val Ile Ser Thr Ser Ile Pro Glu Ser Glu Trp Thr
    2210                2215                2220

Gln Gln Thr Gln Arg Pro Ala Glu Thr His Leu Glu Ile Glu Ser
    2225                2230                2235

Ser Ser Leu Leu Tyr Ser Gly Glu Glu Thr His Thr Val Glu Thr
    2240                2245                2250

Ala Thr Ser Pro Thr Asp Ala Ser Ile Pro Ala Ser Pro Glu Trp
    2255                2260                2265

Lys Arg Glu Ser Glu Ser Thr Ala Ala Asp Gln Glu Val Cys Glu
    2270                2275                2280

Glu Gly Trp Asn Lys Tyr Gln Gly His Cys Tyr Arg His Phe Pro
    2285                2290                2295

Asp Arg Glu Thr Trp Val Asp Ala Glu Arg Arg Cys Arg Glu Gln
    2300                2305                2310

Gln Ser His Leu Ser Ser Ile Val Thr Pro Glu Glu Gln Glu Phe
    2315                2320                2325

Val Asn Asn Asn Ala Gln Asp Tyr Gln Trp Ile Gly Leu Asn Asp
    2330                2335                2340

Arg Thr Ile Glu Gly Asp Phe Arg Trp Ser Asp Gly His Pro Met
    2345                2350                2355

Gln Phe Glu Asn Trp Arg Pro Asn Gln Pro Asp Asn Phe Phe Ala
    2360                2365                2370

Ala Gly Glu Asp Cys Val Val Met Ile Trp His Glu Lys Gly Glu
    2375                2380                2385

Trp Asn Asp Val Pro Cys Asn Tyr His Leu Pro Phe Thr Cys Lys
    2390                2395                2400

Lys Gly Thr Ala Thr Thr Tyr Lys Arg Arg Leu Gln Lys Arg Ser
    2405                2410                2415

Ser Arg His Pro Arg Arg Ser Arg Pro Ser Thr Ala His
    2420                2425                2430

<210> SEQ ID NO 27
<211> LENGTH: 357
<212> TYPE: PRT
<213> ORGANISM: Homo sapiens

<400> SEQUENCE: 27

```
Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
            20                  25                  30

Ile Pro Gln Pro Ser Pro Leu Arg Val Leu Leu Gly Thr Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Ala Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile
        355
```

<210> SEQ ID NO 28
<211> LENGTH: 1065
<212> TYPE: DNA
<213> ORGANISM: Homo sapiens

<400> SEQUENCE: 28

-continued

```
atgaagagtc tacttcttct ggtgctgatt tcaatctgct gggctgatca tctttcagac    60
aactatactc tggatcatga cagagctatt cacatccaag cagaaaatgg cccccatcta   120
cttgtggaag cagagcaagc caaggtgttt tcacacagag gtggcaatgt tacactgcca   180
tgtaaatttt atcgagaccc tacagcattt ggctcaggaa tccataaaat ccgaattaag   240
tggaccaagc taacttcgga ttacctcaag gaagtggatg ttttgtttc catgggatac    300
cacaaaaaaa cctatggagg ctaccagggt agagtgtttc tgaagggagg cagtgatagt   360
gatgcttctc tggtcatcac agacctcact ctggaagatt atgggagata aagtgtgag    420
gtgattgaag gattagaaga tgatactgtt gtggtagcac tggacttaca aggtgtggta   480
ttcccttact ttccacgact ggggcgctac aatctcaatt ttcacgaggc gcagcaggcg   540
tgtctggacc aggatgctgt gatcgcctcc ttcgaccagc tgtacgacgc ctggcggggc   600
gggctggact ggtgcaatgc cggctggctc agtgatggct ctgtgcaata tcccatcaca   660
aagcccagag agccctgtgg ggggcagaac acagtgcccg gagtcaggaa ctacggattt   720
tgggataaag ataaaagcag atatgatgtt ttctgtttta catccaattt caatggccgt   780
ttttactatc tgatccaccc caccaaactg acctatgatg aagcggtgca agcttgtctc   840
aatgatggtg ctcagattgc aaaagtgggc cagatatttg ctgcctggaa aattctcgga   900
tatgaccgct gtgatgcggg ctggttggcg gatggcagcg tccgctaccc catctctagg   960
ccaagaaggc gctgcagtcc tactgaggct gcagtgcgct tcgtgggttt cccagataaa  1020
aagcataagc tgtatggtgt ctactgcttc agagcataca actga                  1065
```

<210> SEQ ID NO 29
<211> LENGTH: 354
<212> TYPE: PRT
<213> ORGANISM: Homo sapiens

<400> SEQUENCE: 29

```
Met Lys Ser Leu Leu Leu Val Leu Ile Ser Ile Cys Trp Ala Asp
1               5                   10                  15

His Leu Ser Asp Asn Tyr Thr Leu Asp His Asp Arg Ala Ile His Ile
            20                  25                  30

Gln Ala Glu Asn Gly Pro His Leu Leu Val Glu Ala Glu Gln Ala Lys
        35                  40                  45

Val Phe Ser His Arg Gly Gly Asn Val Thr Leu Pro Cys Lys Phe Tyr
    50                  55                  60

Arg Asp Pro Thr Ala Phe Gly Ser Gly Ile His Lys Ile Arg Ile Lys
65                  70                  75                  80

Trp Thr Lys Leu Thr Ser Asp Tyr Leu Lys Glu Val Asp Val Phe Val
                85                  90                  95

Ser Met Gly Tyr His Lys Lys Thr Tyr Gly Gly Tyr Gln Gly Arg Val
            100                 105                 110

Phe Leu Lys Gly Gly Ser Asp Ser Asp Ala Ser Leu Val Ile Thr Asp
        115                 120                 125

Leu Thr Leu Glu Asp Tyr Gly Arg Tyr Lys Cys Glu Val Ile Glu Gly
    130                 135                 140

Leu Glu Asp Asp Thr Val Val Val Ala Leu Asp Leu Gln Gly Val Val
145                 150                 155                 160

Phe Pro Tyr Phe Pro Arg Leu Gly Arg Tyr Asn Leu Asn Phe His Glu
                165                 170                 175

Ala Gln Gln Ala Cys Leu Asp Gln Asp Ala Val Ile Ala Ser Phe Asp
```

|     |     |     |     |     | 180 |     |     |     | 185 |     |     |     |     | 190 |     |
| --- | --- | --- | --- | --- | --- | --- | --- | --- | --- | --- | --- | --- | --- | --- | --- |
| Gln | Leu | Tyr | Asp | Ala | Trp | Arg | Gly | Gly | Leu | Asp | Trp | Cys | Asn | Ala | Gly |
|     |     |     | 195 |     |     |     |     | 200 |     |     |     |     | 205 |     |     |
| Trp | Leu | Ser | Asp | Gly | Ser | Val | Gln | Tyr | Pro | Ile | Thr | Lys | Pro | Arg | Glu |
|     | 210 |     |     |     |     |     | 215 |     |     |     |     | 220 |     |     |     |
| Pro | Cys | Gly | Gly | Gln | Asn | Thr | Val | Pro | Gly | Val | Arg | Asn | Tyr | Gly | Phe |
| 225 |     |     |     |     | 230 |     |     |     |     | 235 |     |     |     |     | 240 |
| Trp | Asp | Lys | Asp | Lys | Ser | Arg | Tyr | Asp | Val | Phe | Cys | Phe | Thr | Ser | Asn |
|     |     |     |     | 245 |     |     |     |     | 250 |     |     |     |     | 255 |     |
| Phe | Asn | Gly | Arg | Phe | Tyr | Tyr | Leu | Ile | His | Pro | Thr | Lys | Leu | Thr | Tyr |
|     |     |     | 260 |     |     |     |     | 265 |     |     |     |     | 270 |     |     |
| Asp | Glu | Ala | Val | Gln | Ala | Cys | Leu | Asn | Asp | Gly | Ala | Gln | Ile | Ala | Lys |
|     |     | 275 |     |     |     |     | 280 |     |     |     |     | 285 |     |     |     |
| Val | Gly | Gln | Ile | Phe | Ala | Ala | Trp | Lys | Ile | Leu | Gly | Tyr | Asp | Arg | Cys |
|     | 290 |     |     |     |     | 295 |     |     |     |     | 300 |     |     |     |     |
| Asp | Ala | Gly | Trp | Leu | Ala | Asp | Gly | Ser | Val | Arg | Tyr | Pro | Ile | Ser | Arg |
| 305 |     |     |     |     | 310 |     |     |     |     | 315 |     |     |     |     | 320 |
| Pro | Arg | Arg | Arg | Cys | Ser | Pro | Thr | Glu | Ala | Ala | Val | Arg | Phe | Val | Gly |
|     |     |     |     | 325 |     |     |     |     | 330 |     |     |     |     | 335 |     |
| Phe | Pro | Asp | Lys | Lys | His | Lys | Leu | Tyr | Gly | Val | Tyr | Cys | Phe | Arg | Ala |
|     |     |     | 340 |     |     |     |     | 345 |     |     |     |     | 350 |     |     |
| Tyr | Asn |     |     |     |     |     |     |     |     |     |     |     |     |     |     |

<210> SEQ ID NO 30
<211> LENGTH: 7230
<212> TYPE: DNA
<213> ORGANISM: Homo sapiens

<400> SEQUENCE: 30

```
atgttcataa atataaagag catcttatgg atgtgttcaa ccttaatagt aacccatgcg      60
ctacataaag tcaaagtggg aaaaagccca ccggtgaggg gctccctctc tggaaaagtc     120
agcctacctt gtcatttttc aacgatgcct actttgccac ccagttacaa caccagtgaa     180
tttctccgca tcaaatggtc taagattgaa gtggacaaaa atggaaagag tttgaaagag     240
actactgtcc ttgtggccca aaatggaaat atcaagattg gtcaggacta caagggaga      300
gtgtctgtgc ccacacatcc cgaggctgtg ggcgatgcct ccctcactgt ggtcaagctg     360
ctggcaagtg atgcgggtct ttaccgctgt gacgtcatgt acgggattga agacacacaa     420
gacacggtgt cactgactgt ggatggggtt gtgtttcact acagggcggc aaccagcagg     480
tacacactga attttgaggc tgctcagaag gcttgtttgg acgttggggc agtcatagca     540
actccagagc agctctttgc tgcctatgaa gatggatttg agcagtgtga cgcaggctgg     600
ctggctgatc agactgtcag atatcccatc cgggctccca gagtaggctg ttatggagat     660
aagatgggaa aggcaggagt caggacttat ggattccgtt ctccccagga aacttacgat     720
gtgtattgtt atgtggatca tctggatggt gatgtgttcc acctcactgt ccccagtaaa     780
ttcaccttcg aggaggctgc aaaagagtgt gaaaaccagg atgccaggct ggcaacagtg     840
ggggaactcc aggcggcatg gaggaacggc tttgaccagt gcgattacgg gtggctgtcg     900
gatgccagcg tgcgccaccc tgtgactgtg gccagggccc agtgtggagg tggtctactt     960
ggggtgagaa ccctgtatcg tttttgagaac cagacaggct cccctccccc tgatagcaga    1020
tttgatgcct actgctttaa acgtcgaatg agtgatttga gtgtaattgg tcatccaata    1080
gattcagaat ctaaagaaga tgaaccttgt agtgaagaaa cagatccagt gcatgatcta    1140
```

```
atggctgaaa ttttacctga attccctgac ataattgaaa tagacctata ccacagtgaa    1200
gaaaatgaag aagaagaaga agagtgtgca aatgctactg atgtgacaac cacccatct     1260 gtgcagtaca taaatgggaa gcatctcgtt accactgtgc ccaaggaccc agaagctgca    1320
gaagctaggc gtggccagtt tgaaagtgtt gcaccttctc agaatttctc ggacagctct    1380
gaaagtgata ctcatccatt tgtaatagcc aaaacggaat tgtctactgc tgtgcaacct    1440
aatgaatcta cagaaacaac tgagtctctt gaagttacat ggaagcctga gacttaccct    1500
gaaacatcag aacattttc aggtggtgag cctgatgttt tccccacagt cccattccat    1560
gaggaatttg aaagtggaac agccaaaaaa ggggcagaat cagtcacaga gagagatact    1620
gaagttggtc atcaggcaca tgaacatact gaacctgtat ctctgtttcc tgaagagtct    1680
tcaggagaga ttgccattga ccaagaatct cagaaaatag cctttgcaag gctacagaa     1740 gtaacatttg gtgaagaggt agaaaaaagt acttctgtca catacactcc cactatagtt    1800
ccaagttctg catcagcata tgtttcagag gaagaagcag ttaccctaat aggaaatcct    1860
tggccagatg acctgttgtc taccaaagaa agctgggtag aagcaactcc tagacaagtt    1920
gtagagctct cagggagttc ttcgattcca attacagaag gctctggaga agcagaagaa    1980
gatgaagata caatgttcac catggtaact gatttatcac agagaaatac tactgataca    2040
ctcattactt tagacactag caggataatc acagaaagct ttttgaggt tcctgcaacc     2100 accatttatc cagtttctga caaccttct gcaaaagtgg tgcctaccaa gtttgtaagt     2160
gaaacagaca cttctgagtg gatttccagt accactgttg aggaaaagaa aaggaaggag    2220
gaggagggaa ctacaggtac ggcttctaca tttgaggtat attcatctac acagagatcg    2280
gatcaattaa ttttacccctt tgaattagaa agtccaaatg tagctacatc tagtgattca    2340
ggtaccagga aaagttttat gtccttgaca acaccaacac agtctgaaag ggaaatgaca    2400
gattctactc ctgtctttac agaaacaaat acattagaaa atttggggc acagaccact    2460 gagcacagca gtatccatca acctggggtt caggaagggc tgaccactct cccacgtagt    2520
cctgcctctg tctttatgga gcagggctct ggagaagctg ctgccgaccc agaaccacc    2580 actgtttctt cattttcatt aaacgtagag tatgcaattc aagccgaaaa ggaagtagct    2640
ggcactttgt ctccgcatgt ggaaactaca ttctccactg agccaacagg actggtttg    2700 agtacagtaa tggacagagt agttgctgaa aatataaccc aaacatccag ggaaatagtg    2760
atttcagagc gattaggaga accaaattat ggggcagaaa taaggggctt ttccacaggt    2820 tttccttttgg aggaagattt cagtggtgac tttagagaat actcaacagt gtctcatccc    2880
atagcaaaag aagaaacggt aatgatggaa ggctctggag atgcagcatt tagggacacc    2940
cagacttcac catctacagt acctacttca gttcacatca gtcacatatc tgactcagaa    3000
ggacccagta gcaccatggt cagcacttca gccttcccct gggaagagtt tacatcctca    3060
gctgagggct caggtgagca actggtcaca gtcagcagct ctgttgttcc agtgcttccc    3120
agtgctgtgc aaaagttttc tggtacagct tcctccatta tcgacgaagg attgggagaa    3180
gtgggtactg tcaatgaaat tgatagaaga tccaccattt taccaacagc agaagtggaa    3240
ggtacgaaag ctccagtaga gaaggaggaa gtaaggtca gtggcacagt ttcaacaaac    3300 tttcccaaa ctatagagcc agccaaatta tggtctaggc aagaagtcaa ccctgtaaga    3360
caagaaattg aaagtgaaac aacatcagag gaacaaattc aagaagaaaa gtcatttgaa    3420
tcccctcaaa actctcctgc aacagaacaa acaatctttg attcacagac atttactgaa    3480
```

```
actgaactca aaaccacaga ttattctgta ctaacaacaa agaaaactta cagtgatgat    3540
aaagaaatga aggaggaaga cacttcttta gttaacatgt ctactccaga tccagatgca    3600
aatggcttgg aatcttacac aactctccct gaagctactg aaaagtcaca ttttttctta    3660
gctactgcat tagtaactga atctatacca gctgaacatg tagtcacaga ttcaccaatc    3720
aaaaaggaag aaagtacaaa acattttccg aaaggcatga gaccaacaat tcaagagtca    3780
gatactgagc tcttattctc tggactggga tcaggagaag aagttttacc tactctacca    3840
acagagtcag tgaattttac tgaagtggaa caaatcaata acacattata tccccacact    3900
tctcaagtgg aaagtacctc aagtgacaaa attgaagact taacagaat ggaaaatgtg     3960 gcaaaagaag ttggaccact cgtatctcaa acagacatct tgaaggtag tgggtcagta      4020 accagcacaa cattaataga aattttaagt gacactggag cagaaggacc cacggtggca     4080
cctctcccct tctccacgga catcggacat cctcaaaatc agactgtcag gtgggcagaa    4140
gaaatccaga ctagtagacc acaaaccata actgaacaag actctaacaa gaattcttca    4200
acagcagaaa ttaacgaaac aacaacctca tctactgatt ttctggctag agcttatggt    4260
tttgaaatgg ccaaagaatt tgttacatca gcaccaaaac catctgactt gtattatgaa    4320
ccttctggag aaggatctgg agaagtggat attgttgatt catttcacac ttctgcaact    4380
actcaggcaa ccagacaaga aagcagcacc acatttgttt ctgatgggtc cctggaaaaa    4440
catcctgagg tgccaagcgc taaagctgtt actgctgatg gattcccaac agtttcagtg    4500
atgctgcctc ttcattcaga gcagaacaaa agctcccctg atccaactag cacactgtca    4560
aatacagtgt catatgagag gtccacagac ggtagtttcc aagaccgttt cagggaattc    4620
gaggattcca ccttaaaacc taacagaaaa aaacccactg aaaatattat catagacctg    4680
gacaaagagg acaaggattt aatattgaca attacagaga gtaccatcct tgaaattcta    4740
cctgagctga catcggataa aaatactatc atagatattg atcatactaa acctgtgtat    4800
gaagacattc ttggaatgca acagatata gatacagagg taccatcaga accacatgac      4860
agtaatgatg aaagtaatga tgacagcact caagttcaag agatctatga ggcagctgtc    4920
aacctttctt taactgagga aacatttgag ggctctgctg atgttctggc tagctacact    4980
caggcaacac atgatgaatc aatgacttat gaagatagaa gccaactaga tcacatgggc    5040
tttcacttca caactgggat ccctgctcct agcacagaaa cagaattaga cgttttactt    5100
cccacggcaa catccctgcc aattcctcgt aagtctgcca cagttattcc agagattgaa    5160
ggaataaaag ctgaagcaaa agccctggat gacatgtttg aatcaagcac tttgtctgat    5220
ggtcaagcta ttgcagacca aagtgaaata ataccaacat gggccaatt tgaaaggact     5280 caggaggagt atgaagacaa aaaacatgct ggtccttctt ttcagccaga attctcttca    5340
ggagctgagg aggcattagt agaccatact ccctatctaa gtattgctac tacccacctt    5400
atggatcaga gtgtaacaga ggtgcctgat gtgatggaag gatccaatcc cccatattac    5460
actgatacaa cattagcagt ttcaacattt gcgaagttgt cttctcagac accatcatct    5520
cccctcacta tctactcagg cagtgaagcc tctggacaca cagagatccc ccagcccagt    5580
gctctgccag aatagacgt cggctcatct gtaatgtccc cacaggattc ttttaaggaa      5640
attcatgtaa atattgaagc gactttcaaa ccatcaagtg aggaatacct tcacataact    5700
gagcctccct ctttatctcc tgacacaaaa ttagaacctt cagaagatga tggtaaacct    5760
gagttattag aagaaatgga agcttctccc acagaactta ttgctgtgga aggaactgag    5820
attctccaag atttccaaaa caaaaccgat ggtcaagttt ctggagaagc aatcaagatg    5880
```

```
tttcccacca ttaaaacacc tgaggctgga actgttatta caactgccga tgaaattgaa    5940
ttagaaggtg ctacacagtg gccacactct acttctgctt ctgccaccta tggggtcgag    6000
gcaggtgtgg tgccttggct aagtccacag acttctgaga ggcccacgct ttcttcttct    6060
ccagaaataa accctgaaac tcaagcagct ttaatcagag ggcaggattc cacgatagca    6120
gcatcagaac agcaagtggc agcgagaatt cttgattcca atgatcaggc aacagtaaac    6180
cctgtggaat ttaatactga ggttgcaaca ccaccatttt cccttctgga gacttctaat    6240
gaaacagatt tcctgattgg cattaatgaa gagtcagtgg aaggcacggc aatctattta    6300
ccaggacctg atcgctgcaa aatgaacccg tgccttaacg gaggcacctg ttatcctact    6360
gaaacttcct acgtatgcac ctgtgtgcca ggatacagcg gagaccagtg tgaacttgat    6420
tttgatgaat gtcactctaa tccctgtcgt aatggagcca cttgtgttga tggttttaac    6480
acattcaggt gcctctgcct tccaagttat gttggtgcac tttgtgagca agataccgag    6540
acatgtgact atggctggca caaattccaa gggcagtgct acaaatactt tgcccatcga    6600
cgcacatggg atgcagctga cgggaatgcc gtctgcagg gtgcccatct cacaagcatc    6660
ctgtctcacg aagaacaaat gtttgttaat cgtgtgggcc atgattatca gtggataggc    6720
ctcaatgaca agatgtttga gcatgacttc cgttggactg atggcagcac actgcaatac    6780
gagaattgga gacccaacca gccagacagc ttctttttctg ctggagaaga ctgtgttgta    6840
atcatttggc atgagaatgg ccagtggaat gatgttccct gcaattacca tctcacctat    6900
acgtgcaaga aggaacagt cgcttgcggc cagcccccctg ttgtagaaaa tgccaagacc    6960
tttggaaaga tgaaacctcg ttatgaaatc aactccctga ttagatacca ctgcaaagat    7020
ggtttcattc aacgtcacct tccaactatc cggtgcttag gaaatggaag atgggctata    7080
cctaaaatta cctgcatgaa cccatctgca taccaaagga cttattctat gaaatacttt    7140
aaaaattcct catcagcaaa ggacaattca ataaatacat ccaaacatga tcatcgttgg    7200
agccggaggt ggcaggagtc gaggcgctga                                     7230

<210> SEQ ID NO 31
<211> LENGTH: 1089
<212> TYPE: DNA
<213> ORGANISM: Homo sapiens

<400> SEQUENCE: 31
atgttcataa atataaagag catcttatgg atgtgttcaa ccttaatagt aacccatgcg     60
ctacataaag tcaaagtggg aaaaagccca ccggtgaggg gctccctctc tggaaaagtc    120
agcctacctt gtcattttc aacgatgcct actttgccac ccagttacaa caccagtgaa    180
tttctccgca tcaaatggtc taagattgaa gtggacaaaa atggaaaaga tttgaaagag    240
actactgtcc ttgtggccca aaatggaaat atcaagattg gtcaggacta caaagggaga    300
gtgtctgtgc ccacacatcc cgaggctgtg gcgatgcct ccctcactgt ggtcaagctg    360
ctggcaagtg atgcgggtct ttaccgctgt gacgtcatgt acggattga agacacacaa    420 gacacggtgt cactgactgt ggatggggtt gtgtttcact acagggcggc aaccagcagg    480
tacacactga attttgaggc tgctcagaag gcttgtttgg acgttggggc agtcatagca    540
actccagagc agctctttgc tgcctatgaa gatggatttg agcagtgtga cgcaggctgg    600
ctggctgatc agactgtcag atatcccatc cgggctccca gagtaggctg ttatggagat    660
aagatgggaa aggcaggagt caggactat ggattccgtt ctccccagga aacttacgat    720
```

-continued

```
gtgtattgtt atgtggatca tctggatggt gatgtgttcc acctcactgt ccccagtaaa    780
ttcaccttcg aggaggctgc aaaagagtgt gaaaaccagg atgccaggct ggcaacagtg    840
ggggaactcc aggcggcatg gaggaacggc tttgaccagt gcgattacgg gtggctgtcg    900
gatgccagcg tgcgccaccc tgtgactgtg ccagggccc agtgtggagg tggtctactt     960
ggggtgagaa ccctgtatcg ttttgagaac agacaggct tccctccccc tgatagcaga    1020
tttgatgcct actgctttaa acgtcgaatg agtgatttga gtgtaattgg tcatccaata   1080
gattcagaa                                                           1089
```

<210> SEQ ID NO 32
<211> LENGTH: 2409
<212> TYPE: PRT
<213> ORGANISM: Homo sapiens

<400> SEQUENCE: 32

```
Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
                20                  25                  30

Arg Gly Ser Leu Ser Gly Lys Val Ser Leu Pro Cys His Phe Ser Thr
            35                  40                  45

Met Pro Thr Leu Pro Pro Ser Tyr Asn Thr Ser Glu Phe Leu Arg Ile
        50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300
```

-continued

Arg His Pro Val Thr Val Ala Arg Ala Gln Cys Gly Gly Leu Leu
305                 310                 315                 320

Gly Val Arg Thr Leu Tyr Arg Phe Glu Asn Gln Thr Gly Phe Pro Pro
            325                 330                 335

Pro Asp Ser Arg Phe Asp Ala Tyr Cys Phe Lys Arg Arg Met Ser Asp
        340                 345                 350

Leu Ser Val Ile Gly His Pro Ile Asp Ser Glu Ser Lys Glu Asp Glu
    355                 360                 365

Pro Cys Ser Glu Glu Thr Asp Pro Val His Asp Leu Met Ala Glu Ile
370                 375                 380

Leu Pro Glu Phe Pro Asp Ile Ile Glu Ile Asp Leu Tyr His Ser Glu
385                 390                 395                 400

Glu Asn Glu Glu Glu Glu Glu Cys Ala Asn Ala Thr Asp Val Thr
            405                 410                 415

Thr Thr Pro Ser Val Gln Tyr Ile Asn Gly Lys His Leu Val Thr Thr
            420                 425                 430

Val Pro Lys Asp Pro Glu Ala Ala Glu Ala Arg Arg Gly Gln Phe Glu
            435                 440                 445

Ser Val Ala Pro Ser Gln Asn Phe Ser Asp Ser Ser Glu Ser Asp Thr
450                 455                 460

His Pro Phe Val Ile Ala Lys Thr Glu Leu Ser Thr Ala Val Gln Pro
465                 470                 475                 480

Asn Glu Ser Thr Glu Thr Thr Glu Ser Leu Glu Val Thr Trp Lys Pro
            485                 490                 495

Glu Thr Tyr Pro Glu Thr Ser His Phe Ser Gly Gly Glu Pro Asp
            500                 505                 510

Val Phe Pro Thr Val Pro Phe His Glu Glu Phe Glu Ser Gly Thr Ala
            515                 520                 525

Lys Lys Gly Ala Glu Ser Val Thr Glu Arg Asp Thr Glu Val Gly His
            530                 535                 540

Gln Ala His Glu His Thr Glu Pro Val Ser Leu Phe Pro Glu Glu Ser
545                 550                 555                 560

Ser Gly Glu Ile Ala Ile Asp Gln Glu Ser Gln Lys Ile Ala Phe Ala
            565                 570                 575

Arg Ala Thr Glu Val Thr Phe Gly Glu Glu Val Glu Lys Ser Thr Ser
            580                 585                 590

Val Thr Tyr Thr Pro Thr Ile Val Pro Ser Ala Ser Ala Tyr Val
            595                 600                 605

Ser Glu Glu Glu Ala Val Thr Leu Ile Gly Asn Pro Trp Pro Asp Asp
610                 615                 620

Leu Leu Ser Thr Lys Glu Ser Trp Val Glu Ala Thr Pro Arg Gln Val
625                 630                 635                 640

Val Glu Leu Ser Gly Ser Ser Ile Pro Ile Thr Glu Gly Ser Gly
            645                 650                 655

Glu Ala Glu Glu Asp Glu Asp Thr Met Phe Thr Met Val Thr Asp Leu
            660                 665                 670

Ser Gln Arg Asn Thr Thr Asp Thr Leu Ile Thr Leu Asp Thr Ser Arg
            675                 680                 685

Ile Ile Thr Glu Ser Phe Phe Glu Val Pro Ala Thr Thr Ile Tyr Pro
            690                 695                 700

Val Ser Glu Gln Pro Ser Ala Lys Val Val Pro Thr Lys Phe Val Ser
705                 710                 715                 720

Glu Thr Asp Thr Ser Glu Trp Ile Ser Ser Thr Thr Val Glu Glu Lys

```
                725             730             735
Lys Arg Lys Glu Glu Gly Thr Thr Gly Thr Ala Ser Thr Phe Glu
            740             745             750

Val Tyr Ser Ser Thr Gln Arg Ser Asp Gln Leu Ile Leu Pro Phe Glu
            755             760             765

Leu Glu Ser Pro Asn Val Ala Thr Ser Ser Asp Ser Gly Thr Arg Lys
            770             775             780

Ser Phe Met Ser Leu Thr Thr Pro Thr Gln Ser Glu Arg Glu Met Thr
785             790             795             800

Asp Ser Thr Pro Val Phe Thr Glu Thr Asn Thr Leu Glu Asn Leu Gly
                805             810             815

Ala Gln Thr Thr Glu His Ser Ser Ile His Gln Pro Gly Val Gln Glu
            820             825             830

Gly Leu Thr Thr Leu Pro Arg Ser Pro Ala Ser Val Phe Met Glu Gln
            835             840             845

Gly Ser Gly Glu Ala Ala Ala Asp Pro Glu Thr Thr Thr Val Ser Ser
        850             855             860

Phe Ser Leu Asn Val Glu Tyr Ala Ile Gln Ala Glu Lys Glu Val Ala
865             870             875             880

Gly Thr Leu Ser Pro His Val Glu Thr Thr Phe Ser Thr Glu Pro Thr
                885             890             895

Gly Leu Val Leu Ser Thr Val Met Asp Arg Val Val Ala Glu Asn Ile
            900             905             910

Thr Gln Thr Ser Arg Glu Ile Val Ile Ser Glu Arg Leu Gly Glu Pro
            915             920             925

Asn Tyr Gly Ala Glu Ile Arg Gly Phe Ser Thr Gly Phe Pro Leu Glu
930             935             940

Glu Asp Phe Ser Gly Asp Phe Arg Glu Tyr Ser Thr Val Ser His Pro
945             950             955             960

Ile Ala Lys Glu Glu Thr Val Met Met Glu Gly Ser Gly Asp Ala Ala
            965             970             975

Phe Arg Asp Thr Gln Thr Ser Pro Ser Thr Val Pro Thr Ser Val His
            980             985             990

Ile Ser His Ile Ser Asp Ser Glu Gly Pro Ser Ser Thr Met Val Ser
            995             1000            1005

Thr Ser Ala Phe Pro Trp Glu Glu Phe Thr Ser Ser Ala Glu Gly
    1010            1015            1020

Ser Gly Glu Gln Leu Val Thr Val Ser Ser Ser Val Val Pro Val
    1025            1030            1035

Leu Pro Ser Ala Val Gln Lys Phe Ser Gly Thr Ala Ser Ser Ile
    1040            1045            1050

Ile Asp Glu Gly Leu Gly Glu Val Gly Thr Val Asn Glu Ile Asp
    1055            1060            1065

Arg Arg Ser Thr Ile Leu Pro Thr Ala Glu Val Glu Gly Thr Lys
    1070            1075            1080

Ala Pro Val Glu Lys Glu Glu Val Lys Val Ser Gly Thr Val Ser
    1085            1090            1095

Thr Asn Phe Pro Gln Thr Ile Glu Pro Ala Lys Leu Trp Ser Arg
    1100            1105            1110

Gln Glu Val Asn Pro Val Arg Gln Glu Ile Glu Ser Glu Thr Thr
    1115            1120            1125

Ser Glu Glu Gln Ile Gln Glu Glu Lys Ser Phe Glu Ser Pro Gln
    1130            1135            1140
```

```
Asn Ser Pro Ala Thr Glu Gln Thr Ile Phe Asp Ser Gln Thr Phe
    1145            1150                1155

Thr Glu Thr Glu Leu Lys Thr Thr Asp Tyr Ser Val Leu Thr Thr
    1160            1165                1170

Lys Lys Thr Tyr Ser Asp Asp Lys Glu Met Lys Glu Glu Asp Thr
    1175            1180                1185

Ser Leu Val Asn Met Ser Thr Pro Asp Pro Asp Ala Asn Gly Leu
    1190            1195                1200

Glu Ser Tyr Thr Thr Leu Pro Glu Ala Thr Glu Lys Ser His Phe
    1205            1210                1215

Phe Leu Ala Thr Ala Leu Val Thr Glu Ser Ile Pro Ala Glu His
    1220            1225                1230

Val Val Thr Asp Ser Pro Ile Lys Lys Glu Glu Ser Thr Lys His
    1235            1240                1245

Phe Pro Lys Gly Met Arg Pro Thr Ile Gln Glu Ser Asp Thr Glu
    1250            1255                1260

Leu Leu Phe Ser Gly Leu Gly Ser Gly Glu Glu Val Leu Pro Thr
    1265            1270                1275

Leu Pro Thr Glu Ser Val Asn Phe Thr Glu Val Glu Gln Ile Asn
    1280            1285                1290

Asn Thr Leu Tyr Pro His Thr Ser Gln Val Glu Ser Thr Ser Ser
    1295            1300                1305

Asp Lys Ile Glu Asp Phe Asn Arg Met Glu Asn Val Ala Lys Glu
    1310            1315                1320

Val Gly Pro Leu Val Ser Gln Thr Asp Ile Phe Glu Gly Ser Gly
    1325            1330                1335

Ser Val Thr Ser Thr Thr Leu Ile Glu Ile Leu Ser Asp Thr Gly
    1340            1345                1350

Ala Glu Gly Pro Thr Val Ala Pro Leu Pro Phe Ser Thr Asp Ile
    1355            1360                1365

Gly His Pro Gln Asn Gln Thr Val Arg Trp Ala Glu Glu Ile Gln
    1370            1375                1380

Thr Ser Arg Pro Gln Thr Ile Thr Glu Gln Asp Ser Asn Lys Asn
    1385            1390                1395

Ser Ser Thr Ala Glu Ile Asn Glu Thr Thr Thr Ser Ser Thr Asp
    1400            1405                1410

Phe Leu Ala Arg Ala Tyr Gly Phe Glu Met Ala Lys Glu Phe Val
    1415            1420                1425

Thr Ser Ala Pro Lys Pro Ser Asp Leu Tyr Tyr Glu Pro Ser Gly
    1430            1435                1440

Glu Gly Ser Gly Glu Val Asp Ile Val Asp Ser Phe His Thr Ser
    1445            1450                1455

Ala Thr Thr Gln Ala Thr Arg Gln Glu Ser Ser Thr Thr Phe Val
    1460            1465                1470

Ser Asp Gly Ser Leu Glu Lys His Pro Glu Val Pro Ser Ala Lys
    1475            1480                1485

Ala Val Thr Ala Asp Gly Phe Pro Thr Val Ser Val Met Leu Pro
    1490            1495                1500

Leu His Ser Glu Gln Asn Lys Ser Ser Pro Asp Pro Thr Ser Thr
    1505            1510                1515

Leu Ser Asn Thr Val Ser Tyr Glu Arg Ser Thr Asp Gly Ser Phe
    1520            1525                1530
```

-continued

Gln Asp Arg Phe Arg Glu Phe Glu Asp Ser Thr Leu Lys Pro Asn
1535                1540                1545

Arg Lys Lys Pro Thr Glu Asn Ile Ile Ile Asp Leu Asp Lys Glu
1550                1555                1560

Asp Lys Asp Leu Ile Leu Thr Ile Thr Glu Ser Thr Ile Leu Glu
1565                1570                1575

Ile Leu Pro Glu Leu Thr Ser Asp Lys Asn Thr Ile Ile Asp Ile
1580                1585                1590

Asp His Thr Lys Pro Val Tyr Glu Asp Ile Leu Gly Met Gln Thr
1595                1600                1605

Asp Ile Asp Thr Glu Val Pro Ser Glu Pro His Asp Ser Asn Asp
1610                1615                1620

Glu Ser Asn Asp Asp Ser Thr Gln Val Gln Glu Ile Tyr Glu Ala
1625                1630                1635

Ala Val Asn Leu Ser Leu Thr Glu Glu Thr Phe Glu Gly Ser Ala
1640                1645                1650

Asp Val Leu Ala Ser Tyr Thr Gln Ala Thr His Asp Glu Ser Met
1655                1660                1665

Thr Tyr Glu Asp Arg Ser Gln Leu Asp His Met Gly Phe His Phe
1670                1675                1680

Thr Thr Gly Ile Pro Ala Pro Ser Thr Glu Thr Glu Leu Asp Val
1685                1690                1695

Leu Leu Pro Thr Ala Thr Ser Leu Pro Ile Pro Arg Lys Ser Ala
1700                1705                1710

Thr Val Ile Pro Glu Ile Glu Gly Ile Lys Ala Glu Ala Lys Ala
1715                1720                1725

Leu Asp Asp Met Phe Glu Ser Ser Thr Leu Ser Asp Gly Gln Ala
1730                1735                1740

Ile Ala Asp Gln Ser Glu Ile Ile Pro Thr Leu Gly Gln Phe Glu
1745                1750                1755

Arg Thr Gln Glu Glu Tyr Glu Asp Lys Lys His Ala Gly Pro Ser
1760                1765                1770

Phe Gln Pro Glu Phe Ser Ser Gly Ala Glu Glu Ala Leu Val Asp
1775                1780                1785

His Thr Pro Tyr Leu Ser Ile Ala Thr Thr His Leu Met Asp Gln
1790                1795                1800

Ser Val Thr Glu Val Pro Asp Val Met Glu Gly Ser Asn Pro Pro
1805                1810                1815

Tyr Tyr Thr Asp Thr Thr Leu Ala Val Ser Thr Phe Ala Lys Leu
1820                1825                1830

Ser Ser Gln Thr Pro Ser Ser Pro Leu Thr Ile Tyr Ser Gly Ser
1835                1840                1845

Glu Ala Ser Gly His Thr Glu Ile Pro Gln Pro Ser Ala Leu Pro
1850                1855                1860

Gly Ile Asp Val Gly Ser Ser Val Met Ser Pro Gln Asp Ser Phe
1865                1870                1875

Lys Glu Ile His Val Asn Ile Glu Ala Thr Phe Lys Pro Ser Ser
1880                1885                1890

Glu Glu Tyr Leu His Ile Thr Glu Pro Pro Ser Leu Ser Pro Asp
1895                1900                1905

Thr Lys Leu Glu Pro Ser Glu Asp Asp Gly Lys Pro Glu Leu Leu
1910                1915                1920

Glu Glu Met Glu Ala Ser Pro Thr Glu Leu Ile Ala Val Glu Gly

```
            1925                1930                1935

Thr Glu Ile Leu Gln Asp Phe Gln Asn Lys Thr Asp Gly Gln Val
        1940                1945                1950

Ser Gly Glu Ala Ile Lys Met Phe Pro Thr Ile Lys Thr Pro Glu
        1955                1960                1965

Ala Gly Thr Val Ile Thr Thr Ala Asp Glu Ile Glu Leu Glu Gly
        1970                1975                1980

Ala Thr Gln Trp Pro His Ser Thr Ser Ala Ser Ala Thr Tyr Gly
        1985                1990                1995

Val Glu Ala Gly Val Val Pro Trp Leu Ser Pro Gln Thr Ser Glu
        2000                2005                2010

Arg Pro Thr Leu Ser Ser Ser Pro Glu Ile Asn Pro Glu Thr Gln
        2015                2020                2025

Ala Ala Leu Ile Arg Gly Gln Asp Ser Thr Ile Ala Ala Ser Glu
        2030                2035                2040

Gln Gln Val Ala Ala Arg Ile Leu Asp Ser Asn Asp Gln Ala Thr
        2045                2050                2055

Val Asn Pro Val Glu Phe Asn Thr Glu Val Ala Thr Pro Pro Phe
        2060                2065                2070

Ser Leu Leu Glu Thr Ser Asn Glu Thr Asp Phe Leu Ile Gly Ile
        2075                2080                2085

Asn Glu Glu Ser Val Glu Gly Thr Ala Ile Tyr Leu Pro Gly Pro
        2090                2095                2100

Asp Arg Cys Lys Met Asn Pro Cys Leu Asn Gly Gly Thr Cys Tyr
        2105                2110                2115

Pro Thr Glu Thr Ser Tyr Val Cys Thr Cys Val Pro Gly Tyr Ser
        2120                2125                2130

Gly Asp Gln Cys Glu Leu Asp Phe Asp Glu Cys His Ser Asn Pro
        2135                2140                2145

Cys Arg Asn Gly Ala Thr Cys Val Asp Gly Phe Asn Thr Phe Arg
        2150                2155                2160

Cys Leu Cys Leu Pro Ser Tyr Val Gly Ala Leu Cys Glu Gln Asp
        2165                2170                2175

Thr Glu Thr Cys Asp Tyr Gly Trp His Lys Phe Gln Gly Gln Cys
        2180                2185                2190

Tyr Lys Tyr Phe Ala His Arg Arg Thr Trp Asp Ala Ala Glu Arg
        2195                2200                2205

Glu Cys Arg Leu Gln Gly Ala His Leu Thr Ser Ile Leu Ser His
        2210                2215                2220

Glu Glu Gln Met Phe Val Asn Arg Val Gly His Asp Tyr Gln Trp
        2225                2230                2235

Ile Gly Leu Asn Asp Lys Met Phe Glu His Asp Phe Arg Trp Thr
        2240                2245                2250

Asp Gly Ser Thr Leu Gln Tyr Glu Asn Trp Arg Pro Asn Gln Pro
        2255                2260                2265

Asp Ser Phe Phe Ser Ala Gly Glu Asp Cys Val Val Ile Ile Trp
        2270                2275                2280

His Glu Asn Gly Gln Trp Asn Asp Val Pro Cys Asn Tyr His Leu
        2285                2290                2295

Thr Tyr Thr Cys Lys Lys Gly Thr Val Ala Cys Gly Gln Pro Pro
        2300                2305                2310

Val Val Glu Asn Ala Lys Thr Phe Gly Lys Met Lys Pro Arg Tyr
        2315                2320                2325
```

-continued

Glu Ile Asn Ser Leu Ile Arg Tyr His Cys Lys Asp Gly Phe Ile
    2330                2335                2340

Gln Arg His Leu Pro Thr Ile Arg Cys Leu Gly Asn Gly Arg Trp
    2345                2350                2355

Ala Ile Pro Lys Ile Thr Cys Met Asn Pro Ser Ala Tyr Gln Arg
    2360                2365                2370

Thr Tyr Ser Met Lys Tyr Phe Lys Asn Ser Ser Ala Lys Asp
    2375                2380                2385

Asn Ser Ile Asn Thr Ser Lys His Asp His Arg Trp Ser Arg Arg
    2390                2395                2400

Trp Gln Glu Ser Arg Arg
    2405

<210> SEQ ID NO 33
<211> LENGTH: 363
<212> TYPE: PRT
<213> ORGANISM: Homo sapiens

<400> SEQUENCE: 33

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Lys Glu Cys Glu Asn
            260                 265                 270

Gln Asp Ala Arg Leu Ala Thr Val Gly Glu Leu Gln Ala Ala Trp Arg

```
            275                 280                 285
Asn Gly Phe Asp Gln Cys Asp Tyr Gly Trp Leu Ser Asp Ala Ser Val
        290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Arg Met Ser Asp
            340                 345                 350

Leu Ser Val Ile Gly His Pro Ile Asp Ser Glu
                355                 360
```

<210> SEQ ID NO 34
<211> LENGTH: 462
<212> TYPE: DNA
<213> ORGANISM: Homo sapiens

<400> SEQUENCE: 34

| | |
|---|---|
| atgggaaaaa tcagcagtct tccaacccaa ttatttaagt gctgcttttg tgatttcttg | 60 |
| aaggtgaaga tgcacaccat gtcctcctcg catctcttct acctggcgct gtgcctgctc | 120 |
| accttcacca gctctgccac ggctggaccg agacgctct gcggggctga gctggtggat | 180 |
| gctcttcagt tcgtgtgtgg agacaggggc ttttatttca acaagcccac agggtatggc | 240 |
| tccagcagtc ggagggcgcc tcagacaggc atcgtggatg agtgctgctt ccggagctgt | 300 |
| gatctaagga ggctggagat gtattgcgca cccctcaagc ctgccaagtc agctcgctct | 360 |
| gtccgtgccc agcgccacac cgacatgccc aagacccaga aggaagtaca tttgaagaac | 420 |
| gcaagtagag ggagtgcagg aaacaagaac tacaggatgt ag | 462 |

<210> SEQ ID NO 35
<211> LENGTH: 210
<212> TYPE: DNA
<213> ORGANISM: Homo sapiens

<400> SEQUENCE: 35

| | |
|---|---|
| ggaccggaga cgctctgcgg ggctgagctg gtggatgctc ttcagttcgt gtgtggagac | 60 |
| aggggctttt atttcaacaa gcccacaggg tatggctcca gcagtcggag ggcgcctcag | 120 |
| acaggcatcg tggatgagtg ctgcttccgg agctgtgatc taaggaggct ggagatgtat | 180 |
| tgcgcacccc tcaagcctgc caagtcagct | 210 |

<210> SEQ ID NO 36
<211> LENGTH: 144
<212> TYPE: DNA
<213> ORGANISM: Homo sapiens

<400> SEQUENCE: 36

| | |
|---|---|
| atgggaaaaa tcagcagtct tccaacccaa ttatttaagt gctgcttttg tgatttcttg | 60 |
| aaggtgaaga tgcacaccat gtcctcctcg catctcttct acctggcgct gtgcctgctc | 120 |
| accttcacca gctctgccac ggct | 144 |

<210> SEQ ID NO 37
<211> LENGTH: 108
<212> TYPE: DNA
<213> ORGANISM: Homo sapiens

<400> SEQUENCE: 37

```
cgctctgtcc gtgcccagcg ccacaccgac atgcccaaga cccagaagga agtacatttg    60
aagaacgcaa gtagagggag tgcaggaaac aagaactaca ggatgtag                108
```

<210> SEQ ID NO 38
<211> LENGTH: 153
<212> TYPE: PRT
<213> ORGANISM: Homo sapiens

<400> SEQUENCE: 38

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

<210> SEQ ID NO 39
<211> LENGTH: 70
<212> TYPE: PRT
<213> ORGANISM: Homo sapiens

<400> SEQUENCE: 39

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 40
<211> LENGTH: 48
<212> TYPE: PRT
<213> ORGANISM: Homo sapiens

<400> SEQUENCE: 40

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30
```

Phe Tyr Leu Ala Leu Cys Leu Leu Thr Phe Thr Ser Ser Ala Thr Ala
            35                  40                  45

<210> SEQ ID NO 41
<211> LENGTH: 35
<212> TYPE: PRT
<213> ORGANISM: Homo sapiens

<400> SEQUENCE: 41

Arg Ser Val Arg Ala Gln Arg His Thr Asp Met Pro Lys Thr Gln Lys
1               5                   10                  15

Glu Val His Leu Lys Asn Ala Ser Arg Gly Ser Ala Gly Asn Lys Asn
            20                  25                  30

Tyr Arg Met
        35

<210> SEQ ID NO 42
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggccactt tactctgggt tttcgtgact ctgagggtca tcactgcagc tgtcactgta      60
gaaacttcag accatgacaa ctcgctgagt gtcagcatcc ccaaccgtc cccgctgagg      120 gtcctcctgg ggacctccct caccatcccc tgctatttca tcgacccat gcaccctgtg     180 accaccgccc cttctaccgc cccactggcc ccaagaatca agtggagccg tgtgtccaag     240
gagaaggagg tagtgctgct ggtggccact gaagggcgcg tgcgggtcaa cagtgcctat     300
caggacaagg tctcactgcc caactaccg gccatcccca gtgacgccac cttggaagtc     360
cagagcctgc gctccaatga ctctggggtc taccgctgcg aggtgatgca tggcatcgag     420
gacagcgagg ccaccctgga agtcgtggtg aaaggcatcg tgttccatta cagagccatc     480
tctacacgct acacctcga ctttgacagg gcgcagcggg cctgcctgca gaacagtgcc     540
atcattgcca cgcctgagca gctgcaggcc gcctacgaag acggcttcca ccagtgtgac     600
gccggctggc tggctgacca gactgtcaga taccccatcc acactccccg ggaaggctgc     660
tatggagaca aggatgagtt tcctggtgtg aggacgtatg gcatccgaga caccaacgag     720
acctatgatg tgtactgctt cgccgaggag atggagggtg aggtctttta tgcaacatct     780
ccagagaagt tcaccttcca ggaagcagcc aatgagtgcc ggcggctggg tgcccggctg     840
gccaccacgg ccagctctca cctggcctgg caggctggca tggacatgtg cagcgccggc     900
tggctggccg accgcagcgt gcgctacccc atctccaagg cccggcccaa ctgcggtggc     960
aacctcctgg gcgtgaggac cgtctacgtg catgccaacc agacgggcta ccccgacccc    1020
tcatcccgct acgacgccat ctgctacaca ggtgaagact tgtgtgacat cgggcccgag    1080
acgctctgcg gggctgagct ggtggatgct cttcagttcg tgtgtggaga cagggggcttt   1140 tatttcaaca agcccacagg gtatggctcc agcagtcgga gggcgcctca gacaggcatc    1200
gtggatgagt gctgcttccg gagctgtgat ctaaggaggc tggagatgta ttgcgcaccc    1260
ctcaagcctg ccaagtcagc tcgctctgtc cgtgcccagc gccacaccga catgcccaag    1320
acccagaagg aagtacattt gaagaacgca agtagaggga gtgcaggaaa caagaactac    1380
aggatgtag                                                           1389

<210> SEQ ID NO 43
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
gggccccgaga cgctctgcgg ggctgagctg gtggatgctc ttcagttcgt gtgtggagac    60 agggggcttttt atttcaacaa gcccacaggg tatggctcca gcagtcggag ggcgcctcag   120
acaggcatcg tggatgagtg ctgcttccgg agctgtgatc taaggaggct ggagatgtat    180
tgcgcacccc tcaagcctgc caagtcagct cgctctgtcc gtgcccagcg ccacaccgac    240
atgcccaaga cccagaagga agtacatttg aagaacgcaa gtagagggag tgcaggaaac    300
aagaactaca ggatgtag                                                  318
```

<210> SEQ ID NO 44
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Ala Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240
```

```
Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Ala Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Gly Pro Glu Thr Leu Cys Gly Ala Glu Leu Val
        355                 360                 365

Asp Ala Leu Gln Phe Val Cys Gly Asp Arg Gly Phe Tyr Phe Asn Lys
    370                 375                 380

Pro Thr Gly Tyr Gly Ser Ser Arg Arg Ala Pro Gln Thr Gly Ile
385                 390                 395                 400

Val Asp Glu Cys Cys Phe Arg Ser Cys Asp Leu Arg Arg Leu Glu Met
                405                 410                 415

Tyr Cys Ala Pro Leu Lys Pro Ala Lys Ser Ala Arg Ser Val Arg Ala
            420                 425                 430

Gln Arg His Thr Asp Met Pro Lys Thr Gln Lys Glu Val His Leu Lys
        435                 440                 445

Asn Ala Ser Arg Gly Ser Ala Gly Asn Lys Asn Tyr Arg Met
    450                 455                 460

<210> SEQ ID NO 45
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 46
<211> LENGTH: 1380
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 46

```
atggagagtc tacttcttct ggtgctgatt tcaatctgct gggctgatca tctttcagac      60
aactatactc tggatcatga cagagctatt cacatccaag cagaaaatgg cccccatcta     120
cttgtggaag cagagcaagc caaggtgttt cacacagag gtggcaatgt tacactgcca     180
tgtaaatttt atcgagaccc tacagcattt ggctcaggaa tccataaaat ccgaattaag    240
tggaccaagc taacttcgga ttacctcaag gaagtggatg ttttgtttc catgggatac     300
cacaaaaaaa cctatggagg ctaccagggt agagtgtttc tgaagggagg cagtgatagt    360
gatgcttctc tggtcatcac agacctcact ctggaagatt atgggagata taagtgtgag    420
gtgattgaag gattagaaga tgatactgtt gtggtagcac tggacttaca aggtgtggta    480
ttcccttact ttccacgact ggggcgctac aatctcaatt tcacgaggc gcagcaggcg    540
tgtctggacc aggatgctgt gatcgcctcc ttcgaccagc tgtacgacgc ctggcgggc    600
gggctggact ggtgcaatgc cggctggctc agtgatggct ctgtgcaata tcccatcaca   660
aagcccagag agcctgtgg ggggcagaac acagtgcccg gagtcaggaa ctacggattt    720
tgggataaag ataaaagcag atatgatgtt ttctgtttta catccaattt caatggccgt   780
ttttactatc tgatccaccc caccaaactg acctatgatg aagcggtgca agcttgtctc   840
aatgatggtg ctcagattgc aaaagtgggc cagatatttg ctgcctggaa aattctcgga    900
tatgaccgct gtgatgcggg ctggttggcg gatggcagcg tccgctaccc catctctagg    960
ccaagaaggc gctgcagtcc tactgaggct gcagtgcgct tcgtgggttt cccagataaa   1020
aagcataagc tgtatggtgt ctactgcttc agagcataca acgggcccga gacgctctgc   1080
ggggctgagc tggtggatgc tcttcagttc gtgtgtggag acaggggctt ttatttcaac   1140
aagcccacag gtatggctc cagcagtcgg agggcgcctc agacaggcat cgtggatgag   1200
tgctgcttcc ggagctgtga tctaaggagg ctggagatgt attgcgcacc cctcaagcct   1260
gccaagtcag ctcgctctgt ccgtgcccag cgccacaccg catgcccaa gacccagaag   1320
gaagtacatt tgaagaacgc aagtagaggg agtgcaggaa acaagaacta caggatgtag   1380
```

<210> SEQ ID NO 47
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
gggcccgaga cgctctgcgg ggctgagctg gtggatgctc ttcagttcgt gtgtggagac      60
aggggctttt atttcaacaa gcccacaggg tatggctcca gcagtcggag ggcgcctcag    120
acaggcatcg tggatgagtg ctgcttccgg agctgtgatc taaggaggct ggagatgtat    180
tgcgcacccc tcaagcctgc caagtcagct cgctctgtcc gtgcccagcg ccacaccgac    240
atgcccaaga cccagaagga agtacatttg aagaacgcaa gtagagggag tgcaggaaac   300
aagaactaca ggatgtag                                                  318
```

<210> SEQ ID NO 48
<211> LENGTH: 459
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 48

Met Glu Ser Leu Leu Leu Val Leu Ile Ser Ile Cys Trp Ala Asp
1               5                   10                  15

His Leu Ser Asp Asn Tyr Thr Leu Asp His Asp Arg Ala Ile His Ile
            20                  25                  30

Gln Ala Glu Asn Gly Pro His Leu Leu Val Glu Ala Glu Gln Ala Lys
        35                  40                  45

Val Phe Ser His Arg Gly Gly Asn Val Thr Leu Pro Cys Lys Phe Tyr
    50                  55                  60

Arg Asp Pro Thr Ala Phe Gly Ser Gly Ile His Lys Ile Arg Ile Lys
65                  70                  75                  80

Trp Thr Lys Leu Thr Ser Asp Tyr Leu Lys Glu Val Asp Val Phe Val
                85                  90                  95

Ser Met Gly Tyr His Lys Lys Thr Tyr Gly Gly Tyr Gln Gly Arg Val
            100                 105                 110

Phe Leu Lys Gly Gly Ser Asp Ser Asp Ala Ser Leu Val Ile Thr Asp
        115                 120                 125

Leu Thr Leu Glu Asp Tyr Gly Arg Tyr Lys Cys Glu Val Ile Glu Gly
    130                 135                 140

Leu Glu Asp Asp Thr Val Val Val Ala Leu Asp Leu Gln Gly Val Val
145                 150                 155                 160

Phe Pro Tyr Phe Pro Arg Leu Gly Arg Tyr Asn Leu Asn Phe His Glu
                165                 170                 175

Ala Gln Gln Ala Cys Leu Asp Gln Asp Ala Val Ile Ala Ser Phe Asp
            180                 185                 190

Gln Leu Tyr Asp Ala Trp Arg Gly Gly Leu Asp Trp Cys Asn Ala Gly
        195                 200                 205

Trp Leu Ser Asp Gly Ser Val Gln Tyr Pro Ile Thr Lys Pro Arg Glu
    210                 215                 220

Pro Cys Gly Gly Gln Asn Thr Val Pro Gly Val Arg Asn Tyr Gly Phe
225                 230                 235                 240

Trp Asp Lys Asp Lys Ser Arg Tyr Asp Val Phe Cys Phe Thr Ser Asn
                245                 250                 255

Phe Asn Gly Arg Phe Tyr Tyr Leu Ile His Pro Thr Lys Leu Thr Tyr
            260                 265                 270

Asp Glu Ala Val Gln Ala Cys Leu Asn Asp Gly Ala Gln Ile Ala Lys
        275                 280                 285

Val Gly Gln Ile Phe Ala Ala Trp Lys Ile Leu Gly Tyr Asp Arg Cys
    290                 295                 300

Asp Ala Gly Trp Leu Ala Asp Gly Ser Val Arg Tyr Pro Ile Ser Arg
305                 310                 315                 320

Pro Arg Arg Arg Cys Ser Pro Thr Glu Ala Ala Val Arg Phe Val Gly
                325                 330                 335

Phe Pro Asp Lys Lys His Lys Leu Tyr Gly Val Tyr Cys Phe Arg Ala
            340                 345                 350

Tyr Asn Gly Pro Glu Thr Leu Cys Gly Ala Glu Leu Val Asp Ala Leu
        355                 360                 365

Gln Phe Val Cys Gly Asp Arg Gly Phe Tyr Phe Asn Lys Pro Thr Gly
    370                 375                 380

```
Tyr Gly Ser Ser Ser Arg Arg Ala Pro Gln Thr Gly Ile Val Asp Glu
385                 390                 395                 400

Cys Cys Phe Arg Ser Cys Asp Leu Arg Arg Leu Glu Met Tyr Cys Ala
            405                 410                 415

Pro Leu Lys Pro Ala Lys Ser Ala Arg Ser Val Arg Ala Gln Arg His
        420                 425                 430

Thr Asp Met Pro Lys Thr Gln Lys Glu Val His Leu Lys Asn Ala Ser
    435                 440                 445

Arg Gly Ser Ala Gly Asn Lys Asn Tyr Arg Met
    450                 455
```

<210> SEQ ID NO 49
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105
```

<210> SEQ ID NO 50
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atggtcataa atataaagag catcttatgg atgtgttcaa ccttaatagt aacccatgcg      60
ctacataaag tcaaagtggg aaaaagccca ccggtgaggg ctccctctc tggaaaagtc     120 agcctacctt gtcattttc aacgatgcct actttgccac ccagttacaa caccagtgaa     180
tttctccgca tcaaatggtc taagattgaa gtggacaaaa atggaaaaga tttgaaagag     240
actactgtcc ttgtggccca aaatggaaat atcaagattg tcaggactac aaagggaga     300 gtgtctgtgc ccacacatcc cgaggctgtg ggcgatgcct ccctcactgt ggtcaagctg     360
ctggcaagtg atgcgggtct ttaccgctgt gacgtcatgt acgggattga agacacacaa     420
gacacggtgt cactgactgt ggatgggttt gtgtttcact acaggcggc aaccagcagg     480 tacacactga ttttgaggc tgctcagaag gcttgtttgg acgttgggc agtcatagca     540 actccagagc agctctttgc tgcctatgaa atggatttg agcagtgtga cgcaggctgg     600
ctggctgatc agactgtcag atatcccatc cgggctccca gagtaggctg ttatggagat     660
```

```
aagatgggaa aggcaggagt caggacttat ggattccgtt ctccccagga aacttacgat    720
gtgtattgtt atgtggatca tctggatggt gatgtgttcc acctcactgt ccccagtaaa    780
ttcaccttcg aggaggctgc aaaagagtgt gaaaaccagg atgccaggct ggcaacagtg    840
ggggaactcc aggcggcatg gaggaacggc tttgaccagt gcgattacgg gtggctgtcg    900
gatgccagcg tgcgccaccc tgtgactgtg gccagggccc agtgtggagg tggtctactt    960
ggggtgagaa ccctgtatcg ttttgagaac cagacaggct ccctcccccc tgatagcaga   1020
tttgatgcct actgctttaa acgtcgaatg agtgatttga gtgtaattgg tcatccaatt   1080
gattcagaag gaccggagac gctctgcggg gctgagctgg tggatgctct tcagttcgtg   1140
tgtggagaca ggggcttttta tttcaacaag cccacaggggt atggctccag cagtcggagg   1200
gcgcctcaga caggcatcgt ggatgagtgc tgcttccgga gctgtgatct aaggaggctg   1260
gagatgtatt gcgcaccccct caagcctgcc aagtcagctc gctctgtccg tgcccagcgc   1320
cacaccgaca tgcccaagac ccagaaggaa gtacatttga agaacgcaag tagagggagt   1380
gcaggaaaca agaactacag gatgtag                                        1407
```

<210> SEQ ID NO 51
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
ggaccggaga cgctctgcgg ggctgagctg gtggatgctc ttcagttcgt gtgtggagac     60
aggggctttt atttcaacaa gcccacaggg tatggctcca gcagtcggag ggcgcctcag    120
acaggcatcg tggatgagtg ctgcttccgg agctgtgatc taaggaggct ggagatgtat    180
tgcgcacccc tcaagcctgc caagtcagct cgctctgtcc gtgcccagcg ccacaccgac    240
atgcccaaga cccagaagga agtacatttg aagaacgcaa gtagagggag tgcaggaaac    300
aagaactaca ggatgtag                                                   318
```

<210> SEQ ID NO 52
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Val Ile Asn Ile Lys Ser Ile Leu Trp Met Cys Ser Thr Leu Ile
  1               5                  10                  15

Val Thr His Ala Leu His Lys Val Lys Val Gly Lys Ser Pro Pro Val
             20                  25                  30

Arg Gly Ser Leu Ser Gly Lys Val Ser Leu Pro Cys His Phe Ser Thr
         35                  40                  45

Met Pro Thr Leu Pro Pro Ser Tyr Asn Thr Ser Glu Phe Leu Arg Ile
     50                  55                  60

Lys Trp Ser Lys Ile Glu Val Asp Lys Asn Gly Lys Asp Leu Lys Glu
 65                  70                  75                  80

Thr Thr Val Leu Val Ala Gln Asn Gly Asn Ile Lys Ile Gly Gln Asp
                 85                  90                  95
```

```
Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Arg Met Ser Asp
        340                 345                 350

Leu Ser Val Ile Gly His Pro Ile Asp Ser Glu Gly Pro Glu Thr Leu
    355                 360                 365

Cys Gly Ala Glu Leu Val Asp Ala Leu Gln Phe Val Cys Gly Asp Arg
370                 375                 380

Gly Phe Tyr Phe Asn Lys Pro Thr Gly Tyr Gly Ser Ser Ser Arg Arg
385                 390                 395                 400

Ala Pro Gln Thr Gly Ile Val Asp Glu Cys Cys Phe Arg Ser Cys Asp
        405                 410                 415

Leu Arg Arg Leu Glu Met Tyr Cys Ala Pro Leu Lys Pro Ala Lys Ser
    420                 425                 430

Ala Arg Ser Val Arg Ala Gln Arg His Thr Asp Met Pro Lys Thr Gln
        435                 440                 445

Lys Glu Val His Leu Lys Asn Ala Ser Arg Gly Ser Ala Gly Asn Lys
    450                 455                 460

Asn Tyr Arg Met
465

<210> SEQ ID NO 53
<211> LENGTH: 105
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 53

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 54
<211> LENGTH: 1086
<212> TYPE: DNA
<213> ORGANISM: Homo sapiens

<400> SEQUENCE: 54
atggacaagt tttggtggca cgcagcctgg ggactctgcc tcgtgccgct gagcctggcg      60
cagatcgatt tgaatataac ctgccgcttt gcaggtgtat tccacgtgga aaaaatggt     120 cgctacagca tctctcggac ggaggccgct gacctctgca aggctttcaa tagcaccttg     180
cccacaatgg cccagatgga aaagctctg agcatcggat tgagacctg caggtatggg      240 ttcatagaag ggcacgtggt gattccccgg atccacccca actccatctg tgcagcaaac     300
aacacagggg tgtacatcct cacatccaac acctcccagt atgacacata ttgcttcaat     360
gcttcagctc cacctgaaga agattgtaca tcagtcacag acctgcccaa tgcctttgat     420
ggaccaatta ccataactat tgttaaccgt gatggcaccc gctatgtcca gaaaggagaa     480
tacagaacga atcctgaaga catctacccc agcaacccta ctgatgatga cgtgagcagc     540
ggctcctcca gtgaaaggag cagcacttca ggaggttaca tcttttacac cttttctact     600
gtacacccca tcccagacga agacagtccc tggatcaccg acagcacaga cagaatccct     660
gctaccagag accaagacac attccacccc agtgggggt cccataccac tcatggatct     720
gaatcagatg gacactcaca tgggagtcaa aaggtggag caaacacaac ctctggtcct     780
ataaggacac cccaaattcc agaatggctg atcatcttgg catccctctt ggccttggct     840
ttgattcttg cagtttgcat tgcagtcaac agtcgaagaa ggtgtgggca agaaaaag       900 ctagtgatca acagtggcaa tggagctgtg gaggacagaa agccaagtgg actcaacgga     960
gaggccagca gtctcaggaa atggtgcat tggtgaaca aggagtcgtc agaaactcca       1020
gaccagttta tgacagctga tgagacaagg aacctgcaga atgtggacat gaagattggg     1080
gtgtaa                                                               1086

<210> SEQ ID NO 55
<211> LENGTH: 804
<212> TYPE: DNA
<213> ORGANISM: Homo sapiens

<400> SEQUENCE: 55

```
atggacaagt tttggtggca cgcagcctgg ggactctgcc tcgtgccgct gagcctggcg      60
cagatcgatt tgaatataac ctgccgcttt gcaggtgtat ccacgtgga gaaaaatggt      120 cgctacagca tctctcggac ggaggccgct gacctctgca aggctttcaa tagcaccttg     180
cccacaatgg cccagatgga gaaagctctg agcatcggat tgagacctg caggtatggg      240 ttcatagaag ggcacgtggt gattccccgg atccaccca actccatctg tgcagcaaac     300
aacacagggg tgtacatcct cacatccaac acctcccagt atgacacata ttgcttcaat    360
gcttcagctc cacctgaaga agattgtaca tcagtcacag acctgcccaa tgcctttgat    420
ggaccaatta ccataactat tgttaaccgt gatggcaccc gctatgtcca gaaaggagaa    480
tacagaacga atcctgaaga catctacccc agcaacccta ctgatgatga cgtgagcagc    540
ggctcctcca gtgaaaggag cagcacttca ggaggttaca tcttttacac cttttctact    600
gtacacccca tcccagacga agacagtccc tggatcaccg acagcacaga cagaatccct    660
gctaccagag accaagacac attccacccc agtgggggt cccataccac tcatggatct    720
gaatcagatg gacactcaca tgggagtcaa gaaggtggag caaacacaac ctctggtcct    780
ataaggacac cccaaattcc agaa                                            804

<210> SEQ ID NO 56
<211> LENGTH: 60
<212> TYPE: DNA
<213> ORGANISM: Homo sapiens

<400> SEQUENCE: 56
tggctgatca tcttggcatc cctcttggcc ttggctttga ttcttgcagt ttgcattgca    60

<210> SEQ ID NO 57
<211> LENGTH: 222
<212> TYPE: DNA
<213> ORGANISM: Homo sapiens

<400> SEQUENCE: 57
gtcaacagtc gaagaaggtg tgggcagaag aaaaagctag tgatcaacag tggcaatgga   60
gctgtggagg acagaaagcc aagtggactc aacggagagg ccagcaagtc tcaggaaatg  120
gtgcatttgg tgaacaagga gtcgtcagaa actccagacc agtttatgac agctgatgag  180
acaaggaacc tgcagaatgt ggacatgaag attggggtgt aa                      222

<210> SEQ ID NO 58
<211> LENGTH: 361
<212> TYPE: PRT
<213> ORGANISM: Homo sapiens

<400> SEQUENCE: 58

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95
```

Cys Ala Ala Asn Asn Thr Gly Val Tyr Ile Leu Thr Ser Asn Thr Ser
                100                 105                 110

Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Arg Asp
    210                 215                 220

Gln Asp Thr Phe His Pro Ser Gly Gly Ser His Thr Thr His Gly Ser
225                 230                 235                 240

Glu Ser Asp Gly His Ser His Gly Ser Gln Glu Gly Gly Ala Asn Thr
                245                 250                 255

Thr Ser Gly Pro Ile Arg Thr Pro Gln Ile Pro Glu Trp Leu Ile Ile
            260                 265                 270

Leu Ala Ser Leu Leu Ala Leu Ala Leu Ile Leu Ala Val Cys Ile Ala
        275                 280                 285

Val Asn Ser Arg Arg Arg Cys Gly Gln Lys Lys Lys Leu Val Ile Asn
    290                 295                 300

Ser Gly Asn Gly Ala Val Glu Asp Arg Lys Pro Ser Gly Leu Asn Gly
305                 310                 315                 320

Glu Ala Ser Lys Ser Gln Glu Met Val His Leu Val Asn Lys Glu Ser
                325                 330                 335

Ser Glu Thr Pro Asp Gln Phe Met Thr Ala Asp Glu Thr Arg Asn Leu
            340                 345                 350

Gln Asn Val Asp Met Lys Ile Gly Val
        355                 360

<210> SEQ ID NO 59
<211> LENGTH: 268
<212> TYPE: PRT
<213> ORGANISM: Homo sapiens

<400> SEQUENCE: 59

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser

```
                100                 105                 110
Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
        130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Arg Asp
    210                 215                 220

Gln Asp Thr Phe His Pro Ser Gly Gly Ser His Thr Thr His Gly Ser
225                 230                 235                 240

Glu Ser Asp Gly His Ser His Gly Ser Gln Glu Gly Gly Ala Asn Thr
                245                 250                 255

Thr Ser Gly Pro Ile Arg Thr Pro Gln Ile Pro Glu
            260                 265
```

<210> SEQ ID NO 60
<211> LENGTH: 21
<212> TYPE: PRT
<213> ORGANISM: Homo sapiens

<400> SEQUENCE: 60

```
Trp Leu Ile Ile Leu Ala Ser Leu Leu Ala Leu Ala Leu Ile Leu Ala
1               5                   10                  15

Val Cys Ile Ala Val
            20
```

<210> SEQ ID NO 61
<211> LENGTH: 72
<212> TYPE: PRT
<213> ORGANISM: Homo sapiens

<400> SEQUENCE: 61

```
Asn Ser Arg Arg Arg Cys Gly Gln Lys Lys Lys Leu Val Ile Asn Ser
1               5                   10                  15

Gly Asn Gly Ala Val Glu Asp Arg Lys Pro Ser Gly Leu Asn Gly Glu
            20                  25                  30

Ala Ser Lys Ser Gln Glu Met Val His Leu Val Asn Lys Glu Ser Ser
        35                  40                  45

Glu Thr Pro Asp Gln Phe Met Thr Ala Asp Glu Thr Arg Asn Leu Gln
    50                  55                  60

Asn Val Asp Met Lys Ile Gly Val
65                  70
```

<210> SEQ ID NO 62
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
cccacaatgg cccagatgga gaaagctctg agcatcggat tgagacctg caggtatggg      240 ttcatagaag ggcacgtggt gattccccgg atccacccca actccatctg tgcagcaaac     300
aacacagggg tgtacatcct cacatccaac acctcccagt atgacacata ttgcttcaat     360
gcttcagctc cacctgaaga agattgtaca tcagtcgggc ccgagacgct ctgcggggct     420
gagctggtgg atgctcttca gttcgtgtgt ggagacaggg gctttatttt caacaagccc     480
acagggtatg gctccagcag tcggagggcg cctcagacag gcatcgtgga tgagtgctgc     540
ttccggagct gtgatctaag gaggctggag atgtattgcg cacccctcaa gcctgccaag     600
tcagctcgct ctgtccgtgc ccagcgccac accgacatgc ccaagaccca gaaggaagta     660
catttgaaga acgcaagtag agggagtgca ggaaacaaga actacaggat gtag           714

<210> SEQ ID NO 63
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gggcccgaga cgctctgcgg ggctgagctg gtggatgctc ttcagttcgt gtgtggagac      60
aggggctttt atttcaacaa gcccacaggg tatggctcca gcagtcggag ggcgcctcag     120
acaggcatcg tggatgagtg ctgcttccgg agctgtgatc taaggaggct ggagatgtat     180
tgcgcacccc tcaagcctgc caagtcagct cgctctgtcc gtgcccagcg ccacaccgac     240
atgcccaaga cccagaagga agtacatttg aagaacgcaa gtagagggag tgcaggaaac     300
aagaactaca ggatgtag                                                    318

<210> SEQ ID NO 64
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110
```

Gln Tyr Asp Thr Tyr Cys Phe Asn Ala Ser Ala Pro Pro Glu Glu Asp
            115                 120                 125

Cys Thr Ser Val Gly Pro Glu Thr Leu Cys Gly Ala Glu Leu Val Asp
        130                 135                 140

Ala Leu Gln Phe Val Cys Gly Asp Arg Gly Phe Tyr Phe Asn Lys Pro
145                 150                 155                 160

Thr Gly Tyr Gly Ser Ser Ser Arg Arg Ala Pro Gln Thr Gly Ile Val
                165                 170                 175

Asp Glu Cys Cys Phe Arg Ser Cys Asp Leu Arg Arg Leu Glu Met Tyr
            180                 185                 190

Cys Ala Pro Leu Lys Pro Ala Lys Ser Ala Arg Ser Val Arg Ala Gln
            195                 200                 205

Arg His Thr Asp Met Pro Lys Thr Gln Lys Glu Val His Leu Lys Asn
        210                 215                 220

Ala Ser Arg Gly Ser Ala Gly Asn Lys Asn Tyr Arg Met
225                 230                 235

<210> SEQ ID NO 65
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
 50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 66
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt    120
cgctacagca tctctcggac ggaggccgct gacctctgca aggctttcaa tagcaccttg    180
cccacaatgg cccagatgga gaaagctctg agcatcggat ttgagacctg caggtatggg    240
ttcatagaag ggcacgtggt gattcccggg atccacccca actccatctg tgcagcaaac    300
aacacagggg tgtacatcct cacatccaac acctcccagt atgacacata ttgcttcaat    360

```
gcttcagctc cacctgaaga agattgtaca tcagtcacag acctgcccaa tgcctttgat    420
ggaccaatta ccataactat tgttaaccgt gatggcaccc gctatgtcgg gcccgagacg    480
ctctgcgggg ctgagctggt ggatgctctt cagttcgtgt gtggagacag gggctttttat    540 ttcaacaagc ccacaggta tggctccagc agtcggaggg cgcctcagac aggcatcgtg     600
gatgagtgct gcttccggag ctgtgatcta aggaggctgg agatgtattg cgcacccctc    660
aagcctgcca gtcagctcg ctctgtccgt gcccagcgcc acaccgacat gcccaagacc     720
cagaaggaag tacatttgaa gaacgcaagt agagggagtg caggaaacaa gaactacagg    780
atgtag                                                              786
```

<210> SEQ ID NO 67
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gggcccgaga cgctctgcgg ggctgagctg gtggatgctc ttcagttcgt gtgtggagac     60
aggggctttt atttcaacaa gcccacaggg tatggctcca gcagtcggag ggcgcctcag    120
acaggcatcg tggatgagtg ctgcttccgg agctgtgatc taaggaggct ggagatgtat    180
tgcgcacccc tcaagcctgc caagtcagct cgctctgtcc gtgcccagcg ccacaccgac    240
atgcccaaga cccagaagga agtacatttg aagaacgcaa gtagagggag tgcaggaaac    300
aagaactaca ggatgtag                                                 318
```

<210> SEQ ID NO 68
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gly Pro Glu Thr
```

```
                    145                 150                 155                 160
Leu Cys Gly Ala Glu Leu Val Asp Ala Leu Gln Phe Val Cys Gly Asp
                165                 170                 175

Arg Gly Phe Tyr Phe Asn Lys Pro Thr Gly Tyr Gly Ser Ser Ser Arg
            180                 185                 190

Arg Ala Pro Gln Thr Gly Ile Val Asp Glu Cys Cys Phe Arg Ser Cys
        195                 200                 205

Asp Leu Arg Arg Leu Glu Met Tyr Cys Ala Pro Leu Lys Pro Ala Lys
    210                 215                 220

Ser Ala Arg Ser Val Arg Ala Gln Arg His Thr Asp Met Pro Lys Thr
225                 230                 235                 240

Gln Lys Glu Val His Leu Lys Asn Ala Ser Arg Gly Ser Ala Gly Asn
                245                 250                 255

Lys Asn Tyr Arg Met
            260

<210> SEQ ID NO 69
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 70
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggacaagt tttggtggca cgcagcctgg ggactctgcc tcgtgccgct gagcctggcg      60
cagatcgatt tgaatataac ctgccgcttt gcaggtgtat ccacgtggaa gaaaaatggt    120
cgctacagca tctctcggac ggaggccgct gacctctgca aggctttcaa tagcaccttg    180
cccacaatgg cccagatgga gaaagctctg agcatcggat tgagacctgc aggtatggg     240 ttcatagaag gcacgtggtg gattcccccgg atccacccca actccatctg tgcagcaaac    300
aacacagggg tgtacatcct cacatccaac acctcccagt atgacacata ttgcttcaat    360
gcttcagctc cacctgaaga agattgtaca tcagtcacag acctgccaa tgcctttgat    420
```

```
ggaccaatta ccataactat tgttaaccgt gatggcaccc gctatgtcca gaaaggagaa    480
tacagaacga atcctgaaga catctacccc agcaaccccta ctgatgatga cgtggggccc   540
gagacgctct gcggggctga gctggtggat gctcttcagt tcgtgtgtgg agacaggggc   600 tttatttca acaagcccac agggtatggc tccagcagtc ggagggcgcc tcagacaggc    660
atcgtggatg agtgctgctt ccggagctgt gatctaagga ggctggagat gtattgcgca   720 ccctcaagc ctgccaagtc agctcgctct gtccgtgccc agcgccacac cgacatgccc    780
aagacccaga aggaagtaca tttgaagaac gcaagtagag ggagtgcagg aaacaagaac   840
tacaggatgt ag                                                        852
```

<210> SEQ ID NO 71
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gggcccgaga cgctctgcgg ggctgagctg gtggatgctc ttcagttcgt gtgtggagac    60
aggggctttt atttcaacaa gcccacaggg tatggctcca gcagtcggag ggcgcctcag   120
acaggcatcg tggatgagtg ctgcttccgg agctgtgatc taaggaggct ggagatgtat   180
tgcgcacccc tcaagcctgc caagtcagct cgctctgtcc gtgcccagcg ccacaccgac   240
atgcccaaga cccagaagga agtacatttg aagaacgcaa gtagagggag tgcaggaaac   300
aagaactaca ggatgtag                                                  318
```

<210> SEQ ID NO 72
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
```

```
                145                 150                 155                 160
Tyr Arg Thr Asn Pro Glu Asp Ile Tyr Pro Ser Asn Pro Thr Asp Asp
                    165                 170                 175

Asp Val Gly Pro Glu Thr Leu Cys Gly Ala Glu Leu Val Asp Ala Leu
                180                 185                 190

Gln Phe Val Cys Gly Asp Arg Gly Phe Tyr Phe Asn Lys Pro Thr Gly
            195                 200                 205

Tyr Gly Ser Ser Arg Arg Ala Pro Gln Thr Gly Ile Val Asp Glu
        210                 215                 220

Cys Cys Phe Arg Ser Cys Asp Leu Arg Arg Leu Glu Met Tyr Cys Ala
225                 230                 235                 240

Pro Leu Lys Pro Ala Lys Ser Ala Arg Ser Val Arg Ala Gln Arg His
                245                 250                 255

Thr Asp Met Pro Lys Thr Gln Lys Glu Val His Leu Lys Asn Ala Ser
            260                 265                 270

Arg Gly Ser Ala Gly Asn Lys Asn Tyr Arg Met
        275                 280
```

<210> SEQ ID NO 73
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105
```

<210> SEQ ID NO 74
<211> LENGTH: 984
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
atggacaagt tttggtggca cgcagcctgg ggactctgcc tcgtgccgct gagcctggcg      60
cagatcgatt tgaatataac ctgccgcttt gcaggtgtat ccacgtggaa gaaaatggt     120 cgctacagca tctctcggac ggaggccgct gacctctgca aggctttcaa tagcaccttg    180
cccacaatgg cccagatgga gaaagctctg agcatcggat tgagacctg caggtatggg     240 ttcatagaag ggcacgtggt gattcccgg atccaccca actccatctg tgcagcaaac      300
```

```
aacacagggg tgtacatcct cacatccaac acctcccagt atgacacata ttgcttcaat    360
gcttcagctc cacctgaaga agattgtaca tcagtcacag acctgcccaa tgcctttgat    420
ggaccaatta ccataactat tgttaaccgt gatggcaccc gctatgtcca gaaaggagaa    480
tacagaacga atcctgaaga catctacccc agcaaccctga ctgatgatga cgtgagcagc    540
ggctcctcca gtgaaaggag cagcacttca ggaggttaca tcttttacac cttttctact    600
gtacacccca tcccagacga agacagtccc tggatcaccg acagcacaga cagaatccct    660
gctaccgggc ccgagacgct ctgcggggct gagctggtgg atgctcttca gttcgtgtgt    720
ggagacaggg gcttttattt caacaagccc acagggtatg gctccagcag tcggagggcg    780
cctcagacag gcatcgtgga tgagtgctgc ttccggagct gtgatctaag gaggctggag    840
atgtattgcg caccctcaa gcctgccaag tcagctcgct ctgtccgtgc ccagcgccac    900
accgacatgc ccaagaccca gaggaagta catttgaaga acgcaagtag agggagtgca    960
ggaaacaaga actacaggat gtag                                          984
```

```
<210> SEQ ID NO 75
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gggcccgaga cgctctgcgg ggctgagctg gtggatgctc ttcagttcgt gtgtggagac     60
aggggctttt atttcaacaa gcccacaggg tatggctcca gcagtcggag gcgcctcag    120 acaggcatcg tggatgagtg ctgcttccgg agctgtgatc taaggaggct ggagatgtat    180
tgcgcacccc tcaagcctgc caagtcagct cgctctgtcc gtgcccagcg ccacaccgac    240
atgcccaaga cccagaagga agtacatttg aagaacgcaa gtagagggag tgcaggaaac    300
aagaactaca ggatgtag                                                  318
```

```
<210> SEQ ID NO 76
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110
```

```
Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
        130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Gly Pro
        210                 215                 220

Glu Thr Leu Cys Gly Ala Glu Leu Val Asp Ala Leu Gln Phe Val Cys
225                 230                 235                 240

Gly Asp Arg Gly Phe Tyr Phe Asn Lys Pro Thr Gly Tyr Gly Ser Ser
                245                 250                 255

Ser Arg Arg Ala Pro Gln Thr Gly Ile Val Asp Glu Cys Cys Phe Arg
            260                 265                 270

Ser Cys Asp Leu Arg Arg Leu Glu Met Tyr Cys Ala Pro Leu Lys Pro
            275                 280                 285

Ala Lys Ser Ala Arg Ser Val Arg Ala Gln Arg His Thr Asp Met Pro
        290                 295                 300

Lys Thr Gln Lys Glu Val His Leu Lys Asn Ala Ser Arg Gly Ser Ala
305                 310                 315                 320

Gly Asn Lys Asn Tyr Arg Met
                325

<210> SEQ ID NO 77
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105
```